(12) United States Patent
Yamada et al.

(10) Patent No.: US 11,958,802 B2
(45) Date of Patent: Apr. 16, 2024

(54) MIGRATION-RESISTANT PHOTOPOLYMERIZATION SENSITIZER

(71) Applicant: Kawasaki Kasei Chemicals Ltd., Kawasaki (JP)

(72) Inventors: Akihiko Yamada, Kawasaki (JP); Hidehiko Tanaka, Kawasaki (JP); Shigeaki Numata, Kawasaki (JP)

(73) Assignee: Kawasaki Kasei Chemicals Ltd., Kawasaki (JP)

( * ) Notice: Subject to any disclaimer, the term of this patent is extended or adjusted under 35 U.S.C. 154(b) by 455 days.

(21) Appl. No.: 17/312,274

(22) PCT Filed: Mar. 29, 2019

(86) PCT No.: PCT/JP2019/014347
§ 371 (c)(1),
(2) Date: Jun. 9, 2021

(87) PCT Pub. No.: WO2020/121544
PCT Pub. Date: Jun. 18, 2020

(65) Prior Publication Data
US 2022/0106254 A1    Apr. 7, 2022

(30) Foreign Application Priority Data

Dec. 10, 2018    (WO) ................. PCT/JP2018/045376

(51) Int. Cl.
| C07C 69/736 | (2006.01) |
| C07C 67/08 | (2006.01) |
| C07C 67/10 | (2006.01) |
| C07C 67/26 | (2006.01) |
| C07C 67/343 | (2006.01) |
| C08F 2/50 | (2006.01) |

(52) U.S. Cl.
CPC ............ *C07C 69/736* (2013.01); *C07C 67/08* (2013.01); *C07C 67/10* (2013.01); *C07C 67/26* (2013.01); *C07C 67/343* (2013.01); *C08F 2/50* (2013.01); *C07C 2603/24* (2017.05)

(58) Field of Classification Search
CPC ....... C07C 69/736; C07C 67/08; C07C 67/10; C07C 67/26; C07C 67/343; C07C 2603/24; C08F 1/50
See application file for complete search history.

(56) References Cited

FOREIGN PATENT DOCUMENTS

| CN | 105037587 A | 11/2015 |
| CN | 107325237 A | 11/2017 |
| JP | 5-249606 A | 9/1993 |
| JP | 6-345614 A | 12/1994 |
| JP | 7-62010 A | 3/1995 |
| JP | 10-195117 A | 7/1998 |
| JP | 11-279212 A | 10/1999 |
| JP | 2000-344704 A | 12/2000 |
| JP | 2002-302507 A | 10/2002 |
| JP | WO2007/126066 A1 | 11/2007 |
| JP | 4605223 B2 | 1/2011 |
| JP | 2014-31346 A | 2/2014 |
| JP | 2014-101442 A | 6/2014 |
| JP | 2017-193523 A | 10/2017 |
| JP | 2018-2630 A | 1/2018 |

(Continued)

OTHER PUBLICATIONS

Hinschberger, et al., Synthesis and photophysical Properties of Fluorescent Anthracenophanes Incorporating Two Polyoxadioxoalkane Chains, J. Chem. Soc., Perkin Transactions 2, 6, pp. 993-1000 (Year: 1990).*

(Continued)

*Primary Examiner* — Yate' K Cutliff
(74) *Attorney, Agent, or Firm* — Oblon, McClelland, Maier & Neustadt, L.L.P.

(57) ABSTRACT

A photopolymerization sensitizer may not cause problems of dusting or coloring of a cured product due to bleeding of additives such as the photopolymerization sensitizer on the surface, e.g., by blooming at the time of photo-curing or during storage of the cured product, and which provides a practically sufficient photo-curing rate. A 9,10-bis(alkoxy-carbonylalkyleneoxy)anthracene compound having ester groups, of formula (I):

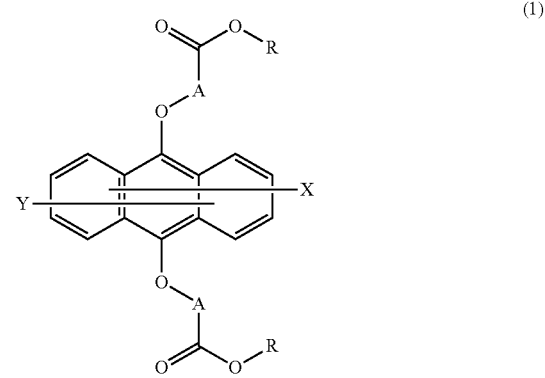

wherein A is a $C_{1-20}$ alkylene group, optionally branched by an alkyl group, R is a $C_{1-20}$ alkyl group, optionally branched by the alkyl group, the $C_{1-20}$ alkyl group optionally being a cycloalkyl group or a cycloalkylalkyl group, and X and Y are independently a hydrogen, a $C_{1-8}$ alkyl group, or a halogen.

13 Claims, No Drawings

(56) References Cited

FOREIGN PATENT DOCUMENTS

| JP | 2018-90537 A | 6/2018 |
| JP | 2018-115256 A | 7/2018 |
| WO | WO 2014/109303 A1 | 7/2014 |

OTHER PUBLICATIONS

International Search Report dated May 28, 2019 in PCT/JP2019/014347 filed on Mar. 29, 2019, 2 pages.

Hinschberger et al., "Synthesis and Photophysical Properties of Fluorescent Anthracenophanes Incorporating Two Polyoxadioxoalkane Chains", Journal of the Chemical Society, Perkin Transactions 2, 1990, pp. 993-1000.

Sandra G. König, et al.; "'Caged' peptide nucleic acids activated by red light in a singlet oxygen mediated process"; Biorganics & Medicinal Chemistry Letters 23 (2013) 6544-6548.

* cited by examiner

MIGRATION-RESISTANT PHOTOPOLYMERIZATION SENSITIZER

CROSS-REFERENCE TO RELATED APPLICATIONS

The present application is the national stage of international application PCT/JP2019/014347, filed on Mar. 29, 2019, and claims the benefit of the filing date of international application PCT/JP2018/045376, filed on Dec. 10, 2018.

TECHNICAL FIELD

The present invention relates to a 9,10-bis(alkoxycarbonylalkyleneoxy)anthracene compound having ester groups and its production method, and a photopolymerization sensitizer containing a 9,10-bis(alkoxycarbonylalkyleneoxy) anthracene compound having ester groups.

BACKGROUND ART

A photo-curing resin polymerizable by active energy rays such as ultraviolet rays or visible rays, which is quickly cured and can thereby remarkably reduce the amount of an organic solvent used as compared with a thermosetting resin, is superior in that the working environment can be improved and the environmental burden can be reduced. A conventional photo-curing resin by itself lacks polymerization initiation function and usually requires a photopolymerization initiator so as to be cured. The photopolymerization initiator may, for example, be an alkylphenone polymerization initiator such as hydroxyacetophenone or benzophenone, an acylphosphine oxide photopolymerization initiator or an onium salt (Patent Documents 1, 2 and 3). If an onium salt initiator is used among such photopolymerization initiators, an onium salt has light absorption in the vicinity of from 225 nm to 350 nm and has no absorption at a wavelength of 350 nm or longer, and accordingly if a long wavelength lamp at a wavelength of at least 350 nm is used as a light source, the photo-curing reaction hardly proceeds, and it is common to add a photopolymerization sensitizer. Likewise, many of photopolymerization initiators such as an alkylphenone polymerization initiator have no absorption at 350 nm or longer. As a photopolymerization sensitizer for such photopolymerization initiators, anthracene compounds and thioxanthone compounds are known, and particularly an anthracene compound is used in many cases in view of the color, etc. (Patent Document 4).

As the anthracene photopolymerization sensitizer, a 9,10-dialkoxyanthracene compound is used. For example, for a iodonium salt which is a photopolymerization initiator in photopolymerization, as the photopolymerization sensitizer, a 9,10-dialkoxyanthracene compound such as 9,10-dibutoxyanthracene or 9,10-diethoxyanthracene has been used (Patent Documents 5, 6, 7 and 8).

However, it is known that such a 9,10-dialkoxyanthracene compound as the photopolymerization sensitizer bleeds on the surface e.g. by blooming during storage of a photopolymerizable composition before photo-curing or of the photo-cured product, thus leading to problems of dusting or coloring of the cured product.

With respect to the photopolymerizable composition, for example, in a case where the above photopolymerization sensitizer is used as a component of a photo-adhesive to bond films, the photopolymerization sensitizer may migrate to the upper film, thus leading to a problem of dusting of the photopolymerization sensitizer on the upper film or coloring.

Further, a dry film resist is used in processing such as production of a printed wiring board, production of a lead frame and production of a metal mask, and a dry film resist applicable to 405 nm semiconductor has been required, and as a photopolymerization sensitizer corresponding to such a wavelength, thioxanthone or a 9,10-dialkoxyanthrathene compound has been used. A dry film resist is stored and merchandised in a state where a photosensitive resin composition is covered with a film, and as the film, a polyethylene film or a polypropylene film is used, and the photopolymerization sensitizer may migrate to the film, thus lowering the sensitizing effect, or causing dusting on the film (Patent Document 9).

In order to prevent such migration of the photopolymerization sensitizer, a 9,10-bis(2-acyloxyalkoxy)anthracene compound having ester groups as a polar group introduced to an alkoxy group of a 9,10-dialkoxyanthracene compound has been reported (Patent Document 10). However, production of the 9,10-bis(2-acyloxyalkoxy)anthracene compound requires a step of using an oxidized alkylene compound, thus increasing the number of steps and increasing the cost, and in addition, the oxidized alkylene compound particularly ethylene oxide being hardly available and being difficult to handle is a great problem in production of the 9,10-bis(2-acyloxyalkoxy)anthracene compound.

Further, a compound having an alkoxy group of the 9,10-dialkoxyanthracene compound converted to an acyl group, and the like, have been developed, however, although migration resistance is suppressed, electron-donating property of the alkoxy group is decreased, and the absorption wavelength tends to shift to the short wavelength side (Patent Document 11).

PRIOR ART DOCUMENTS

Patent Document

Patent Document 1: JP-A-H06-345614
Patent Document 2: JP-A-H07-062010
Patent Document 3: JP-A-H05-249606
Patent Document 4: JP-A-H10-195117
Patent Document 5: JP-A-2002-302507
Patent Document 6: JP-A-H11-279212
Patent Document 7: JP-A-2000-344704
Patent Document 8: WO2007/126066
Patent Document 9: Japanese Patent No. 4605223
Patent Document 10: JP-A-2014-031346
Patent document 11: JP-A-2014-101442

DISCLOSURE OF INVENTION

Technical Problem

Under these circumstances, development of a novel photopolymerization sensitizer which not only has migration resistance and will not cause problems of dusting or coloring of a cured product at the time of photo-curing or during storage of the cured product, but also can be obtained by a practical production method using an easily available material, has been desired.

Solution to Problem

The present inventors have conducted extensive studies on the structure and physical properties of anthracene compounds and as a result, found that the 9,10-bis(alkoxycarbonylalkyleneoxy)anthracene compound having ester groups of the present invention has an excellent effect as a photopolymerization sensitizer in photopolymerization reaction and in addition, the photopolymerization sensitizer is less likely to migrate and cause blooming since it has easter groups as a polar group, and further found a practical production method using an easily available material, and accomplished the present invention.

That is, according to a first embodiment of the present invention, provided is a 9,10-bis(alkoxycarbonylalkyleneoxy)anthracene compound having ester groups, represented by the following formula (1):

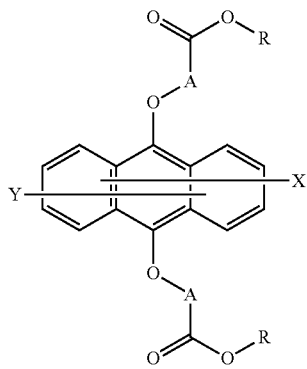

(1)

wherein A is a $C_{1-20}$ alkylene group, which may be branched by an alkyl group, R is a $C_{1-20}$ alkyl group, which may be branched by the alkyl group, and which may be a cycloalkyl group or a cycloalkylalkyl group, and each of X and Y is independently a hydrogen atom, a $C_{1-8}$ alkyl group or a halogen atom.

According to a second embodiment of the present invention, provided is a method for producing a 9,10-bis(alkoxycarbonylalkyleneoxy)anthracene compound having ester groups, represented by the following formula (1), which comprises reacting a 9,10-dihydroxyanthracene compound represented by the following formula (2) and an ester compound represented by the following formula (3):

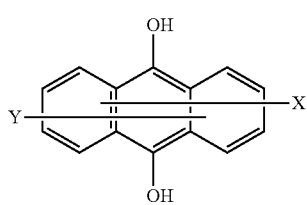

(2)

wherein each of X and Y is independently a hydrogen atom, a $C_{1-8}$ alkyl group or a halogen atom;

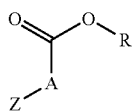

(3)

wherein A is a $C_{1-20}$ alkylene group, which may be branched by an alkyl group, R is a $C_{1-20}$ alkyl group, which may be branched by the alkyl group, which may be a cycloalkyl group or a cycloalkylalkyl group, which may be substituted by a hydroxy group, and of which one or more of carbon atoms may be substituted by an oxygen atom (excluding a case of forming a peroxide), and Z is a chlorine atom, a bromine atom or an iodine atom;

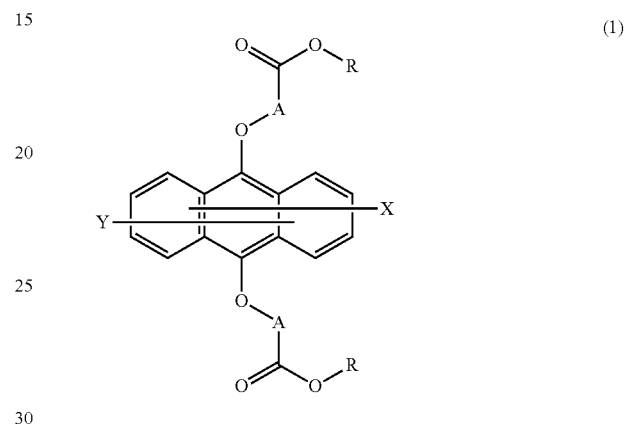

(1)

wherein A is a $C_{1-20}$ alkylene group, which may be branched by an alkyl group, R is a $C_{1-20}$ alkyl group, which may be branched by the alkyl group, which may be a cycloalkyl group or a cycloalkylalkyl group, which may be substituted by a hydroxy group, and of which one or more of carbon atoms may be substituted by an oxygen atom (excluding a case of forming a peroxide), and each of X and Y is independently a hydrogen atom, a $C_{1-8}$ alkyl group or a halogen atom.

According to a third embodiment of the present invention, provided is a method for producing a 9,10-bis(alkoxycarbonylalkyleneoxy)anthracene compound having ester groups, represented by the following formula (1), which comprises reducing a 9,10-anthraquinone compound represented by the following formula (9) to obtain a 9,10-dihydroxyanthracene compound represented by the following formula (2), and reacting the 9,10-dihydroxyanthracene compound represented by the formula (2) and an ester compound represented by the following formula (3):

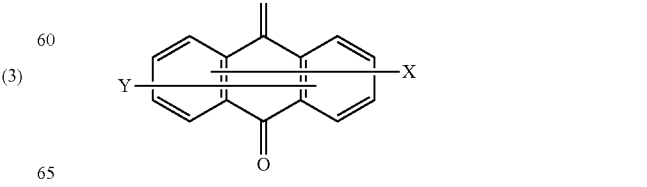

(9)

wherein each of X and Y is independently a hydrogen atom, a $C_{1-8}$ alkyl group or a halogen atom;

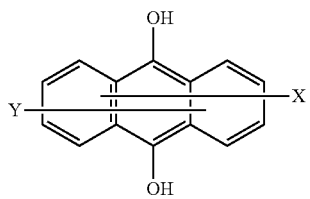
(2)

wherein each of X and Y is independently a hydrogen atom, a $C_{1-8}$ alkyl group or a halogen atom;

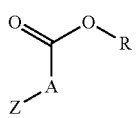
(3)

wherein A is a $C_{1-20}$ alkylene group, which may be branched by an alkyl group, R is a $C_{1-20}$ alkyl group, which may be branched by the alkyl group, which may be a cycloalkyl group or a cycloalkylalkyl group, which may be substituted by a hydroxy group, and of which one or more of carbon atoms may be substituted by an oxygen atom (excluding a case of forming a peroxide), and Z is a chlorine atom, a bromine atom or an iodine atom;

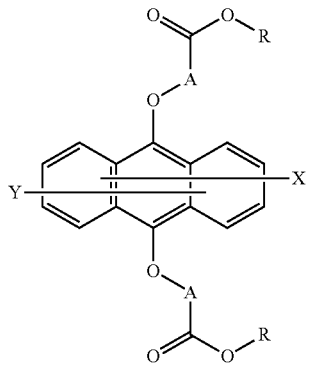
(1)

wherein A is a $C_{1-20}$ alkylene group, which may be branched by an alkyl group, R is a $C_{1-20}$ alkyl group, which may be branched by the alkyl group, which may be a cycloalkyl group or a cycloalkylalkyl group, which may be substituted by a hydroxy group, and of which one or more of carbon atoms may be substituted by an oxygen atom (excluding a case of forming a peroxide), and each of X and Y is independently a hydrogen atom, a $C_{1-8}$ alkyl group or a halogen atom.

According to a fourth embodiment of the present invention, provided is a method for producing a 9,10-bis(alkoxycarbonylalkyleneoxy)anthracene compound having ester groups, represented by the following formula (1), which comprises reacting a 9,10-dihydroxyanthracene compound represented by the following formula (2) and a carboxylic acid compound represented by the following formula (4) to prepare a 9,10-bis(hydroxycarbonylalkyleneoxy)anthracene compound represented by the following formula (5), and reacting the 9,10-bis(hydroxycarbonylalkyleneoxy)anthracene compound represented by the formula (5) and an esterifying agent represented by the following formula (6), (7) or (8):

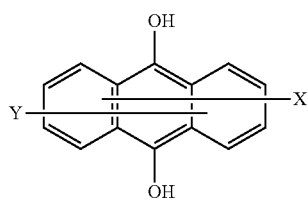
(2)

wherein each of X and Y is independently a hydrogen atom, a $C_{1-8}$ alkyl group or a halogen atom;

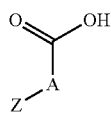
(4)

wherein A is a $C_{1-20}$ alkylene group, which may be branched by an alkyl group, and Z is a chlorine atom, a bromine atom or an iodine atom;

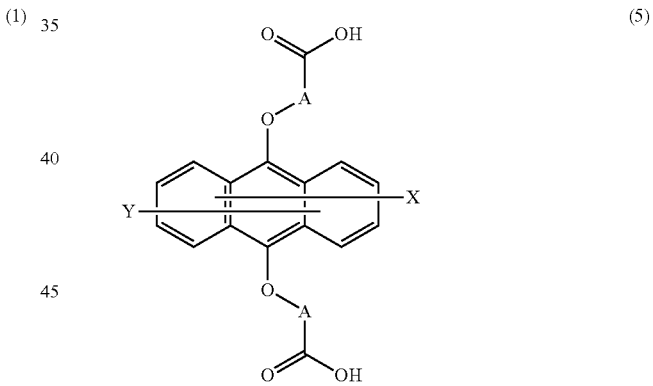
(5)

wherein A is a $C_{1-20}$ alkylene group, which may be branched by an alkyl group, and each of X and Y is independently a hydrogen atom, a $C_{1-8}$ alkyl group or a halogen atom;

R—OH (6)

wherein R is a $C_{1-20}$ alkyl group, which may be branched by the alkyl group, which may be a cycloalkyl group or a cycloalkylalkyl group, which may be substituted by a hydroxy group, and of which one or more of carbon atoms may be substituted by an oxygen atom (excluding a case of forming a peroxide);

R—D (7)

wherein R is a $C_{1-20}$ alkyl group, which may be branched by the alkyl group, which may be a cycloalkyl group or a cycloalkylalkyl group, which may be substituted by a hydroxy group, and of which one or more of carbon atoms may be substituted by an oxygen atom (excluding a case of forming a peroxide), and D is a chlorine atom, a bromine atom or an iodine atom;

(8)

wherein $R^1$ is a hydrogen atom or a $C_{1-17}$ alkyl group, which may be branched by the alkyl group, which may be a cycloalkyl group or a cycloalkylalkyl group, which may be substituted by a hydroxy group, and of which one or more of carbon atoms may be substituted by an oxygen atom (excluding a case of forming a peroxide), provided that when $R^1$ is a $C_{1-17}$ alkyl group, the number of carbon atoms in $R^1$ is smaller by 3 than the number of carbon atoms in R, excluding a case where the number of carbon atoms in R in the formula (1) is from 1 to 3;

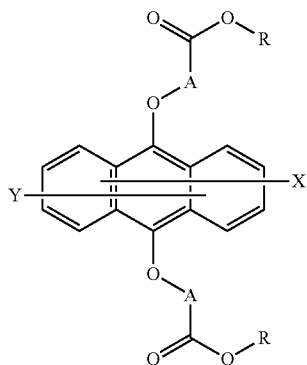
(1)

wherein A is a $C_{1-20}$ alkylene group, which may be branched by an alkyl group, R is a $C_{1-20}$ alkyl group, which may be branched by the alkyl group, which may be a cycloalkyl group or a cycloalkylalkyl group, which may be substituted by a hydroxy group, and of which one or more of carbon atoms may be substituted by an oxygen atom (excluding a case of forming a peroxide), and each of X and Y is independently a hydrogen atom, a $C_{1-8}$ alkyl group or a halogen atom.

According to a fifth embodiment of the present invention, provided is a method for producing a 9,10-bis(alkoxycarbonylalkyleneoxy)anthracene compound having ester groups, represented by the following formula (1), which comprises reducing a 9,10-anthraquinone compound represented by the following formula (9) to obtain a 9,10-dihydroxyanthracene compound represented by the following formula (2), reacting the 9,10-dihydroxyanthracene compound represented by the formula (2) and a carboxylic acid compound represented by the following formula (4) to prepare a 9,10-bis(hydroxycarbonylalkyleneoxy)anthracene compound represented by the following formula (5), and reacting the 9,10-bis(hydroxycarbonylalkyleneoxy)anthracene compound represented by the formula (5) and an esterifying agent represented by the following formula (6), (7) or (8):

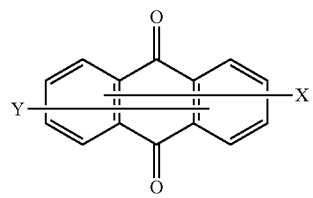
(9)

wherein each of X and Y is independently a hydrogen atom, a $C_{1-8}$ alkyl group or a halogen atom;

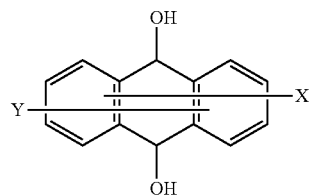
(2)

wherein each of X and Y is independently a hydrogen atom, a $C_{1-8}$ alkyl group or a halogen atom;

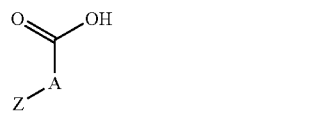
(4)

wherein A is a $C_{1-20}$ alkylene group, which may be branched by an alkyl group, and Z is a chlorine atom, a bromine atom or an iodine atom;

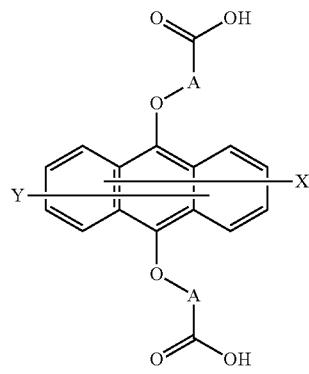
(5)

wherein A is a $C_{1-20}$ alkylene group, which may be branched by an alkyl group, and each of X and Y is independently a hydrogen atom, a $C_{1-8}$ alkyl group or a halogen atom;

R—OH (6)

wherein R is a $C_{1-20}$ alkyl group, which may be branched by the alkyl group, which may be a cycloalkyl group or a cycloalkylalkyl group, which may be substituted by a hydroxy group, and of which one or more of carbon atoms may be substituted by an oxygen atom (excluding a case of forming a peroxide);

$$R—D \qquad (7)$$

wherein R is a $C_{1-20}$ alkyl group, which may be branched by the alkyl group, which may be a cycloalkyl group or a cycloalkylalkyl group, which may be substituted by a hydroxy group, and of which one or more of carbon atoms may be substituted by an oxygen atom (excluding a case of forming a peroxide), and D is a chlorine atom, a bromine atom or an iodine atom;

(8)

wherein $R^1$ is a hydrogen atom or a $C_{1-17}$ alkyl group, which may be branched by the alkyl group, which may be a cycloalkyl group or a cycloalkylalkyl group, which may be substituted by a hydroxy group, and of which one or more of carbon atoms may be substituted by an oxygen atom (excluding a case of forming a peroxide), provided that when $R^1$ is a $C_{1-17}$ alkyl group, the number of carbon atoms in $R^1$ is smaller by 3 than the number of carbon atoms in R, excluding a case where the number of carbon atoms in R in the formula (1) is from 1 to 3;

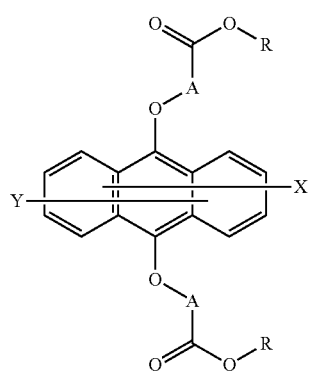

(1)

wherein A is a $C_{1-20}$ alkylene group, which may be branched by an alkyl group, R is a $C_{1-20}$ alkyl group, which may be branched by the alkyl group, which may be a cycloalkyl group or a cycloalkylalkyl group, which may be substituted by a hydroxy group, and of which one or more of carbon atoms may be substituted by an oxygen atom (excluding a case of forming a peroxide), and each of X and Y is independently a hydrogen atom, a $C_{1-8}$ alkyl group or a halogen atom.

According to a sixth embodiment of the present invention, provided is a photopolymerization sensitizer containing a 9,10-bis(alkoxycarbonylalkyleneoxy)anthracene compound having ester groups, represented by the following formula (1):

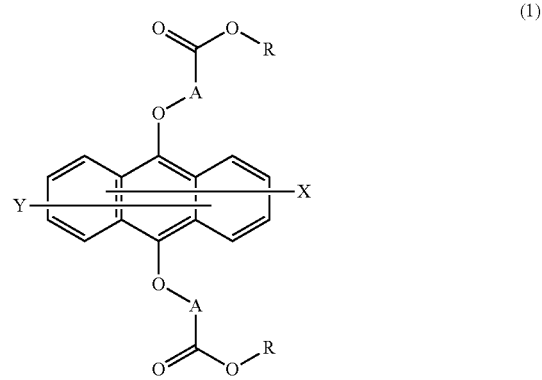

(1)

wherein A is a $C_{1-20}$ alkylene group, which may be branched by an alkyl group, R is a $C_{1-20}$ alkyl group, which may be branched by the alkyl group, which may be a cycloalkyl group or a cycloalkylalkyl group, which may be substituted by a hydroxy group, and of which one or more of carbon atoms may be substituted by an oxygen atom (excluding a case of forming a peroxide), and each of X and Y is independently a hydrogen atom, a $C_{1-8}$ alkyl group or a halogen atom.

According to a seventh embodiment of the present invention, provided is the photopolymerization sensitizer according to the sixth embodiment, wherein in the 9,10-bis(alkoxycarbonylalkyleneoxy)anthracene compound having ester groups, represented by the formula (1), R is a $C_{1-20}$ alkyl group, which is not substituted by a hydroxy group, and of which the carbon atom is not substituted by an oxygen atom.

According to an eighth embodiment of the present invention, provided is the photopolymerization sensitizer according to the sixth or seventh embodiment, wherein in the 9,10-bis(alkoxycarbonylalkyleneoxy)anthracene corn pound having ester groups, represented by the formula (1), A is a $C_1$ alkylene group.

According to a ninth embodiment of the present invention, provided is a photopolymerization initiator composition comprising the photopolymerization sensitizer as defined in any one of the sixth to eighth embodiment, and a photopolymerization initiator.

According to a tenth embodiment of the present invention, provided is a photopolymerizable corn position comprising the photopolymerization initiator composition as defined in the ninth embodiment and a photocationic polymerizable compound.

According to an eleventh embodiment of the present invention, provided is a photopolymerizable corn position comprising the photopolymerization initiator composition as defined in the ninth embodiment and a photoradical polymerizable compound.

According to a twelfth embodiment of the present invention, provided is a polymerization method of polymerizing the photopolymerizable corn position as defined in the tenth or eleventh embodiment by applying energy rays including light having a wavelength within a range of from 300 nm to 500 nm.

According to a thirteenth embodiment of the present invention, provided is the polymerization method according to the twelfth embodiment, wherein an irradiation source of the energy rays including light having a wavelength within a range of from 300 nm to 500 nm is an ultraviolet LED or a semiconductor laser having a center wavelength of 365 nm, 375 nm, 385 nm, 395 nm or 405 nm.

Advantageous Effects of Invention

The 9,10-bis(alkoxycarbonylalkyleneoxy)anthracene compound having ester groups of the present invention is a useful compound not only in having high effects as a photopolymerization sensitizer in photopolymerization reaction but also in that in a photopolymerizable composition containing the compound of the present invention as a photopolymerization sensitizer, the degree of migration or blooming of the photopolymerization sensitizer is very low. In its production, it can be produced at a low cost with an easy process without using an oxidized alkylene compound which is hardly available and is difficult to handle.

The objects, characteristics and advantages of the present invention will become more apparent by the following detailed description.

DESCRIPTION OF EMBODIMENTS (Compound)

The 9,10-bis(alkoxycarbonylalkyleneoxy)anthracene compound having ester groups of the present invention is a compound represented by the following formula (1):

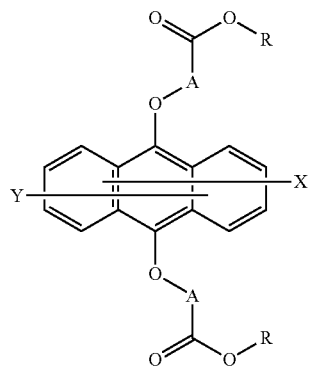

wherein A is a $C_{1-20}$ alkylene group, which may be branched by an alkyl group, R is a $C_{1-20}$ alkyl group, which may be branched by the alkyl group, which may be a cycloalkyl group or a cycloalkylalkyl group, which may be substituted by a hydroxy group, and of which one or more of carbon atoms may be substituted by an oxygen atom (excluding a case of forming a peroxide), and each of X and Y is independently a hydrogen atom, a $C_{1-8}$ alkyl group or a halogen atom.

In the formula (1), the $C_{1-20}$ alkylene group represented by A may, for example, be a methylene group, an ethylene group, a propylene group, a butylene group, a pentylene group, a hexylene group, a heptylene group, an octylene group, a nonylene group, a decylene group, an undecylene group, a dodecylene group, a tridodecylene group, a tetradecylene group, a pentadecylene group, a hexadecylene group, a heptadecylene group, an octadecylene group, a nonadecylene group or an eicosylene group, and the alkylene group may be branched by an alkyl group.

In the formula (1), the $C_{1-8}$ alkyl group represented by X or Y may, for example, be a methyl group, an ethyl group, an n-propyl group, an i-propyl group, an n-butyl group, an i-butyl group, an n-pentyl group, an i-pentyl group, an n-hexyl group, an n-heptyl group, an n-octyl group or a 2-ethylhexyl group, and the halogen atom may, for example, be a fluorine atom, a chorine atom, a bromine atom or an iodine atom.

In the formula (1), the $C_{1-20}$ alkyl group represented by R may, for example, be a methyl group, an ethyl group, an n-propyl group, an i-propyl group, an n-butyl group, an i-butyl group, a t-butyl group, an n-pentyl group, an i-pentyl group, an n-hexyl group, an n-heptyl group, an n-octyl group, a 2-ethylhexyl group, an n-nonyl group, an n-decyl group, an n-undecyl group, an n-dodecyl group, an n-tridecyl group, an n-tetradecyl group, an n-pentadecyl group, an n-hexadecyl group, an n-heptadecyl group, an n-octadecyl group, an n-nonadecyl group or an n-eicosyl group, and the alkyl group substituted by a hydroxy group may, for example, be a 2-hydroxyethyl group, a 2-hydroxypropyl group, a 3-hydroxypropyl group, a 2-hydroxybutyl group, a 3-hydroxybutyl group, a 4-hydroxybutyl group, a 5-hydroxypentyl group, a 6-hydroxyhexyl group, a 7-hydroxyheptyl group, a 8-hydroxyoctyl group, a 6-hydroxy-2-ethylhexyl group, a 9-hydroxynonyl group, a 10-hydroxydecyl group, a 11-hydroxyundecyl group, a 12-hydroxydodecyl group, a 2-hydroxy-3-methoxypropyl group, a 2-hydroxy-3-ethoxypropyl group, a 2-hydroxy-3-propoxypropyl group, a 2-hydroxy-3-butoxypropyl group, a 2-hydroxy-3-pentyloxypropyl group, a 2-hydroxy-3-hexyloxypropyl group, a 2-hydroxy-3-octyloxypropyl group, a 2-hydroxy-3-(2-ethylhexyloxy)propyl group, a 2,3-dihydroxypropyl group, a 2-hydroxy-3-allyloxypropyl group or a 2-hydroxy-3-methallyloxypropyl group. The cycloalkyl group may, for example, be a cyclopropyl group, a cyclobutyl group, a cyclopentyl group, a cyclohexyl group, a cycloheptyl group, a cyclooctyl group, a norbornyl group, an adamantyl group, a 4-n-dodecylcyclohexyl group, a decahydronaphthyl group or a hydroxycyclohexyl group, and the cycloalkylalkyl group may, for example, be a cyclopropylmethyl group, a cyclobutylmethyl group, a cyclopentylmethyl group, a cyclohexylmethyl group, a cycloheptylmethyl group, a cyclooctylmethyl group, a cyclononylmethyl group, a cyclodecylmethyl group, a 2-cyclobutylethyl group, a 2-cyclopentylethyl group, a 2-cyclohexylethyl group, a 2-cycloheptylethyl group, a 2-cyclooctylethyl group, a 2-cyclononylethyl group, a 2-cyclodecylethyl group, a 3-cyclobutylpropyl group, a 3-cyclopentylpropyl group, a 3-cyclohexylpropyl group, a 3-cycloheptylpropyl group, a 3-cyclooctylpropyl group, a 3-cyclononylpropyl group, a 3-cyclodecylpropyl group, a 4-cyclobutylbutyl group, a 4-cyclopentylbutyl group, a 4-cyclohexylbutyl group, a 4-cycloheptylbutyl group, a 4-cyclooctylbutyl group, a 4-cyclononylbutyl group, a 4-cyclodecylbutyl group, a 3-3-adamantylpropyl group or a decahydronaphthylpropyl group.

Specific examples of the 9,10-bis(alkoxycarbonylalkyleneoxy)anthracene compound having ester groups represented by the formula (1) of the present invention include 9,10-bis(methoxycarbonylmethyleneoxy)anthracene, 9,10-bis(ethoxycarbonylmethyleneoxy)anthracene, 9,10-bis(n-propoxycarbonylmethyleneoxy)anthracene, 9,10-bis(iso-propoxycarbonylmethyleneoxy)anthracene, 9,10-bis(tert-butoxycarbonylmethyleneoxy)anthracene, 9,10-bis(n-butoxycarbonylmethyleneoxy)anthracene, 9,10-bis(n- pentyloxycarbonylmethyleneoxy)anthracene, 9,10-bis(methoxycarbonylpropyleneoxy)anthracene, 9,10-bis(ethoxycarbonylpropyleneoxy)anthracene, 9,10-bis(isopropoxycarbonylpropyleneoxy)anthracene, 9,10-bis(tert-butoxycarbonylpropyleneoxy)anthracene, 9,10-bis(n-butoxycarbonylpropyleneoxy)anthracene, 9,10-bis(methoxycarbonylmethylmethyleneoxy)anthracene, 9,10-bis(ethoxycarbonylmethylmethyleneoxy)anthracene, 9,10-bis(ethoxycarbonylethylmethyleneoxy)anthracene, 9,10-bis(isopropoxycarbonylmethylmethyleneoxy)anthracene, 9,10-bis(tert-butoxycarbonylmethylmethyleneoxy)anthracene, 9,10-bis(n-butoxycarbonylmethylmethyleneoxy)anthracene, 9,10-bis(methoxycarbonylbutyleneoxy)anthracene, 9,10-bis(ethoxycarbonylbutyleneoxy)anthracene, 9,10-bis(isopropoxycarbonylbutyleneoxy)anthracene, 9,10-bis(tert-butoxycarbonylbutyleneoxy)anthracene, 9,10-bis(n-butoxycarbonylbutyleneoxy)anthracene, 9,10-bis(2-hydroxyethoxycarbonylmethyleneoxy)anthracene, 9,10-bis(cyclohexyloxycarbonylmethyleneoxy)anthracene, 9,10-bis(cyclohexylmethyloxycarbonylmethyleneoxy)anthracene and 9,10-bis(norbornyloxycarbonylmethyleneoxy)anthracene.

Further, 9,10-bis(methoxycarbonylpentyleneoxy)anthracene, 9,10-bis(ethoxycarbonylpentyleneoxy)anthracene, 9,10-bis(isopropoxycarbonylpentyleneoxy)anthracene, 9,10-bis(tert-butoxycarbonylpentyleneoxy)anthracene, 9,10-bis(n-butoxycarbonylpentyleneoxy)anthracene, 9,10-bis(methoxycarbonylhexyleneoxy)anthracene, 9,10-bis(ethoxycarbonylhexyleneoxy)anthracene, 9,10-bis(isopropoxycarbonylhexyleneoxy)anthracene, 9,10-bis(tert-butoxycarbonylhexyleneoxy)anthracene, 9,10-bis(n-butoxycarbonylhexyleneoxy)anthracene, 9,10-bis(methoxycarbonylheptyleneoxy)anthracene, 9,10-bis(ethoxycarbonylheptyleneoxy)anthracene, 9,10-bis(isopropoxycarbonylheptyleneoxy)anthracene, 9,10-bis(tert-butoxycarbonylheptyleneoxy)anthracene, 9,10-bis(n-butoxycarbonylheptyleneoxy)anthracene, 9,10-bis(methoxycarbonyloctyleneoxy)anthracene, 9,10-bis(ethoxycarbonyloctyleneoxy)anthracene, 9,10-bis(isopropoxycarbonyloctyleneoxy)anthracene, 9,10-bis(tert-butoxycarbonyloctyleneoxy)anthracene, 9,10-bis(n-butoxycarbonyloctyleneoxy)anthracene, 9,10-bis(methoxycarbonylnonyleneoxy)anthracene, 9,10-bis(ethoxycarbonylnonyleneoxy)anthracene, 9,10-bis(isopropoxycarbonylnonyleneoxy)anthracene, 9,10-bis(tert-butoxycarbonylnonyleneoxy)anthracene, 9,10-bis(n-butoxycarbonylnonyleneoxy)anthracene, 9,10-bis(methoxycarbonyldecyleneoxy)anthracene, 9,10-bis(ethoxycarbonyldecyleneoxy)anthracene, 9,10-bis(isopropoxycarbonyldecyleneoxy)anthracene, 9,10-bis(tert-butoxycarbonyldecyleneoxy)anthracene, 9,10-bis(n-butoxycarbonyldecyleneoxy)anthracene, 9,10-bis(methoxycarbonylundecyleneoxy)anthracene, 9,10-bis(ethoxycarbonylundecyleneoxy)anthracene, 9,10-bis(isopropoxycarbonylundecyleneoxy)anthracene, 9,10-bis(tert-butoxycarbonylundecyleneoxy)anthracene, 9,10-bis(n-butoxycarbonylundecyleneoxy)anthracene, 9,10-bis(methoxycarbonyldodecyleneoxy)anthracene, 9,10-bis(ethoxycarbonyldodecyleneoxy)anthracene, 9,10-bis(isopropoxycarbonyldodecyleneoxy)anthracene, 9,10-bis(tert-butoxycarbonyldodecyleneoxy)anthracene, 9,10-bis(n-butoxycarbonyldodecyleneoxy)anthracene, 9,10-bis(methoxycarbonyltridecyleneoxy)anthracene, 9,10-bis(ethoxycarbonyltridecyleneoxy)anthracene, 9,10-bis(isopropoxycarbonyltridecyleneoxy)anthracene, 9,10-bis(tert-butoxycarbonyltridecyleneoxy)anthracene, 9,10-bis(n-butoxycarbonyltridecyleneoxy)anthracene, 9,10-bis(methoxycarbonyltetradecyleneoxy)anthracene, 9,10-bis(ethoxycarbonyltetradecyleneoxy)anthracene, 9,10-bis(isopropoxycarbonyltetradecyleneoxy)anthracene, 9,10-bis(tert-butoxycarbonyltetradecyleneoxy)anthracene, 9,10-bis(n-butoxycarbonyltetradecyleneoxy)anthracene, 9,10-bis(methoxycarbonylpentadecyleneoxy)anthracene, 9,10-bis(ethoxycarbonylpentadecyleneoxy)anthracene, 9,10-bis(isopropoxycarbonylpentadecyleneoxy)anthracene, 9,10-bis(tert-butoxycarbonylpentadecyleneoxy)anthracene, 9,10-bis(n-butoxycarbonylpentadecyleneoxy)anthracene, 9,10-bis(methoxycarbonylhexadecyleneoxy)anthracene, 9,10-bis(ethoxycarbonylhexadecyleneoxy)anthracene, 9,10-bis(isopropoxycarbonylhexadecyleneoxy)anthracene, 9,10-bis(tert-butoxycarbonylhexadecyleneoxy)anthracene, 9,10-bis(n-butoxycarbonylhexadecyleneoxy)anthracene, 9,10-bis(methoxycarbonylheptadecyleneoxy)anthracene, 9,10-bis(ethoxycarbonylheptadecyleneoxy)anthracene, 9,10-bis(isopropoxycarbonylheptadecyleneoxy)anthracene, 9,10-bis(tert-butoxycarbonylheptadecyleneoxy)anthracene, 9,10-bis(n-butoxycarbonylheptadecyleneoxy)anthracene, 9,10-bis(methoxycarbonyloctadecyleneoxy)anthracene, 9,10-bis(ethoxycarbonyloctadecyleneoxy)anthracene, 9,10-bis(isopropoxycarbonyloctadecyleneoxy)anthracene, 9,10-bis(tert-butoxycarbonyloctadecyleneoxy)anthracene, 9,10-bis(n-butoxycarbonyloctadecyleneoxy)anthracene, 9,10-bis(methoxycarbonylnonadecyleneoxy)anthracene, 9,10-bis(ethoxycarbonylnonadecyleneoxy)anthracene, 9,10-bis(isopropoxycarbonylnonadecyleneoxy)anthracene, 9,10-bis(tert-butoxycarbonylnonadecyleneoxy)anthracene, 9,10-bis(n-butoxycarbonylnonadecyleneoxy)anthracene, 9,10-bis(methoxycarbonyleicosyleneoxy)anthracene, 9,10-bis(ethoxycarbonyleicosyleneoxy)anthracene, 9,10-bis(isopropoxycarbonyleicosyleneoxy)anthracene, 9,10-bis(tert-butoxycarbonyleicosyleneoxy)anthracene and 9,10-bis(n-butoxycarbonyleicosyleneoxy)anthracene may, for example, be mentioned.

Specific examples of the 9,10-bis(alkoxycarbonylalkyleneoxy)anthracene compound wherein X and/or Y is an alkyl group, include 2-ethyl-9,10-bis(methoxycarbonylmethyleneoxy)anthracene, 2-ethyl-9,10-bis(ethoxycarbonylmethyleneoxy)anthracene, 2-ethyl-9,10-bis(n-propoxycarbonylmethyleneoxy)anthracene, 2-ethyl-9,10-bis(isopropoxycarbonylmethyleneoxy)anthracene, 2-ethyl-9,10-bis(tert-butoxycarbonylmethyleneoxy)anthracene, 2-ethyl-9,10-bis(n-butoxycarbonylmethyleneoxy)anthracene, 2-ethyl-9,10-bis(n-pentyloxycarbonylmethyleneoxy)anthracene, 2-ethyl-9,10-bis(methoxycarbonylpropyleneoxy)anthracene, 2-ethyl-9,10-bis(ethoxycarbonylpropyleneoxy)anthracene, 2-ethyl-9,10-bis(isopropoxycarbonylpropyleneoxy)anthracene, 2-ethyl-9,10-bis(tert-butoxycarbonylpropyleneoxy)anthracene, 2-ethyl-9,10-bis(n-butoxycarbonylpropyleneoxy)anthracene, 2-ethyl-9,10-bis(methoxycarbonylmethylmethyleneoxy)anthracene, 2-ethyl-9,10-bis(ethoxycarbonylmethylmethyleneoxy)anthracene, 2-ethyl-9,10-bis(ethoxycarbonylethylmethyleneoxy)anthracene, 2-ethyl-9,10-bis(isopropoxycarbonylmethylmethyleneoxy)anthracene, 2-ethyl-9,10-bis(tert-butoxycarbonylmethylmethyleneoxy)anthracene, 2-ethyl-9,10-bis(n-butoxycarbonylmethylmethyleneoxy)anthracene, 2-ethyl-9,10-bis(methoxycarbonylbutyleneoxy)anthracene, 2-ethyl-9,10-bis(ethoxycarbonylbutyleneoxy)anthracene, 2-ethyl-9,10-bis(isopropoxycarbonylbutyleneoxy)anthracene, 2-ethyl-9,10-bis(tert-butoxycarbonylbutyleneoxy)anthracene, 2-ethyl-9,10-bis(n-butoxycarbonylbutyleneoxy)anthracene, 2-ethyl-9,10-bis(methoxycarbonyloctyleneoxy)anthracene, 2-ethyl-9,10-bis(ethoxycarbonyloctyleneoxy)

anthracene, 2-ethyl-9,10-bis(isopropoxycarbonyloctyleneoxy)anthracene, 2-ethyl-9,10-bis(tert-butoxycarbonyloctyleneoxy)anthracene, 2-ethyl-9,10-bis(n-butoxycarbonyloctyleneoxy)anthracene, 2-ethyl-9,10-bis(methoxycarbonylhexadecyleneoxy)anthracene, 2-ethyl-9,10-bis(ethoxycarbonylhexadecyleneoxy)anthracene, 2-ethyl-9,10-bis(isopropoxycarbonylhexadecyleneoxy)anthracene, 2-ethyl-9,10-bis(tert-butoxycarbonylhexadecyleneoxy)anthracene, 2-ethyl-9,10-bis(n-butoxycarbonylhexadecyleneoxy)anthracene, 2-ethyl-9,10-bis(methoxycarbonyleicosyleneoxy)anthracene, 2-ethyl-9,10-bis(ethoxycarbonyleicosyleneoxy)anthracene, 2-ethyl-9,10-bis(isopropoxycarbonyleicosyleneoxy)anthracene, 2-ethyl-9,10-bis(tert-butoxycarbonyleicosyleneoxy)anthracene, 2-ethyl-9,10-bis(n-butoxycarbonyleicosyleneoxy)anthracene, 2-ethyl-9,10-bis(2-hydroxyethoxycarbonylmethyleneoxy)anthracene, 2-ethyl-9,10-bis(cyclohexyloxycarbonylmethyleneoxy)anthracene, 2-ethyl-9,10-bis(cyclohexylmethyloxycarbonylmethyleneoxy)anthracene and 2-ethyl-9,10-bis(norbomyloxycarbonylmethyleneoxy)anthracene.

Further, 2-amyl-9,10-bis(methoxycarbonylmethyleneoxy)anthracene, 2-amyl-9,10-bis(ethoxycarbonylmethyleneoxy)anthracene, 2-amyl-9,10-bis(n-propoxycarbonylmethyleneoxy)anthracene, 2-amyl-9,10-bis(isopropoxycarbonylmethyleneoxy)anthracene, 2-amyl-9,10-bis(tert-butoxycarbonylmethyleneoxy)anthracene, 2-amyl-9,10-bis(n-butoxycarbonylmethyleneoxy)anthracene, 2-amyl-9,10-bis(n-pentyloxycarbonylmethyleneoxy)anthracene, 2-amyl-9,10-bis(methoxycarbonylpropyleneoxy)anthracene, 2-amyl-9,10-bis(ethoxycarbonylpropyleneoxy)anthracene, 2-amyl-9,10-bis(isopropoxycarbonylpropyleneoxy)anthracene, 2-amyl-9,10-bis(tert-butoxycarbonylpropyleneoxy)anthracene, 2-amyl-9,10-bis(n-butoxycarbonylpropyleneoxy)anthracene, 2-amyl-9,10-bis(methoxycarbonylmethylmethyleneoxy)anthracene, 2-amyl-9,10-bis(ethoxycarbonylmethylmethyleneoxy)anthracene, 2-amyl-9,10-bis(ethoxycarbonylethylmethyleneoxy)anthracene, 2-amyl-9,10-bis(isopropoxycarbonylmethylmethyleneoxy)anthracene, 2-amyl-9,10-bis(tert-butoxycarbonylmethylmethyleneoxy)anthracene, 2-amyl-9,10-bis(n-butoxycarbonylmethylmethyleneoxy)anthracene, 2-amyl-9,10-bis(methoxycarbonylbutyleneoxy)anthracene, 2-amyl-9,10-bis(ethoxycarbonylbutyleneoxy)anthracene, 2-amyl-9,10-bis(isopropoxycarbonylbutyleneoxy)anthracene, 2-amyl-9,10-bis(tert-butoxycarbonylbutyleneoxy)anthracene, 2-amyl-9,10-bis(n-butoxycarbonylbutyleneoxy)anthracene, 2-amyl-9,10-bis(2-hydroxyethoxycarbonylmethyleneoxy)anthracene, 2-amyl-9,10-bis(cyclohexyloxycarbonylmethyleneoxy)anthracene, 2-amyl-9,10-bis(cyclohexylmethyloxycarbonylmethyleneoxy)anthracene and 2-amyl-9,10-bis(norbornyloxycarbonylmethyleneoxy)anthracene may, for example, be mentioned.

Specific examples of the 9,10-bis(alkoxycarbonylalkyleneoxy)anthracene compound wherein X and/or Y is a halogen atom, include 2-chloro-9,10-bis(methoxycarbonylmethyleneoxy)anthracene, 2-chloro-9,10-bis(ethoxycarbonylmethyleneoxy)anthracene, 2-chloro-9,10-bis(n-propoxycarbonylmethyleneoxy)anthracene, 2-chloro-9,10-bis(isopropoxycarbonylmethyleneoxy)anthracene, 2-chloro-9,10-bis(tert-butoxycarbonylmethyleneoxy)anthracene, 2-chloro-9,10-bis(n-butoxycarbonylmethyleneoxy)anthracene, 2-chloro-9,10-bis(methoxycarbonylpropyleneoxy)anthracene, 2-chloro-9,10-bis(ethoxycarbonylpropyleneoxy)anthracene, 2-chloro-9,10-bis(isopropoxycarbonylpropyleneoxy)anthracene, 2-chloro-9,10-bis(tert-butoxycarbonylpropyleneoxy)anthracene, 2-chloro-9,10-bis(n-butoxycarbonylpropyleneoxy)anthracene, 2-chloro-9,10-bis(n-pentyloxycarbonylmethyleneoxy)anthracene, 2-chloro-9,10-bis(methoxycarbonylmethylmethyleneoxy)anthracene, 2-chloro-9,10-bis(ethoxycarbonylmethylmethyleneoxy)anthracene, 2-chloro-9,10-bis(ethoxycarbonylethylmethyleneoxy)anthracene, 2-chloro-9,10-bis(isopropoxycarbonylmethylmethyleneoxy)anthracene, 2-chloro-9,10-bis(tert-butoxycarbonylmethylmethyleneoxy)anthracene, 2-chloro-9,10-bis(n-butoxycarbonylmethylmethyleneoxy)anthracene, 2-chloro-9,10-bis(methoxycarbonylbutyleneoxy)anthracene, 2-chloro-9,10-bis(ethoxycarbonylbutyleneoxy)anthracene, 2-chloro-9,10-bis(isopropoxycarbonylbutyleneoxy)anthracene, 2-chloro-9,10-bis(tert-butoxycarbonylbutyleneoxy)anthracene, 2-chloro-9,10-bis(n-butoxycarbonylbutyleneoxy)anthracene, 2-chloro-9,10-bis(methoxycarbonyloctyleneoxy)anthracene, 2-chloro-9,10-bis(ethoxycarbonyloctyleneoxy)anthracene, 2-chloro-9,10-bis(isopropoxycarbonyloctyleneoxy)anthracene, 2-chloro-9,10-bis(tert-butoxycarbonyloctyleneoxy)anthracene, 2-chloro-9,10-bis(n-butoxycarbonyloctyleneoxy)anthracene, 2-chloro-9,10-bis(methoxycarbonylhexadecyleneoxy)anthracene, 2-chloro-9,10-bis(ethoxycarbonylhexadecyleneoxy)anthracene, 2-chloro-9,10-bis(isopropoxycarbonylhexadecyleneoxy)anthracene, 2-chloro-9,10-bis(tert-butoxycarbonylhexadecyleneoxy)anthracene, 2-chloro-9,10-bis(n-butoxycarbonylhexadecyleneoxy)anthracene, 2-chloro-9,10-bis(methoxycarbonyleicosyleneoxy)anthracene, 2-chloro-9,10-bis(ethoxycarbonyleicosyleneoxy)anthracene, 2-chloro-9,10-bis(isopropoxycarbonyleicosyleneoxy)anthracene, 2-chloro-9,10-bis(tert-butoxycarbonyleicosyleneoxy)anthracene, 2-chloro-9,10-bis(n-butoxycarbonyleicosyleneoxy)anthracene, 2-chloro-9,10-bis(2-hydroxyethoxycarbonylmethyleneoxy)anthracene, 2-chloro-9,10-bis(cyclohexyloxycarbonylmethyleneoxy)anthracene, 2-chloro-9,10-bis(cyclohexylmethyloxycarbonylmethyleneoxy)anthracene and 2-chloro-9,10-bis(norbomyloxycarbonylmethyleneoxy)anthracene.

Among the above-mentioned specific examples, in view of productivity, preferred are 9,10-bis(methoxycarbonylmethyleneoxy)anthracene, 9,10-bis(ethoxycarbonylmethyleneoxy)anthracene, 9,10-bis(n-propoxycarbonylmethyleneoxy)anthracene, 9,10-bis(isopropoxycarbonylmethyleneoxy)anthracene, 9,10-bis(tert-butoxycarbonylmethyleneoxy)anthracene, 9,10-bis(n-butoxycarbonylmethyleneoxy)anthracene, 9,10-bis(n-pentyloxycarbonylmethyleneoxy)anthracene, 9,10-bis(cyclohexyloxycarbonylmethyleneoxy)anthracene, 9,10-bis(methoxycarbonylpropyleneoxy)anthracene, 9,10-bis(ethoxycarbonylpropyleneoxy)anthracene, 9,10-bis(isopropoxycarbonylpropyleneoxy)anthracene, 9,10-bis(tert-butoxycarbonylpropyleneoxy)anthracene, 9,10-bis(n-butoxycarbonylpropyleneoxy)anthracene, 9,10-bis(methoxycarbonylmethylmethyleneoxy)anthracene, 9,10-bis(ethoxycarbonylmethylmethyleneoxy)anthracene, 9,10-bis(ethoxycarbonylethylmethyleneoxy)anthracene, 9,10-bis(isopropoxycarbonylmethylmethyleneoxy)anthracene, 9,10-bis(tert-butoxycarbonylmethylmethyleneoxy)anthracene, 9,10-bis(n-butoxycarbonylmethylmethyleneoxy)anthracene, 9,10-bis(methoxycarbonylbutyleneoxy)anthracene, 9,10-bis(ethoxycarbonylbutyleneoxy)anthracene, 9,10-bis(isopropoxycarbonylbutyleneoxy)anthracene, 9,10-bis(tert-butoxycarbonylbutyleneoxy)anthracene, 9,10-bis(n-butoxycarbonylbutyleneoxy)anthracene, 9,10-bis(2- hydroxyethoxycarbonylmethyleneoxy)anthracene, 2-ethyl-9,10-bis(methoxycarbonylmethyleneoxy)anthracene, 2-ethyl-9,10-bis(ethoxycarbonylmethyleneoxy)anthracene, 2-ethyl-9,10-bis(n-propoxycarbonylmethyleneoxy)anthracene, 2-ethyl-9,10-bis(isopropoxycarbonylmethyleneoxy) anthracene, 2-ethyl-9,10-bis(tert-butoxycarbonylmethyleneoxy)anthracene, 2-ethyl-9,10-bis(n-butoxycarbonylmethyleneoxy)anthracene, 2-ethyl-9,10-bis (methoxycarbonylpropyleneoxy)anthracene, 2-ethyl-9,10-bis(ethoxycarbonylpropyleneoxy)anthracene, 2-ethyl-9,10-bis(isopropoxycarbonylpropyleneoxy)anthracene, 2-ethyl-9,10-bis(tert-butoxycarbonylpropyleneoxy)anthracene, 2-ethyl-9,10-bis(n-butoxycarbonylpropyleneoxy)anthracene, 2-ethyl-9,10-bis(methoxycarbonylmethylmethyleneoxy)anthracene, 2-ethyl-9,10-bis(ethoxycarbonylmethylmethyleneoxy)anthracene, 2-ethyl-9,10-bis (ethoxycarbonylethylmethyleneoxy)anthracene, 2-ethyl-9,10-bis(isopropoxycarbonylmethylmethyleneoxy) anthracene, 2-ethyl-9,10-bis(tert-butoxycarbonylmethylmethyleneoxy)anthracene, 2-ethyl-9,10-bis(n-butoxycarbonylmethylmethyleneoxy)anthracene and 2-ethyl-9,10-bis(2-hydroxyethoxycarbonylmethyleneoxy)anthracene, and particularly preferred are 9,10-bis (methoxycarbonylmethyleneoxy)anthracene (1-1), 9,10-bis (ethoxycarbonylmethyleneoxy)anthracene (1-2), 9,10-bis(n-propoxycarbonylmethyleneoxy)anthracene (1-10), 9,10-bis (isopropoxycarbonylmethyleneoxy)anthracene (1-3), 9,10-bis(tert-butoxycarbonylmethyleneoxy)anthracene (1-4), 9,10-bis(n-butoxycarbonylmethyleneoxy)anthracene (1-5), 9,10-bis(n-pentyloxycarbonylmethyleneoxy)anthracene (1-11), 9,10-bis(methoxycarbonylmethylmethyleneoxy)anthracene (1-6), 9,10-bis(ethoxycarbonylpropyleneoxy)anthracene (1-7), 9,10-bis(ethoxycarbonylbutyleneoxy)anthracene (1-8), 2-ethyl-9,10-bis (isopropoxycarbonylmethyleneoxy)anthracene (1-9) and 9,10-bis(cyclohexyloxycarbonylmethyleneoxy)anthracene (1-12), the structural formulae of which are shown below.

Comprehensively considering the productivity, availability of materials and handling efficiency, R in the formula (1) is preferably a $C_{1-20}$ alkyl group containing no oxygen atom. A in the formula (1) is preferably a $C_1$ methylene group. Considering various physical properties such as migration resistance and hydrophobicity, preferred is an alkyl group having at least 3 carbon atoms, and particularly preferred are 9,10-bis(isopropoxycarbonylmethyleneoxy)anthracene (1-3), 9,10-bis(n-pentyloxycarbonylmethyleneoxy)anthracene (1-11) and 9,10-bis(cyclohexyloxycarbonylmethyleneoxy)anthracene (1-12).

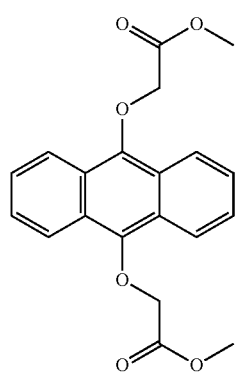

(1-1)

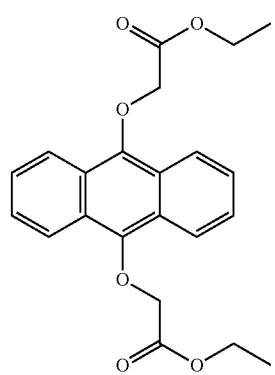

(1-2)

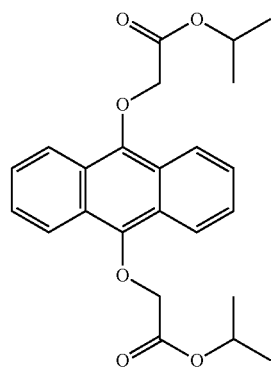

(1-3)

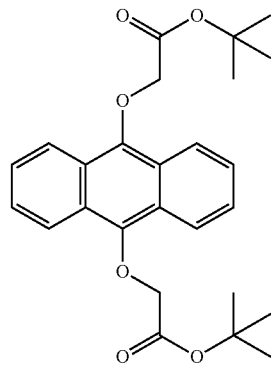

(1-4)

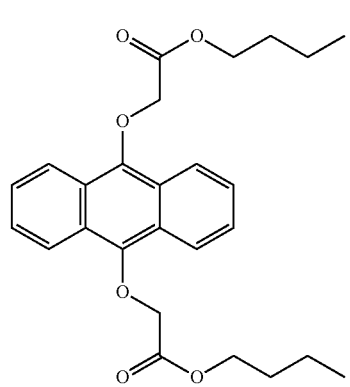

(1-5)

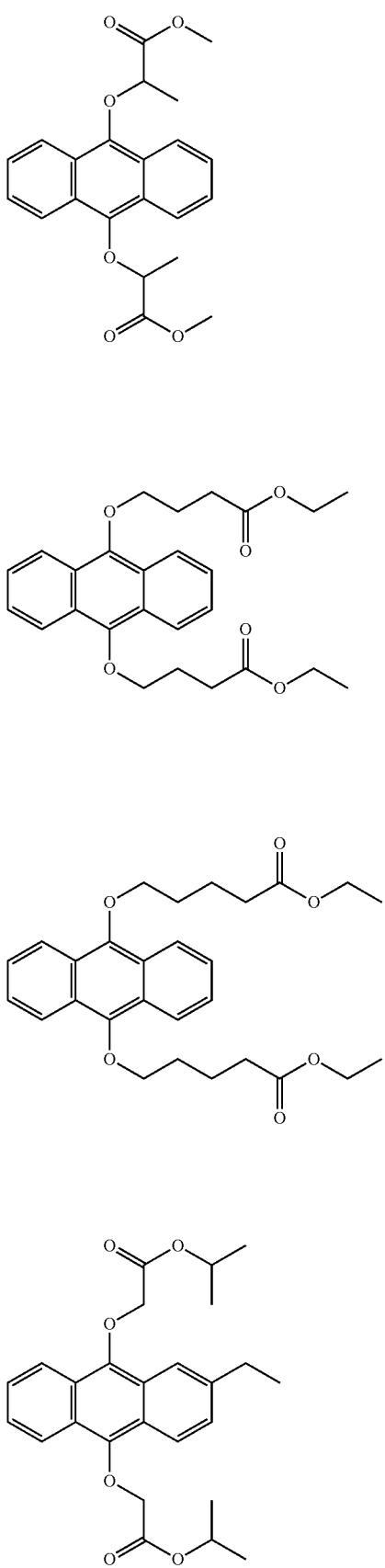
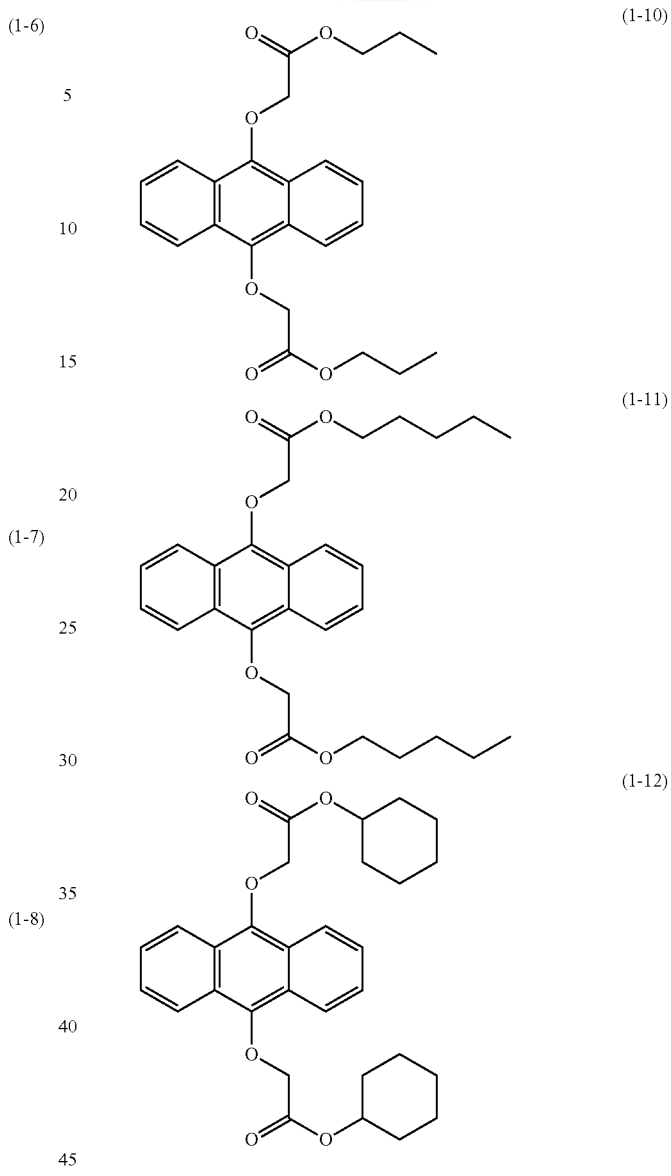

(Production Method)

Now, the method for producing the 9,10-bis(alkoxycarbonylalkyleneoxy)anthracene compound having ester groups of the present invention will be described. The 9,10-bis(alkoxycarbonylalkyleneoxy)anthracene compound having ester groups represented by the formula (1) of the present invention may be prepared by a preparation method using a 9,10-anthraquinone compound represented by the following formula (9) as a starting material or a preparation method using a 9,10-dihydroxyanthracene compound represented by the following formula (2) as a starting material. In the preparation method using the 9,10-anthraquinone compound as a starting material also, the product is prepared via the 9,10-dihydroxyanthracene compound as an intermediate. Further, a preparation method via or using as a starting material the 9,10-dihydroxyanthracene compound in a single step (single step production method) and a preparation method using an intermediate represented by the following formula (5) in two steps (two step production method) may be mentioned.

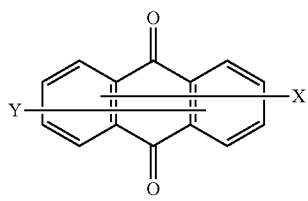

(9)

In the formula (9), each of X and Y is independently a hydrogen atom, a $C_{1-8}$ alkyl group or a halogen atom.

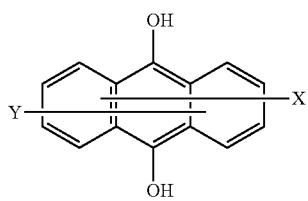

(2)

In the formula (2), each of X and Y is independently a hydrogen atom, a $C_{1-8}$ alkyl group or a halogen atom.

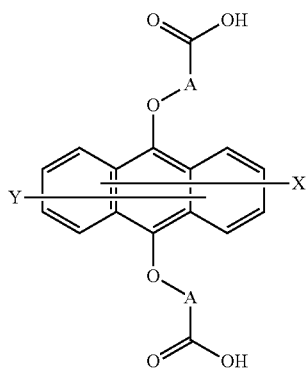

(5)

In the formula (5), A is a $C_{1-20}$ alkylene group, which may be branched by an alkyl group, and each of X and Y is independently a hydrogen atom, a 01-8 alkyl group or a halogen atom.

(Single Step Production Method (1))

Now, the method for preparing the 9,10-bis(alkoxycarbonylalkyleneoxy)anthracene compound having ester groups of the present invention using the 9,10-dihydroxyanthracene compound as a starting material by single step production method will be described. The 9,10-bis(alkoxycarbonylalkyleneoxy)anthracene corn pound having ester groups, represented by the formula (1) of the present invention, may be obtained by reacting the 9,10-dihydroxyanthracene compound represented by the formula (2) with a corresponding ester compound represented by the formula (3) in the presence or in the absence of a basic compound, in accordance with the following Reaction Formula (1).

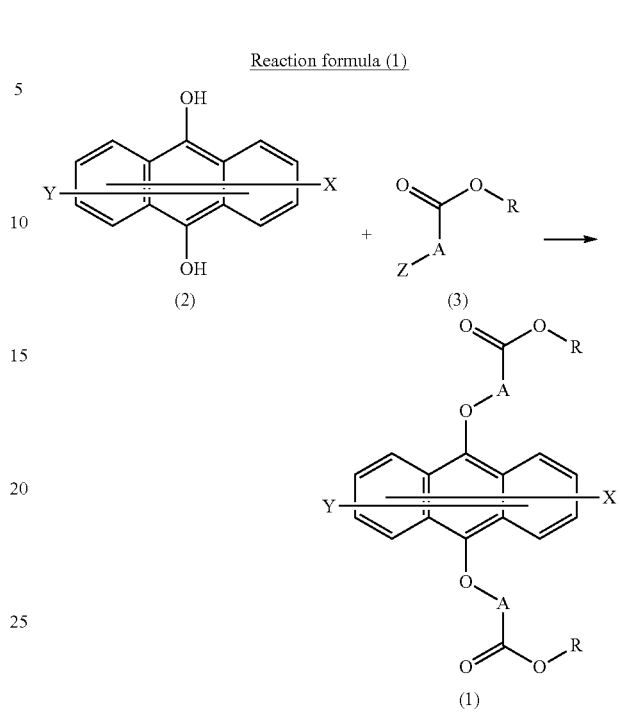

In Reaction formula (1), A is a $C_{1-20}$ alkylene group, which may be branched by an alkyl group. R is a $C_{1-20}$ alkyl group, which may be branched by the alkyl group, which may be a cycloalkyl group or a cycloalkylalkyl group, which may be substituted by a hydroxy group, and of which one or more of carbon atoms may be substituted by an oxygen atom (excluding a case of forming a peroxide). Each of X and Y is independently a hydrogen atom, a $C_{1-8}$ alkyl group or a halogen atom. Z is a chlorine atom, a bromine atom or an iodine atom.

In Reaction formula (1), the 9,10-dihydroxyanthracene compound represented by the formula (2), used as the material, may be obtained by reducing a corresponding 9,10-anthraquinone compound.

The 9,10-dihydroxyanthracene compound used as the material in this reaction may, for example, be specifically 9,10-dihydroxyanthracene, 2-methyl-9,10-dihydroxyanthracene, 2-ethyl-9,10-dihydroxyanthracene, 2-t-pentyl-9,10-dihydroxyanthracene, 2,6-dimethyl-9,10-dihydroxyanthracene, 2-chloro-9,10-dihydroxyanthracene or 2-bromo-9,10-dihydroxyanthracene.

The 9,10-dihydroxyanthracene compound, which is unstable to oxygen, may be used in such a manner that the hydroxy group is protected by a known protecting group.

Further, 9,10-dihydroxyanthracene may be obtained more simply by reducing 9,10-anthraquinone using an alkali metal salt of 1,4,4a,9a-tetrahydroanthraquinone which is a Diels-Alder reaction product of 1,4-naphthoquinone and 1,3-butadiene, or its isomer 1,4-dihydro-9,10-dihydroxyanthracene, as an industrial method. That is, 1,4,4a,9a-tetrahydroanthraquinone obtained by the reaction of 1,4-naphthoquinone and 1,3-butadiene is reacted with 9,10-anthraquinone in an aqueous medium in the presence of an alkaline compound such as an alkali metal hydroxide, whereby an aqueous solution of an alkali metal salt of 9,10-dihydroxyanthracene can be obtained.

The aqueous solution of the alkali metal salt of 9,10-dihydroxyanthracene obtained by this reaction is acidified in the absence of oxygen, whereby precipitates of 9,10-dihydroxyanthracene can be obtained. The precipitates are purified to obtain 9,10-dihydroxyanthracene. A 9,10-dihydroxyanthracene corn pound having a substituent may be obtained in the same manner.

Specific examples of the ester compound represented by the formula (3) used as the material in Reaction formula (1) include methyl chloroacetate, ethyl chloroacetate (3-12), n-propyl chloroacetate, isopropyl chloroacetate, n-butyl chloroacetate (3-5), tert-butyl chloroacetate, pentyl chloroacetate, hexyl chloroacetate, heptyl chloroacetate, octyl chloroacetate, 2-ethylhexyl chloroacetate, nonyl chloroacetate, dodecyl chloroacetate, nonadecyl chloroacetate, eicosyl chloroacetate, cyclohexyl chloroacetate, cyclohexylmethyl chloroacetate, methyl 2-chloropropionate, methyl 3-chloropropionate, methyl 2-chloropropionate, methyl 3-chloropropionate, ethyl 2-chloropropionate, ethyl 3-chloropropionate, n-propyl 2-chloropropionate, n-propyl 3-chloropropionate, isopropyl 2-chloropropionate, isopropyl 3-chloropropionate, n-butyl 2-chloropropionate, n-butyl 3-chloropropionate, tert-butyl 2-chloropropionate, tert-butyl 3-chloropropionate, pentyl 2-chloropropionate, pentyl 3-chloropropionate, hexyl 2-chloropropionate, hexyl 3-chloropropionate, heptyl 2-chloropropionate, heptyl 3-chloropropionate, octyl 2-chloropropionate, octyl 3-chloropropionate, 2-ethylhexyl 2-chloropropionate, 2-ethylhexyl 3-chloropropionate, nonyl 2-chloropropionate, nonyl 3-chloropropionate, dodecyl 2-chloropropionate, dodecyl 3-chloropropionate, nonadecyl 2-chloropropionate, nonadecyl 3-chloropropionate, eicosyl 2-chloropropionate, eicosyl 3-chloropropionate, methyl 2-chlorobutyrate, methyl 3-chlorobutyrate, methyl 4-chlorobutyrate, ethyl 2-chlorobutyrate, ethyl 3-chlorobutyrate, ethyl 4-chlorobutyrate, n-propyl 2-chlorobutyrate, n-propyl 3-chlorobutyrate, n-propyl 4-chlorobutyrate, isopropyl 2-chlorobutyrate, isopropyl 3-chlorobutyrate, isopropyl 4-chlorobutyrate, n-butyl 2-chlorobutyrate, n-butyl 3-chlorobutyrate, n-butyl 4-chlorobutyrate, tert-butyl 2-chlorobutyrate, tert-butyl 3-chlorobutyrate, tert-butyl 4-chlorobutyrate, pentyl 2-chlorobutyrate, pentyl 3-chlorobutyrate, pentyl 4-chlorobutyrate, hexyl 2-chlorobutyrate, hexyl 3-chlorobutyrate, hexyl 4-chlorobutyrate, heptyl 2-chlorobutyrate, heptyl 3-chlorobutyrate, heptyl 4-chlorobutyrate, octyl 2-chlorobutyrate, octyl 3-chlorobutyrate, octyl 4-chlorobutyrate, 2-ethylhexyl 2-chlorobutyrate, 2-ethylhexyl 3-chlorobutyrate, 2-ethylhexyl 4-chlorobutyrate, nonyl 2-chlorobutyrate, nonyl 3-chlorobutyrate, nonyl 4-chlorobutyrate, dodecyl 2-chlorobutyrate, dodecyl 3-chlorobutyrate, dodecyl 4-chlorobutyrate, nonadecyl 2-chlorobutyrate, nonadecyl 3-chlorobutyrate, nonadecyl 4-chlorobutyrate, eicosyl 2-chlorobutyrate, eicosyl 3-chlorobutyrate, eicosyl 4-chlorobutyrate, methyl 2-chlorovalerate, methyl 3-chlorovalerate, methyl 4-chlorovalerate, methyl 5-chlorovalerate, ethyl 2-chlorovalerate, ethyl 3-chlorovalerate, ethyl 4-chlorovalerate, ethyl 5-chlorovalerate, n-propyl 2-chlorovalerate, n-propyl 3-chlorovalerate, n-propyl 4-chlorovalerate, n-propyl 5-chlorovalerate, isopropyl 2-chlorovalerate, isopropyl 3-chlorovalerate, isopropyl 4-chlorovalerate, isopropyl 5-chlorovalerate, n-butyl 2-chlorovalerate, n-butyl 3-chlorovalerate, n-butyl 4-chlorovalerate, n-butyl 5-chlorovalerate, tert-butyl 2-chlorovalerate, tert-butyl 3-chlorovalerate, tert-butyl 4-chlorovalerate, tert-butyl 5-chlorovalerate, pentyl 2-chlorovalerate, pentyl 3-chlorovalerate, pentyl 4-chlorovalerate, pentyl 5-chlorovalerate, hexyl 2-chlorovalerate, hexyl 3-chlorovalerate, hexyl 4-chlorovalerate, hexyl 5-chlorovalerate, heptyl 2-chlorovalerate, heptyl 3-chlorovalerate, heptyl 4-chlorovalerate, heptyl 5-chlorovalerate, octyl 2-chlorovalerate, octyl 3-chlorovalerate, octyl 4-chlorovalerate, octyl 5-chlorovalerate, 2-ethylhexyl 2-chlorovalerate, 2-ethylhexyl 3-chlorovalerate, 2-ethylhexyl 4-chlorovalerate, 2-ethylhexyl 5-chlorovalerate, nonyl 2-chlorovalerate, nonyl 3-chlorovalerate, nonyl 4-chlorovalerate, nonyl 5-chlorovalerate, dodecyl 2-chlorovalerate, dodecyl 3-chlorovalerate, dodecyl 4-chlorovalerate, dodecyl 5-chlorovalerate, nonadecyl 2-chlorovalerate, nonadecyl 3-chlorovalerate, nonadecyl 4-chlorovalerate, nonadecyl 5-chlorovalerate, eicosyl 2-chlorovalerate, eicosyl 3-chlorovalerate, eicosyl 4-chlorovalerate and eicosyl 5-chlorovalerate.

Further, methyl bromoacetate (3-1), ethyl bromoacetate (3-4), n-propyl bromoacetate (3-9), isopropyl bromoacetate (3-2), n-butyl bromoacetate, tert-butyl bromoacetate (3-3), pentyl bromoacetate (3-10), hexyl bromoacetate, heptyl bromoacetate, octyl bromoacetate, 2-ethylhexyl bromoacetate, nonyl bromoacetate, dodecyl bromoacetate, nonadecyl bromoacetate, eicosyl bromoacetate, cyclohexyl bromoacetate (3-11), cyclohexylmethyl bromoacetate, methyl 2-bromopropionate (3-6), methyl 3-bromopropionate, ethyl 2-bromopropionate, ethyl 3-bromopropionate, n-propyl 2-bromopropionate, n-propyl 3-bromopropionate, isopropyl 2-bromopropionate, isopropyl 3-bromopropionate, n-butyl 2-bromopropionate, n-butyl 3-bromopropionate, tert-butyl 2-bromopropionate, tert-butyl 3-bromopropionate, pentyl 2-bromopropionate, pentyl 3-bromopropionate, hexyl 2-bromopropionate, hexyl 3-bromopropionate, heptyl 2-bromopropionate, heptyl 3-bromopropionate, octyl 2-bromopropionate, octyl 3-bromopropionate, 2-ethylhexyl 2-bromopropionate, 2-ethylhexyl 3-bromopropionate, nonyl 2-bromopropionate, nonyl 3-bromopropionate, dodecyl 2-bromopropionate, dodecyl 3-bromopropionate, nonadecyl 2-bromopropionate, nonadecyl 3-bromopropionate, eicosyl 2-bromopropionate, eicosyl 3-bromopropionate, methyl 2-bromobutyrate, methyl 3-bromobutyrate, methyl 4-bromobutyrate, ethyl 2-bromobutyrate, ethyl 3-bromobutyrate, ethyl 4-bromobutyrate (3-7), n-propyl 2-bromobutyrate, n-propyl 3-bromobutyrate, n-propyl 4-bromobutyrate, isopropyl 2-bromobutyrate, isopropyl 3-bromobutyrate, isopropyl 4-bromobutyrate, n-butyl 2-bromobutyrate, n-butyl 3-bromobutyrate, n-butyl 4-bromobutyrate, tert-butyl 2-bromobutyrate, tert-butyl 3-bromobutyrate, tert-butyl 4-bromobutyrate, pentyl 2-bromobutyrate, pentyl 3-bromobutyrate, pentyl 4-bromobutyrate, hexyl 2-bromobutyrate, hexyl 3-bromobutyrate, hexyl 4-bromobutyrate, heptyl 2-bromobutyrate, heptyl 3-bromobutyrate, heptyl 4-bromobutyrate, octyl 2-bromobutyrate, octyl 3-bromobutyrate, octyl 4-bromobutyrate, 2-ethylhexyl 2-bromobutyrate, 2-ethylhexyl 3-bromobutyrate, 2-ethylhexyl 4-bromobutyrate, nonyl 2-bromobutyrate, nonyl 3-bromobutyrate, nonyl 4-bromobutyrate, dodecyl 2-bromobutyrate, dodecyl 3-bromobutyrate, dodecyl 4-bromobutyrate, nonadecyl 2-bromobutyrate, nonadecyl 3-bromobutyrate, nonadecyl 4-bromobutyrate, eicosyl 2-bromobutyrate, eicosyl 3-bromobutyrate, eicosyl 4-bromobutyrate, methyl 2-bromovalerate, methyl 3-bromovalerate, methyl 4-bromovalerate, methyl 5-bromovalerate, ethyl 2-bromovalerate, ethyl 3-bromovalerate, ethyl 4-bromovalerate (3-8), ethyl 5-bromovalerate, n-propyl 2-bromovalerate, n-propyl 3-bromovalerate, n-propyl 4-bromovalerate, n-propyl 5-bromovalerate, isopropyl 2-bromovalerate, isopropyl 3-bromovalerate, isopropyl 4-bromovalerate, isopropyl 5-bromovalerate, n-butyl 2-bromovalerate, n-butyl 3-bromovalerate, n-butyl 4-bromovalerate, n-butyl 5-bromovalerate, tert-butyl 2-bromovalerate, tert-butyl 3-bromovalerate, tert-butyl 4-bromovalerate, tert-butyl 5-bromovalerate, pentyl 2-bromovalerate, pentyl 3-bromovalerate, pentyl 4-bromovalerate, pentyl 5-bromovalerate, hexyl 2-bromovalerate, hexyl 3-bromovalerate, hexyl 4-bromovalerate, hexyl 5-bromovalerate, heptyl 2-bromovalerate, heptyl 3-bromovalerate, heptyl 4-bromovalerate, heptyl 5-bromovalerate, octyl 2-bromovalerate, octyl 3-bromovalerate, octyl 4-bromovalerate, octyl 5-bromovalerate, 2-ethylhexyl 2-bromovalerate, 2-ethylhexyl 3-bromovalerate, 2-ethylhexyl 4-bromovalerate, 2-ethylhexyl 5-bromovalerate, nonyl 2-bromovalerate, nonyl 3-bromovalerate, nonyl 4-bromovalerate, nonyl 5-bromovalerate, dodecyl 2-bromovalerate, dodecyl 3-bromovalerate, dodecyl 4-bromovalerate, dodecyl 5-bromovalerate, nonadecyl 2-bromovalerate, nonadecyl 3-bromovalerate, nonadecyl 4-bromovalerate, nonadecyl 5-bromovalerate, eicosyl 2-bromovalerate, eicosyl 3-bromovalerate, eicosyl 4-bromovalerate, eicosyl 5-bromovalerate, 2-hydroxyethyl bromoacetate (3-10), 2-hydroxyethyl 2-bromopropionate, 2-hydroxyethyl 3-bromobutyrate and 2-hydroxyethyl 4-bromovalerate may, for example, be mentioned.

Further, methyl iodoacetate, ethyl iodoacetate, n-propyl iodoacetate, isopropyl iodoacetate, n-butyl iodoacetate, tert-butyl iodoacetate, pentyl iodoacetate, hexyl iodoacetate, heptyl iodoacetate, octyl iodoacetate, 2-ethylhexyl iodoacetate, nonyl iodoacetate, dodecyl iodoacetate, nonadecyl iodoacetate, eicosyl iodoacetate, methyl 2-iodopropionate, methyl 3-iodopropionate, ethyl 2-iodopropionate, ethyl 3-iodopropionate, n-propyl 2-iodopropionate, n-propyl 3-iodopropionate, isopropyl 2-iodopropionate, isopropyl 3-iodopropionate, n-butyl 2-iodopropionate, n-butyl 3-iodopropionate, tert-butyl 2-iodopropionate, tert-butyl 3-iodopropionate, pentyl 2-iodopropionate, pentyl 3-iodopropionate, hexyl 2-iodopropionate, hexyl 3-iodopropionate, heptyl 2-iodopropionate, heptyl 3-iodopropionate, octyl 2-iodopropionate, octyl 3-iodopropionate, 2-ethylhexyl 2-iodopropionate, 2-ethylhexyl 3-iodopropionate, nonyl 2-iodopropionate, nonyl 3-iodopropionate, dodecyl 2-iodopropionate, dodecyl 3-iodopropionate, nonadecyl 2-iodopropionate, nonadecyl 3-iodopropionate, eicosyl 2-iodopropionate, eicosyl 3-iodopropionate, methyl 2-iodobutyrate, methyl 3-iodobutyrate, methyl 4-iodobutyrate, ethyl 2-iodobutyrate, ethyl 3-iodobutyrate, ethyl 4-iodobutyrate, n-propyl 2-iodobutyrate, n-propyl 3-iodobutyrate, n-propyl 4-iodobutyrate, isopropyl 2-iodobutyrate, isopropyl 3-iodobutyrate, isopropyl 4-iodobutyrate, n-butyl 2-iodobutyrate, n-butyl 3-iodobutyrate, n-butyl 4-iodobutyrate, tert-butyl 2-iodobutyrate, tert-butyl 3-iodobutyrate, tert-butyl 4-iodobutyrate, pentyl 2-iodobutyrate, pentyl 3-iodobutyrate, pentyl 4-iodobutyrate, hexyl 2-iodobutyrate, hexyl 3-iodobutyrate, hexyl 4-iodobutyrate, heptyl 2-iodobutyrate, heptyl 3-iodobutyrate, heptyl 4-iodobutyrate, octyl 2-iodobutyrate, octyl 3-iodobutyrate, octyl 4-iodobutyrate, 2-ethylhexyl 2-iodobutyrate, 2-ethylhexyl 3-iodobutyrate, 2-ethylhexyl 4-iodobutyrate, nonyl 2-iodobutyrate, nonyl 3-iodobutyrate, nonyl 4-iodobutyrate, dodecyl 2-iodobutyrate, dodecyl 3-iodobutyrate, dodecyl 4-iodobutyrate, nonadecyl 2-iodobutyrate, nonadecyl 3-iodobutyrate, nonadecyl 4-iodobutyrate, eicosyl 2-iodobutyrate, eicosyl 3-iodobutyrate, eicosyl 4-iodobutyrate, methyl 2-iodovalerate, methyl 3-iodovalerate, methyl 4-iodovalerate, methyl 5-iodovalerate, ethyl 2-iodovalerate, ethyl 3-iodovalerate, ethyl 4-iodovalerate, ethyl 5-iodovalerate, n-propyl 2-iodovalerate, n-propyl 3-iodovalerate, n-propyl 4-iodovalerate, n-propyl 5-iodovalerate, isopropyl 2-iodovalerate, isopropyl 3-iodovalerate, isopropyl 4-iodovalerate, isopropyl 5-iodovalerate, n-butyl 2-iodovalerate, n-butyl 3-iodovalerate, n-butyl 4-iodovalerate, n-butyl 5-iodovalerate, tert-butyl 2-iodovalerate, tert-butyl 3-iodovalerate, tert-butyl 4-iodovalerate, tert-butyl 5-iodovalerate, pentyl 2-iodovalerate, pentyl 3-iodovalerate, pentyl 4-iodovalerate, pentyl 5-iodovalerate, hexyl 2-iodovalerate, hexyl 3-iodovalerate, hexyl 4-iodovalerate, hexyl 5-iodovalerate, heptyl 2-iodovalerate, heptyl 3-iodovalerate, heptyl 4-iodovalerate, heptyl 5-iodovalerate, octyl 2-iodovalerate, octyl 3-iodovalerate, octyl 4-iodovalerate, octyl 5-iodovalerate, 2-ethylhexyl 2-iodovalerate, 2-ethylhexyl 3-iodovalerate, 2-ethylhexyl 4-iodovalerate, 2-ethylhexyl 5-iodovalerate, nonyl 2-iodovalerate, nonyl 3-iodovalerate, nonyl 4-iodovalerate, nonyl 5-iodovalerate, dodecyl 2-iodovalerate, dodecyl 3-iodovalerate, dodecyl 4-iodovalerate, dodecyl 5-iodovalerate, nonadecyl 2-iodovalerate, nonadecyl 3-iodovalerate, nonadecyl 4-iodovalerate, nonadecyl 5-iodovalerate, eicosyl 2-iodovalerate, eicosyl 3-iodovalerate, eicosyl 4-iodovalerate and eicosyl 5-iodovalerate may, for example, be mentioned.

Among the above mentioned specific examples, chloro compounds and bromo compounds are preferred in view of the reactivity, and compounds of the following formulae are particularly preferred.

(3-1)

(3-2)

(3-3)

(3-4)

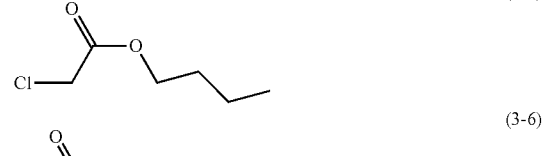

(3-5)

(3-6)

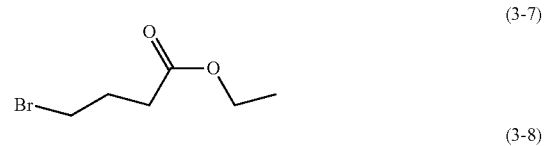

(3-7)

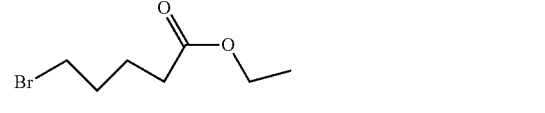

(3-8)

-continued

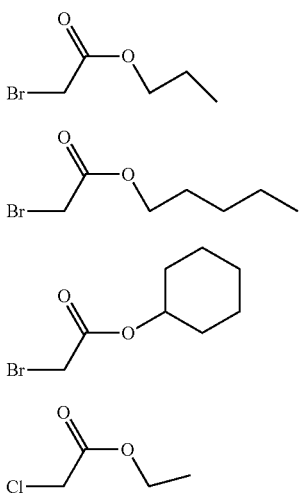

(3-9)
(3-10)
(3-11)
(3-12)

In Reaction formula (1), the amount of the ester compound represented by the formula (3) used is preferably at least 2.0 molar times and less than 10.0 molar times, more preferably at least 2.2 molar times and less than 5.0 molar times, the 9,10-dihydroxyanthracene compound. If it is less than 2.0 molar times, the reaction will not be completed, and if it is 10.0 molar times or more, side-reaction will occur, thus lowering the yield and the purity.

In Reaction formula (1), the ester compound represented by the formula (3) may be a commercial product or may be one prepared from a corresponding carboxylic acid and alcohol.

In Reaction formula (1), in a case where one prepared by corresponding carboxylic acid and alcohol is used as the ester compound represented by the formula (3), it is preferred to preliminarily prepare the ester compound in the system, and to add the 9,10-dihydroxyanthracene compound represented by the formula (2), whereby the reaction can be conducted efficiently.

The basic compound used in Reaction formula (1) may, for example, be sodium hydroxide, potassium hydroxide, sodium hydride, potassium hydride, lithium hexamethyldisilazide, lithium diisopropylamide, triethylamine, tributylamine, trihexylamine, dimethylamine, diethylamine, dipropylamine, dibutylamine, cyclohexylamine, dimethylaniline, pyridine, 4,4-dimethylaminopyridine, piperidine, γ-picoline or lutidine.

The amount of the basic compound added is preferably at least 2.0 molar times and less than 10.0 molar times, more preferably at least 2.2 molar times and less than 5.0 molar times, the 9,10-dihydroxyanthracene compound. If it is less than 2.0 molar times, the reaction will not be completed, and if it is 10.0 molar times or more, side-reaction will occur, thus lowering the yield and the purity.

The reaction is carried out in a solvent or without solvent. The solvent used is not particularly limited so long as it does not react with the ester compound used and may, for example, be an aromatic solvent such as toluene, xylene or ethylbenzene, an ether solvent such as tetrahydrofuran or 1,4-dioxane, a ketone solvent such as acetone, ethyl methyl ketone or methyl isobutyl ketone, or an amide solvent such as dimethylacetoamide or dimethylformamide, a halogenated hydrocarbon solvent such as methylene chloride, ethylene dichloride or chlorobenzene, or an alcohol solvent such as methanol, ethanol or 1-propanol.

In a case where the 9,10-dihydroxyanthracene compound is dissolved in an aqueous solution of an inorganic base and is reacted with the ester, use of a phase transfer catalyst is effective. The phase transfer catalyst may, for example, be tetramethylammonium bromide, tetraethylammonium bromide, tetrapropylammonium bromide, tetrabutylammonium bromide, trioctylmethylammonium bromide, trioctylethylammonium bromide, trioctylpropylammonium bromide, trioctylbutylammonium bromide, benzyldimethyloctadecylammonium bromide, tetramethylammonium chloride, tetraethylammonium chloride, tetrapropylammonium chloride, tetrabutylammonium chloride, trioctylmethylammonium chloride, trioctylethylammonium chloride, trioctylpropylammonium chloride, trioctylbutylammonium chloride or benzyldimethyloctadecylammonium chloride.

The amount of the phase transfer catalyst added is preferably at least 0.01 molar times and less than 1.0 molar times, more preferably at least 0.05 molar times and less than 0.5 molar times, the 9,10-dihydroxyanthracene compound. If it is less than 0.01 molar times, the reaction rate will be low, and if it is at least 1.0 molar times, the purity of the product will decrease.

The reaction temperature of this reaction is usually at least 0° C. and at most 200° C., preferably at least 10° C. and at most 100° C. If it is less than 0° C., the reaction will take too long, and if it exceeds 100° C., impurities tend to increase, and the purity of the desired compound will decrease.

The reaction time of this reaction varies depending upon the reaction temperature and is usually from about 1 hour to about 20 hours. It is preferably from 2 hours to 10 hours.

After completion of the reaction, as the case requires, unreacted raw material, the solvent and the catalyst are removed by washing, by vacuum distillation, by filtration or the like alone or in combination. In a case where the product is a solid, crystals will precipitate during the reaction, which may be subjected to solid-liquid separation by filtration, and as the case requires, recrystallization from a poor solvent such as an alcohol or hexane may be conducted. Otherwise, the crystals may be dried up as they are. In a case where the formed product is a liquid, it is dried up as it is, followed by purification e.g. by distillation as the case requires, to obtain the 9,10-bis(alkoxycarbonylalkyleneoxy)anthracene compound having ester groups.

(Two Step Production Method (1))

Now, the method for preparing the 9,10-bis(alkoxycarbonylalkyleneoxy)anthracene compound having ester groups of the present invention using the 9,10-dihydroxyanthracene compound as a starting material by the two step production method will be described. The 9,10-bis(alkoxycarbonylalkyleneoxy)anthracene compound having ester groups, represented by the formula (1) of the present invention, may be obtained as follows. In accordance with the following Reaction formula (2), the 9,10-dihydroxyanthracene compound represented by the formula (2) is reacted with a corresponding carboxylic acid represented by the formula (4) in the presence or in the absence of a basic compound to prepare a 9,10-bis(hydroxycarbonylalkyleneoxy)anthracene compound represented by the formula (5) as an intermediate, and the 9,10-bis(hydroxycarbonylalkyleneoxy)anthracene compound represented by the formula (5) is reacted with an alcohol compound represented by the formula (6) in accordance with Reaction formula (3), with a halogenated alkyl compound represented by the formula (7) in accordance with Reaction formula (4), or with a glycidyl ether compound represented by the formula (8) in accordance with Reaction formula (5), to obtain the 9,10-bis(alkoxycarbonylalkyleneoxy)anthracene compound having ester groups represented by the formula (1).

Reaction formula (2)

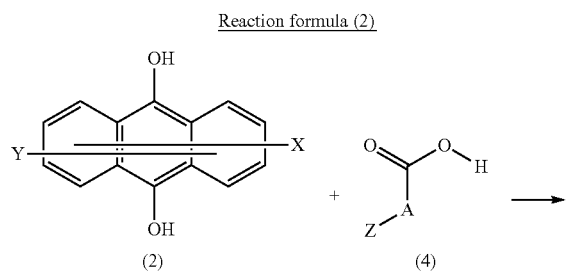

In Reaction formula (2), A is a $C_{1-20}$ alkylene group, which may be branched by an alkyl group. Each of X and Y is independently a hydrogen atom, a $C_{1-8}$ alkyl group or a halogen atom. Z is a chlorine atom, a bromine atom or an iodine atom.

Reaction formula (3)

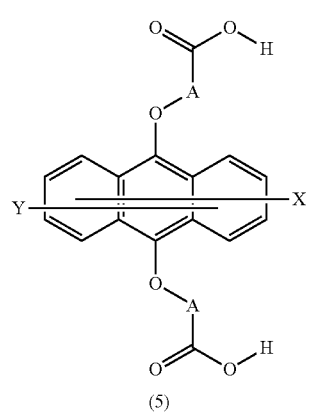

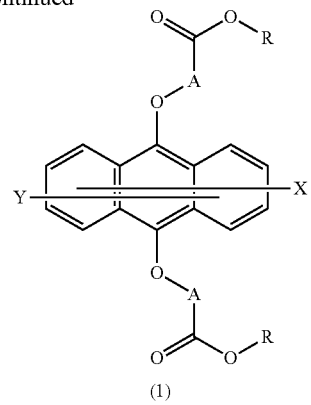

In Reaction formula (3), A is a $C_{1-20}$ alkylene group, which may be branched by an alkyl group. Each of X and Y is independently a hydrogen atom, a $C_{1-8}$ alkyl group or a halogen atom. R is a $C_{1-20}$ alkyl group, which may be branched by the alkyl group, which may be a cycloalkyl group or a cycloalkylalkyl group, which may be substituted by a hydroxy group, and of which one or more of carbon atoms may be substituted by an oxygen atom (excluding a case of forming a peroxide).

Reaction formula (4)

In Reaction formula (4), A is a $C_{1-20}$ alkylene group, which may be branched by an alkyl group. Each of X and Y is independently a hydrogen atom, a $C_{1-8}$ alkyl group or a halogen atom. R is a $C_{1-20}$ alkyl group, which may be branched by the alkyl group, which may be a cycloalkyl group or a cycloalkylalkyl group, which may be substituted by a hydroxy group, and of which one or more of carbon atoms may be substituted by an oxygen atom (excluding a case of forming a peroxide). D is a chlorine atom, a bromine atom or an iodine atom.

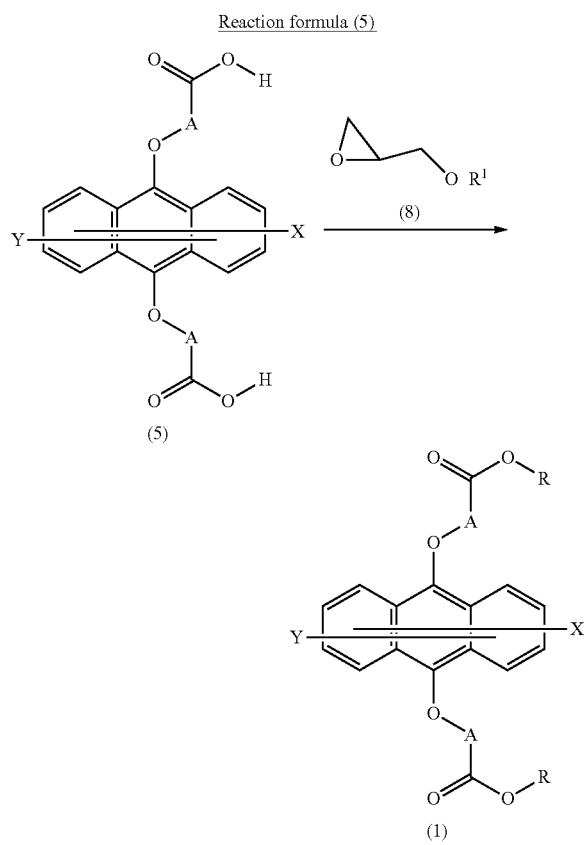

Reaction formula (5)

In Reaction formula (5), A is a $C_{1-20}$ alkylene group, which may be branched by an alkyl group, Each of X and Y is independently a hydrogen atom, a $C_{1-8}$ alkyl group or a halogen atom. R is a $C_{4-20}$ alkyl group, which may be branched by the alkyl group, which may be a cycloalkyl group or a cycloalkylalkyl group, which may be substituted by a hydroxy group, and of which one or more of carbon atoms may be substituted by an oxygen atom (excluding a case of forming a peroxide). $R^1$ is a hydrogen atom or a $C_{1-17}$ alkyl group, which may be branched by the alkyl group, which may be a cycloalkyl group or a cycloalkylalkyl group, which may be substituted by a hydroxy group, and of which one or more of carbon atoms may be substituted by an oxygen atom (excluding a case of forming a peroxide). In Reaction formula (5), for example, in a case where the substituent $R^1$ of the glycidyl ether compound represented by the formula (8) is a $C_1$ alkyl group, the substituent R of the corresponding 9,10-bis(alkoxycarbonylalkyleneoxy)anthracene compound having ester groups represented by the formula (1) is a 2-hydroxy-3-methoxypropoxy group. That is, in a case where the 9,10-bis(alkoxycarbonylalkyleneoxy) anthracene compound having ester groups represented by the formula (1) is to be obtained by reaction with the glycidyl ether compound represented by the formula (8) in accordance with Reaction formula (5), R in the formula (1) is a $C_{4-20}$ alkyl group.

First, the method for producing the 9,10-bis(hydroxycarbonylalkyleneoxy)anthracene compound represented by the formula (5) as an intermediate will be described.

The 9,10-dihydroxyanthracene compound represented by the formula (2) used as the material in Reaction formula (2) may be the same as mentioned for Reaction formula (1) and may be obtained by the same method.

Specific examples of the carboxylic acid represented by the formula (4) as the other material in Reaction formula (2) include chloroacetic acid, 2-chloropropionic acid, 3-chloropropionic acid, 2-chlorobutyric acid, 3-chlorobutyric acid, 4-chlorobutyric acid, 2-chlorovaleric acid, 3-chlorovaleric acid, 4-chlorovaleric acid, 5-chlorovaleric acid, bromoacetic acid, 2-bromopropionic acid, 3-bromopropionic acid, 2-bromobutyric acid, 3-bromobutyric acid, 4-bromobutyric acid, 2-bromovaleric acid, 3-bromovaleric acid, 4-bromovaleric acid, 5-bromovaleric acid, iodoacetic acid, 2-iodopropionic acid, 3-iodopropionic acid, 2-iodobutyric acid, 3-iodobutyric acid, 4-iodobutyric acid, 2-iodovaleric acid, 3-iodovaleric acid, 4-iodovaleric acid and 5-iodovaleric acid.

Among the above mentioned specific examples, chloro compounds and bromo compounds are preferred in view of availability and reactivity, and chloroacetic acid and bromoacetic acid are particularly preferred.

In Reaction formula (2), the amount of the carboxylic acid represented by the formula (4) used is preferably at least 2.0 molar times and less than 10.0 molar times, more preferably at least 2.2 molar times and less than 5.0 molar times, the 9,10-dihydroxyanthracene compound. If it is less than 2.0 molar times, the reaction will not be completed, and if it is 10.0 molar times or more, side reaction will occur, thus lowering the yield and the purity.

The basic compound used in Reaction formula (2) may, for example, be sodium hydroxide, potassium hydroxide, sodium hydride, potassium hydride, lithium hexamethyldisilazide, lithium diisopropylamide, triethylamine, tributylamine, trihexylamine, dimethylamine, diethylamine, dipropylamine, dibutylamine, cyclohexylamine, dimethylaniline, pyridine, 4,4-dimethylaminopyridine, piperidine, γ-picoline or lutidine.

The amount of the basic compound added is preferably at least 2.0 molar times and less than 10.0 molar times, more preferably at least 2.2 molar times and less than 8.0 molar times, the 9,10-dihydroxyanthracene compound. If it is less than 2.0 molar times, the reaction will not be completed, and if it is 10.0 molar times or more, side reaction will occur, thus lowering the yield and the purity.

The reaction is carried out in a solvent or without solvent. The solvent used is not particularly limited so long as it does not react with the materials used, and may, for example, be an aromatic solvent such as toluene, xylene or ethylbenzene, an ether solvent such as tetrahydrofuran or 1,4-dioxane, a ketone solvent such as acetone, methyl ethyl ketone or methyl isobutyl ketone, an amide solvent such as dimethylacetamide or dimethylformamide, a halogenated hydrocarbon solvent such as methylene chloride, ethylene dichloride or chlorobenzene, an alcohol such as methanol, ethanol or 1-propanol, or water.

In a case where the 9,10-dihydroxyanthracene compound is dissolved in an aqueous solution of an inorganic base and is reacted with the ester, use of a phase transfer catalyst is effective. The phase transfer catalyst may, for example, be tetramethylammonium bromide, tetraethylammonium bromide, tetrapropylammonium bromide, tetrabutylammonium bromide, trioctylmethylammonium bromide, trioctylethylammonium bromide, trioctylpropylammonium bromide, trioctylbutylammonium bromide, benzyldimethyloctadecylammonium bromide, tetramethylammonium chloride, tetraethylammonium chloride, tetrapropylammonium chloride, tetrabutylammonium chloride, trioctylmethylammonium chloride, trioctylethylammonium chloride, trioctylpropylammonium chloride, trioctylbutylammonium chloride or benzyldimethyloctadecylammonium chloride.

The amount of the phase transfer catalyst added is preferably at least 0.01 molar times and less than 1.0 molar times, more preferably at least 0.03 molar times and less than 0.5 molar times, the 9,10-dihydroxyanthracene compound. If it is less than 0.01 molar times, the reaction rate will be low, and if it is 1.0 molar times or more, the purity of the product will decrease.

The reaction temperature of this reaction is usually at least 0° C. and at most 100° C., preferably at least 10° C. and at most 50° C. If it is less than 0° C., the reaction will take too long, and if it exceeds 100° C., impurities tend to increase and the purity of the desired compound will decrease.

The reaction time of this reaction varies depending upon the reaction temperature and is usually from about 1 hour to about 20 hours. It is preferably from 2 hours to 10 hours.

After completion of the reaction, as the case requires, unreacted raw material, the solvent and the catalyst are removed by extraction, by filtration or the like alone or in combination. Since the product is in the form of a carboxylate, it is neutralized with a mineral acid or an organic acid to precipitate crystals, which are subjected to solid-liquid separation by filtration, and recrystallization is carried out as the case requires, to obtain the 9,10-bis(hydroxycarbonylalkyleneoxy)anthracene compound represented by the formula (5).

Now, the method for producing the 9,10-bis(alkoxycarbonylalkyleneoxy)anthracene compound having ester groups represented by the formula (1) by reacting the 9,10-bis(hydroxycarbonylalkyleneoxy)anthracene compound represented by the formula (5) and the alcohol compound represented by the formula (6) in the presence or in the absence of a catalyst, represented by Reaction formula (3), will be described.

In Reaction formula (3), specific examples of the alcohol compound represented by the formula (6) as the material include methanol, ethanol, n-propanol, isopropanol, n-butanol, isobutanol, sec-butanol, tert-butanol, 1-pentanol, 2-pentanol, 3-pentanol, hexanol, heptanol, octanol, 2-ethylhexanol, nonanol, decanol, dodecanol, cyclohexanol, cyclohexylmethanol, ethylene glycol and propylene glycol.

Among the above mentioned specific examples, preferred are methanol, ethanol, n-propanol, isopropanol, n-butanol, isobutanol, sec-butanol, tert-butanol, 1-pentanol, 2-pentanol, 3-pentanol, cyclohexanol, ethylene glycol and propylene glycol in view of availability, particularly preferred are methanol, ethanol, n-propanol, isopropanol, n-butanol, tert-butanol, 1-pentanol and cyclohexanol.

In Reaction formula (3), the amount of the alcohol compound represented by the formula (6) used is preferably at least 5 molar times and less than 100 molar times, more preferably at least 10 molar times and less than 50 molar times, the 9,10-bis(hydroxycarbonylalkyleneoxy)anthracene compound represented by the formula (5). If it is less than 5 molar times, the reaction will not be completed, and if it is at least 100 molar times, the reaction rate will be low, thus lowering the yield and the purity.

The catalyst to be used in Reaction formula (3) may, for example, be a mineral acid (sulfuric acid or hydrochloric acid), an organic acid (methanesulfonic acid or p-toluenesulfonic acid), a Lewis acid (boron fluoride etherate, aluminum trichloride, titanium tetrachloride, iron trichloride or zinc dichloride), a solid acid catalyst (manufactured by Futamura Chemical Co., Ltd.), Amberlist (manufactured by ORGANO CORPORATION), Nafion (manufactured by DuPont, registered trademark), a titanium tetraalkoxide compound (titanium tetraisopropoxide, titanium tetra-n-butoxide or titanium tetramethoxide) or an organic tin compound (dibutyltin dilaurate or dibutyltin oxide).

The amount of the catalyst added is, to the 9,10-bis (hydroxycarbonylalkyleneoxy)anthracene compound represented by the formula (5), preferably at least 0.01 mol % and less than 50 mol %, more preferably at least 0.1 mol % and less than 20 mol %. If it is less than 0.01 mol %, the reaction will not be completed, and if it is at least 50 mol %, side reaction will occur, thus lowering the yield and the purity.

The reaction is carried out in a solvent or without solvent. The solvent used is not particularly limited so long as it does not react with the alcohol compound used, and it may, for example, be an aromatic solvent such as toluene, xylene or ethylbenzene, an ether solvent such as tetrahydrofuran or 1,4-dioxane, a ketone solvent such as acetone, methyl ethyl ketone or methyl isobutyl ketone, an amide solvent such as dimethylacetamide or dimethylformamide, or a halogenated hydrocarbon solvent such as methylene chloride, ethylene dichloride or chlorobenzene. It is particularly preferred to use the alcohol compound both as the reaction substrate and as the solvent, in view of waste disposal reduction.

The reaction temperature of this reaction is usually at least 20° C. and at most 200° C., preferably at least 50° C. and at most 150° C. If it is less than 20° C., the reaction will take too long, and if it exceeds 200° C., impurities tend to increase and the purity of the desired compound will decrease.

The reaction time of this reaction varies depending upon the reaction temperature and is usually from about 1 hour to about 20 hours. It is preferably from 2 hours to 15 hours.

After completion of the reaction, as the case requires, unreacted raw material, the solvent and the catalyst are removed by neutralization, by washing, by vacuum distillation, by filtration or the like alone or in combination. In a case where the product is a solid, crystals will precipitate during the reaction, which may be subjected to solid-liquid separation by filtration, and as the case requires, recrystallization from a poor solvent such as an alcohol or hexane may be conducted. Otherwise, the crystals may be dried up as they are. In a case where the formed product is a liquid, it is dried up as it is, followed by purification e.g. by distillation as the case requires, to obtain the 9,10-bis (alkoxycarbonylalkyleneoxy)anthracene compound having ester groups.

Now, the method for producing the 9,10-bis(alkoxycarbonylalkyleneoxy)anthracene compound having ester groups represented by the formula (1) by reacting the 9,10-bis(hydroxycarbonylalkyleneoxy)anthracene compound represented by the formula (5) and the halogenated alkyl compound represented by the formula (7) in the presence or in the absence of a base, represented by Reaction formula (4), will be described.

Specific examples of the halogenated alkyl compound represented by the formula (7) used as the material in Reaction formula (4) include methyl chloride, ethyl chloride, n-propyl chloride, isopropyl chloride, butyl chloride, isobutyl chloride, sec-butyl chloride, tert-butyl chloride, pentyl chloride, hexyl chloride, heptyl chloride, octyl chloride, 2-ethylhexyl chloride, nonyl chloride, decyl chloride, dodecyl chloride, cyclohexyl chloride, 2-hydroxyethyl chloride, methyl bromide, ethyl bromide, n-propyl bromide, isopropyl bromide, butyl bromide, isobutyl bromide, sec-butyl bromide, tert-butyl bromide, pentyl bromide, hexyl bromide, heptyl bromide, octyl bromide, 2-ethylhexyl bromide, nonyl bromide, decyl bromide, dodecyl bromide, cyclohexyl bromide, 2-hydroxyethyl bromide, methyl iodide, ethyl iodide, n-propyl iodide, isopropyl iodide, butyl iodide, isobutyl iodide, sec-butyl iodide, tert-butyl iodide, pentyl iodide, hexyl iodide, heptyl iodide, octyl iodide, 2-ethylhexyl iodide, nonyl iodide, decyl iodide, dodecyl iodide, cyclohexyl iodide and 2-hydroxyethyl iodide.

Among the above mentioned specific examples, chlorides and bromides are preferred in view of availability and reactivity, and bromides are particularly preferred.

The amount of the halogenated alkyl compound represented by the formula (7) in Reaction formula (4) is preferably at least 2 molar times and less than 10 molar times, more preferably at least 3 molar times and less than 5 molar times, the 9,10-bis(hydroxycarbonylalkyleneoxy)anthracene compound represented by the formula (5). If it is less than 2 molar times, the reaction will not be completed, and if it is 10 molar times or more, side reaction will occur, thus lowering the yield and the purity.

The basic compound used in Reaction formula (4) may, for example, be sodium hydroxide, potassium hydroxide, sodium hydride, potassium hydride, sodium carbonate, potassium carbonate, sodium hydrogen carbonate, lithium hexamethyldisilazide, lithium diisopropylamide, triethylamine, tributylamine, trihexylamine, dimethylamine, diethylamine, dipropylamine, dibutylamine, cyclohexylamine, dimethylaniline, pyridine, 4,4-dimethylaminopyridine, piperidine, γ-picoline or lutidine.

The amount of the basic compound added is preferably at least 0.5 molar time and less than 10 molar times, more preferably at least 1 molar time and less than 5 molar times, the 9,10-bis(hydroxycarbonylalkyleneoxy)anthracene compound represented by the formula (5). If it is less than 0.5 molar time, the reaction will not be completed, and if it is 10 molar times or more, side reaction will occur, thus lowering the yield and the purity.

The reaction is carried out in a solvent or without solvent. The solvent used is not particularly limited so long as it does not react with the alcohol compound used, and it may, for example, be an aromatic solvent such as toluene, xylene or ethylbenzene, an ether solvent such as tetrahydrofuran or 1,4-dioxane, a ketone solvent such as acetone, methyl ethyl ketone or methyl isobutyl ketone, an amide solvent such as dimethylacetamide or dimethylformamide, or a halogenated hydrocarbon solvent such as methylene chloride, ethylene dichloride or chlorobenzene.

The reaction temperature of this reaction is usually at least 0° C. and at most 200° C., preferably at least 20° C. and at most 100° C. If it is less than 0° C., the reaction will take too long, and if it exceeds 200° C., impurities tend to increase and the purity of the desired compound will decrease.

The reaction time of this reaction varies depending upon the reaction temperature and is usually from about 1 hour to about 20 hours. It is preferably from 2 to 15 hours.

After completion of the reaction, as the case requires, unreacted raw material, the solvent and the catalyst are removed by neutralization, by washing, by vacuum distillation, by filtration or the like alone or in combination. In a case where the product is a solid, crystals will precipitate during the reaction, which may be subjected to solid-liquid separation by filtration, and as the case requires, recrystallization from a poor solvent such as an alcohol or hexane may be conducted. Otherwise, the crystals may be dried up as they are. In a case where the formed product is a liquid, it is dried up as it is, followed by purification e.g. by distillation as the case requires, to obtain the 9,10-bis (alkoxycarbonylalkyleneoxy)anthracene compound having ester groups.

Now, the method for producing the 9,10-bis(alkoxycarbonylalkyleneoxy)anthracene compound having ester groups represented by the formula (1) by reacting the 9,10-bis(hydroxycarbonylalkyleneoxy)anthracene compound represented by the formula (5) and the glycidyl ether compound represented by the formula (8) in the presence or in the absence of a base, represented by Reaction formula (5), will be described.

Specific examples of the glycidyl ether compound represented by the formula (8) used as the material in Reaction formula (5) include methyl glycidyl ether, ethyl glycidyl ether, propyl glycidyl ether, butyl glycidyl ether, pentyl glycidyl ether, hexyl glycidyl ether, 2-ethylhexyl glycidyl ether, octyl glycidyl ether, cyclohexyl glycidyl ether, allyl glycidyl ether, methallyl glycidyl ether and glycidol.

The amount of the glycidyl ether compound represented by the formula (8) in Reaction formula (5) is preferably at least 2 molar times and less than 10 molar times, more preferably at least 3 molar times and less than 5 molar times, the 9,10-bis(hydroxycarbonylalkyleneoxy)anthracene compound represented by the formula (5). If it is less than 2 molar times, the reaction will not be completed, and if it is 10 molar times or more, side reaction will occur, thus lowering the yield and the purity.

The basic compound used in Reaction formula (5) may, for example, be sodium hydroxide, potassium hydroxide, sodium hydride, potassium hydride, sodium carbonate, potassium carbonate, sodium hydrogen carbonate, lithium hexamethyldisilazide, lithium diisopropylamide, triethylamine, tributylamine, trihexylamine, dimethylamine, diethylamine, dipropylamine, dibutylamine, cyclohexylamine, dimethylaniline, pyridine, 4,4-dimethylaminopyridine, piperidine, γ-picoline or lutidine.

The amount of the basic compound added is preferably at least 0.5 molar time and less than 10 molar times, more preferably at least 1 molar time and less than 5 molar times, the 9,10-bis(hydroxycarbonylalkyleneoxy)anthracene compound represented by the formula (5). If it is less than 0.5 molar time, the reaction will not be completed, and if it is 10 molar times or more, side reaction will occur, thus lowering the yield and the purity.

The reaction is carried out in a solvent or without solvent. The solvent used is not particularly limited so long as it does not react with the glycidyl ether compound used, and it may, for example, be an aromatic solvent such as toluene, xylene or ethylbenzene, an ether solvent such as tetrahydrofuran or 1,4-dioxane, a ketone solvent such as acetone, methyl ethyl ketone or methyl isobutyl ketone, an amide solvent such as dimethylacetamide or dimethylformamide, or a halogenated hydrocarbon solvent such as methylene chloride, ethylene dichloride or chlorobenzene.

The reaction temperature of this reaction is usually at least 0° C. and at most 200° C., preferably at least 20° C. and at most 100° C. If it is less than 0° C., the reaction will take too long, and if it exceeds 200° C., impurities tend to increase and the purity of the desired compound will decrease.

The reaction time of this reaction varies depending upon the reaction temperature and is usually from about 1 hour to about 20 hours. It is preferably from 2 hours to 15 hours.

After completion of the reaction, as the case requires, unreacted raw material, the solvent and the catalyst are removed by neutralization, by washing, by vacuum distillation, by filtration or the like alone or in combination. In a case where the product is a solid, crystals will precipitate during the reaction, which may be subjected to solid-liquid separation by filtration, and as the case requires, recrystallization from a poor solvent such as an alcohol or hexane may be conducted. Otherwise, the crystals may be dried up as they are. In a case where the formed product is a liquid, it is dried up as it is, followed by purification e.g. by distillation as the case requires, to obtain the 9,10-bis (alkoxycarbonylalkyleneoxy)anthracene compound having ester groups.

(Single Step Production Method (2))

Now, the method for preparing the 9,10-bis(alkoxycarbonylalkyleneoxy)anthracene compound having ester groups of the present invention using the 9,10-anthraquinone compound as the starting material by single step production method will be described. The 9,10-bis(alkoxycarbonylalkyleneoxy)anthracene compound having ester groups represented by the formula (1) of the present invention may be obtained by reducing the 9,10-anthraquinone compound represented by the formula (9) in accordance with the following Reaction formula (6) to the 9,10-dihydroxyanthracene compound, which is reacted with the corresponding ester compound represented by the formula (3) in the presence or in the absence of a basic compound. By reducing the 9,10-anthraquinone compound, the 9,10-dihydroxyanthracene compound represented by the formula (2) can be formed. In this reaction, the 9,10-dihydroxyanthracene compound may be isolated and then subjected to the next reaction, or the 9,10-dihydroxyanthracene compound may be subjected to the next reaction continuously without being taken out (one-pot synthesis).

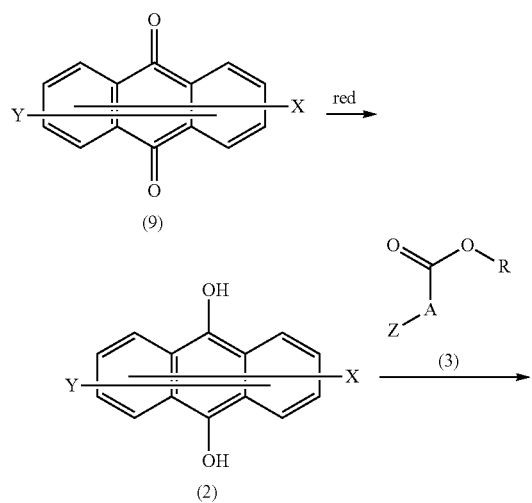

Reaction formula (6)

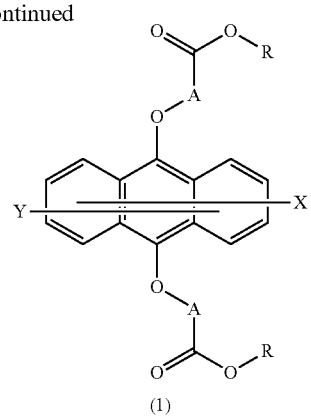

(1)

In Reaction formula (6), A is a $C_{1-20}$ alkylene group, which may be branched by an alkyl group. R is a $C_{1-20}$ alkyl group, which may be branched by the alkyl group, which may be a cycloalkyl group or a cycloalkylalkyl group, which may be substituted by a hydroxy group, and of which one or more of carbon atoms may be substituted by an oxygen atom (excluding a case of forming a peroxide). Each of X and Y is independently a hydrogen atom, a $C_{1-8}$ alkyl group or a halogen atom. Z is a chlorine atom, a bromine atom or an iodine atom.

The 9,10-anthraquinone compound represented by the formula (9) used as the material in Reaction formula (6) is industrially produced and is easily prepared and available.

Specific examples of the 9,10-anthraquinone compound used as the material in this reaction include 9,10-anthraquinone, 2-methyl-9,10-anthraquinone, 2-ethyl-9,10-anthraquinone, 2-tert-pentyl-9,10-anthraquinone, 2-amyl-9,10-anthraquinone, 2,6-dimethyl-9,10-anthraquinone, 2-chloro-9,10-anthraquinone and 2-bromo-9,10-anthraquinone.

As the method for reducing the 9,10-anthraquinone compound into the 9,10-dihydroxyanthracene compound, a method of reducing the 9,10-anthraquinone in a solvent or in an aqueous solution using a reducing agent. The reducing agent may, for example, be a hydrosulfite, thiourea dioxide, saccharides, a metal such as Sn—Hg, Zn—Cu, Zn or $SnCl_2 \cdot 2H_2O$, a metal hydride compound such as lithium aluminum hydride or sodium borohydride, or hydrazine. Further, a method for producing the 9,10-dihydroxyanthracene compound by catalytic hydrogenation of the 9,10-anthraquinone compound in a solvent or in an aqueous alkali solution by molecular form hydrogen (hydrogen gas) in the presence of a hydrogenation catalyst such as palladium, has been known. Further, a method of reducing the 9,10-anthraquinone compound using as a reducing agent an alkali salt solution of 1,4-dihydro-9,10-dihydroxyanthracene compound to produce the 9,10-dihydroxyanthracene compound has been known. In such a case, the compound is obtained in the form of an aqueous alkali salt solution.

The solvent used in reducing step is not particularly limited so long as it is stable against the reducing agent, and for example, in a case where sodium hydrosulfite is used as the reducing agent, the solvent may, for example, be water, a halogen solvent such as methylene chloride, chloroform, dichloroethane or chlorobenzene, a hydrocarbon solvent such as benzene, toluene, xylene, hexane or cyclohexane, an ether solvent such as triethylene glycol dimethyl ether, ethylene glycol dimethyl ether, tetrahydrofuran (THF), dioxane or diethyl ether, or a nitrile solvent such as benzonitrile, and they be used alone or as a mixture of two or more. In the case of an aqueous system, the reduction is carried out preferably in an aqueous sodium hydroxide solution although it depends on the reducing agent.

Further, reduction of the 9,10-anthraquinone compound is carried out preferably in an inert gas atmosphere. The reduction in an inert gas atmosphere means, for example, that the reaction solvent is deoxidized by bubbling with an inert gas such as a nitrogen gas, that the reaction is carried out in an inert gas atmosphere, or that the reaction is carried out in a reaction container replaced with an inert gas.

The amount of the reducing agent used varies depending upon the reducing agent used and is not particularly limited so long as two electrons can be donated to 1 mol of the 9,10-anthraquinone compound, and in a case where sodium hydrosulfite is used as an example, considering the reaction efficiency, etc., it is preferred to use the reducing agent in an amount of from 2 to 10 mol, more preferably from 2 to 5 mol per 1 mol of the 9,10-anthraquinone compound. If the reducing agent is used in excess, reduction will further proceed to form anthrone, such being unfavorable.

The 9,10-dihydroxyanthracene compound obtained by this reduction reaction may be isolated and subjected to the next reaction, or may be subjected to the next step reaction with the ester compound without being isolated, although depending upon the type of the reducing agent and the solvent used.

And, the 9,10-dihydroxyanthracene compound represented by the formula (2) obtained by the reduction reaction and the ester compound represented by the formula (3) are reacted to obtain the 9,10-bis(alkoxycarbonylalkyleneoxy) anthracene compound having ester groups of the present invention. The ester compound represented by the formula (3) used in the reaction, the reaction conditions, etc. are the same as the compound and the reaction conditions disclosed in Single step production method (1).

(Two Step Production Method (2))

Now, the method for preparing the 9,10-bis(alkoxycarbonylalkyleneoxy)anthracene compound having ester groups of the present invention using the 9,10-anthraquinone compound as a starting material by two step production method will be described. The 9,10-bis(alkoxycarbonylalkyleneoxy) anthracene compound having ester groups represented by the formula (1) of the present invention is obtained as follows. The 9,10-anthraquinone compound represented by the formula (9) is reduced in accordance with the following Reaction formula (7) to the 9,10-dihydroxyanthracene compound, which is reacted with the corresponding carboxylic acid represented by the formula (4) in the presence or in the absence of a basic compound to prepare a 9,10-bis(hydroxycarbonylalkyleneoxy)anthracene compound represented by the formula (5) as an intermediate, and then in the same manner as in Two step production method (1), the 9,10-bis(hydroxycarbonylalkyleneoxy)anthracene compound represented by the formula (5) is reacted with the alcohol compound represented by the formula (6), the halogenated alkyl compound represented by the formula (7) or the glycidyl ether compound represented by the formula (8) to obtain the 9,10-bis(alkoxycarbonylalkyleneoxy)anthracene compound having ester groups represented by the formula (1). In this reaction, the 9,10-dihydroxyanthracene compound may be isolated and subjected to the next step reaction, or may be subjected to the next step reaction continuously without being taken out.

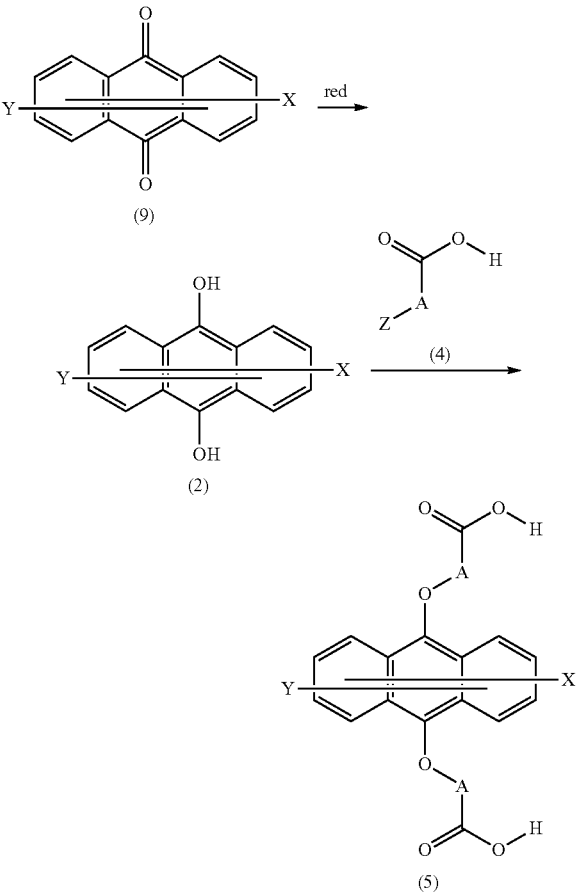

In Reaction formula (7), A is a $C_{1-20}$ alkylene group, which may be branched by an alkyl group. R is a $C_{1-20}$ alkyl group, which may be branched by the alkyl group, which may be a cycloalkyl group or a cycloalkylalkyl group, which may be substituted by a hydroxy group, and of which one or more of carbon atoms may be substituted by an oxygen atom (excluding a case of forming a peroxide). Each of X and Y is independently a hydrogen atom, a $C_{1-8}$ alkyl group or a halogen atom. Z is a chlorine atom, a bromine atom or an iodine atom.

The 9,10-anthraquinone compound represented by the formula (9) used as the material in Reaction formula (7) is an industrially produced compound and is easily prepared and available.

Specific examples of the 9,10-anthraquinone compound used as the material in the reaction include 9,10-anthraquinone, 2-methyl-9,10-anthraquinone, 2-ethyl-9,10-anthraquinone, 2-tert-pentyl-9,10-anthraquinone, 2,6-dimethyl-9,10-anthraquinone, 2-chloro-9,10-anthraquinone and 2-bromo-9,10-anthraquinone.

As the method of reducing the 9,10-anthraquinone compound to obtain the 9,10-dihydroxyanthracene compound, the same reduction method and the same conditions as in Single step production method (2) may be employed. Further, in the two step production method also, the 9,10-dihydroxyanthracene compound obtained by the reduction reaction may be isolated and subjected to the next step reaction, or may be subjected to the next step reaction without being isolated, although depending upon the type of the reducing agent and the solvent used.

The 9,10-dihydroxyanthracene compound represented by the formula (2) obtained by the reduction reaction is reacted with the corresponding carboxylic acid represented by the formula (4) in the presence or in the absence of a basic compound to prepare the 9,10-bis(hydroxycarbonylalkyleneoxy)anthracene compound represented by the formula (5) as an intermediate, and the carboxylic acid represented by the formula (4) used and the reaction conditions are the same as the compound and the reaction conditions disclosed in Two step production method (1). Further, the 9,10-bis(hydroxycarbonylalkyleneoxy)anthracene compound prepared is reacted with the alcohol compound represented by the formula (6), the halogenated alkyl compound represented by the formula (7) or the glycidyl ether compound represented by the formula (8) to obtain the 9,10-bis(alkoxycarbonylalkyleneoxy)anthracene compound having ester groups represented by the formula (1), and the alcohol compound represented by the formula (6), the halogenated alkyl compound represented by the formula (7) and the glycidyl ether compound represented by the formula (8) used, the reaction conditions, etc. are the same as the compounds and the reaction conditions disclosed in Two step production method (1).

(Photopolymerization Sensitizer)

The 9,10-bis(alkoxycarbonylalkyleneoxy)anthracene compound having ester groups represented by the formula (1) of the present invention functions as a photopolymerization sensitizer which is excited by light having a specific wavelength and gives the excitation energy to the photopolymerization initiator. By this effect, it is possible to initiate photopolymerization efficiency even with long wavelength light which will not sufficiently activate the photopolymerization initiator. Such a photopolymerization sensitizer and a photopolymerization initiator may be mixed with a photopolymerizable compound to form a photopolymerizable composition. Such a photopolymerizable composition may easily be photo-cured, for example, by irradiation with a long wavelength light such as an ultraviolet LED light with a center wavelength of 405 nm.

The 9,10-bis(alkoxycarbonylalkyleneoxy)anthracene compound having ester groups represented by the formula (1) of the present invention, which has ester groups via an alkylene group in its structure, is characterized by having high affinity with the photopolymerizable composition and its cured product, and in that the degree of migration or blooming in the photopolymerizable composition and its cured product is very low. Further, in a case where in the formula (1), R is a cycloalkyl group or a cycloalkylalkyl group, the solubility in various monomers will improve, whereby the compound can be soluble in various monomers at high concentrations, thus broadening the application range. The solubility is high particularly in a case where R is a cyclohexyl group.

Further, the ester groups in the 9,10-bis(alkoxycarbonylalkyleneoxy)anthracene compound having ester groups represented by the formula (1) of the present invention are bonded to the anthracene ring via A as the alkylene group, and thus the ultraviolet absorption wavelength of such a compound is on the longer wavelength side as compared with the compound without A. Accordingly, such a compound is effective also in a case where the sensitizing effect of a compound without A is weak.

Further, the 9,10-bis(alkoxycarbonylalkyleneoxy)anthracene compound having ester groups represented by the formula (1) of the present invention wherein A is a $C_1$ methylene group, has high sensitizing power in radical polymerization as compared with the 9,10-bis(alkoxycarbonylalkyleneoxy)anthracene compound wherein A has two or more carbon atoms. This effect is considered to be as follows. Anthracene compounds generally have radical polymerization inhibitory effect, and this effect is lessened by bonding of oxygen atoms at the 9,10-positions, and the 9,10-bis(alkoxycarbonylalkyleneoxy)anthracene compound having ester groups represented by the formula (1) of the present invention wherein A is a methylene group, has a particularly weakened inhibitory effect and has high activity as a radical polymerization sensitizer considered to be due to the steric positional relationship between the anthracene ring and the ester groups.

(Photopolymerization Initiator)

The photopolymerization initiator used in the present invention may, for example, be an onium salt polymerization initiator, a benzyl methyl ketal polymerization initiator, an α-hydroxyalkylphenone polymerization initiator, an oxime ester polymerization initiator, an α-aminoacetaophenone polymerization initiator, an acylphosphine oxide polymerization initiator, a biimidazole polymerization initiator, a triazine polymerization initiator or a thioxanthone polymerization initiator.

As the onium salt polymerization initiator, usually an iodonium salt or a sulfonium salt is used. The iodonium salt may, for example, be 4-isobutylphenyl-4'-methylphenyl iodonium hexafluorophosphate, bis(dodecylphenyl)iodonium hexamethoxyantimonate, 4-isopropylphenyl-4'-methylphenyliodonium tetrakis pentamethoxyphenyl borate, or 4-isopropylphenyl-4'-methylphenyliodonium tetrakis pentafluorophenyl borate, and for example, Irgacure 250 manufactured by BASF (registered trademark), Rhodorsil 2074 manufactured by Rhodia Co., Ltd. (registered trademark) or IK-1 manufactured by San Apro Co., Ltd. may be used. Further, the sulfonium salt may, for example, be S,S,S',S'-tetraphenyl-S,S'-(4,4'-thiodiphenyl)disulfonium bishexamethoxyphosphate, diphenyl-4-phenylthiophenylsulfonium hexamethoxyphosphate or triphenylsulfonium hexamethoxyphosphate, and for example, CPI-100P, CPI101P or CPI-200K manufactured by Daicel Corporation, Irgacure 270 manufactured by BASF, or UVI6992 manufactured by Dow Chemical, may be used. Such a photopolymerization initiator may be used alone or in combination of two or more.

One of characteristics of the 9,10-bis(alkoxycarbonylalkyleneoxy)anthracene compound having ester groups of the present invention is having a photopolymerization sensitizing effect not only for the iodonium salt but also for the sulfonium salt as the onium salt.

Further, the 9,10-bis(alkoxycarbonylalkyleneoxy)anthracene compound having ester groups represented by the formula (1) of the present invention has an excellent photopolymerization sensitizing effect for a radical polymerization initiator having no absorption at long wavelength, such as a benzyl methyl ketal polymerization initiator, an α-hyroxyalkylphenone polymerization initiator or a biimidazole polymerization initiator. It also has an effect to increase the polymerization rate or to improve physical properties of the obtainable polymer in a polymerization reaction using a polymerization initiator having absorption in a long wavelength region, such as an acylphosphine oxide.

The benzyl methyl ketal polymerization initiator may, for example, be 2,2-dimethoxy-1,2-diphenylethan-1-one (tradename "Irgacure 651" manufactured by BASF), and the α-hydroxyalkylphenone radical polymerization initiator may be 2-hydroxy-2-methyl-1-phenylpropan-1-one (tradename "DAROCUR 1173" manufactured by BASF), 1-hydroxycyclohexyl phenyl ketone (tradename "Irgacure 184" manufactured by BASF), 1-[4-(2-hydroxyethoxy)-phenyl]-2-hydroxy-2-methyl-1-propan-1-one (tradename "Irgacure 2959" manufactured by BASF) or 2-hydroxy-1-{4-[4-(2-hydroxy-2-methylpropionyl)-benzyl]phenyl}-2-methyl-1-one (tradename "Irgacure 127" manufactured by BASF).

Particularly preferred is 2,2-dimethoxy-1,2-diphenylethan-1-one (tradename "Irgacure 651" manufactured by BASF) which is a benzyl methyl ketal polymerization initiator, or 2-hydroxy-2-methyl-1-phenylpropan-1-one (tradename "DAROCUR 1173" manufactured by BASF) or 1-hydroxycyclohexyl phenyl ketone (tradename "Irgacure 184" manufactured by BASF) which is an α-hydroxyalkylphenone radical photopolymerization initiator.

Further, it is possible to use acetophenone, 2-hydroxy-2-phenylacetophenone, 2-ethoxy-2-phenylacetophenone, 2-methoxy-2-phenylacetophenone, 2-isopropoxy-2-phenylacetophenone or 2-isobutoxy-2-phenylacetophenone which is an acetophenone polymerization initiator, benzyl or 4,4'-dimethoxybenzyl which is a benzyl polymerization initiator, or 2-ethylanthraquinone, 2-tert-butylanthraquinone, 2-phenoxyanthraquinone, 2-(phenylthio)anthraquinone or 2-(hydroxyethylthio)anthraquinone which is an anthraquinone polymerization initiator.

The biimidazole polymerization initiator may, for example be a 2,4,5-triarylimidazole dimer such as 2-(o-chlorophenyl)-4,5-diphenylimidazole dimer, 2-(o-chlorophenyl)-4,5-di(methoxyphenyl)imidazole dimer, 2-(o-fluorophenyl)-4,5-diphenylimidazole dimer, 2-(o-methoxyphenyl)-4,5-diphenylimidazole dim er or 2-(p-methoxyphenyl)-4,5-diphenylimidazole dimer.

The α-aminoacetophenone polymerization initiator may, for example, be 2-methyl-1-[4-(methylthio)phenyl]-2-morpholinopropan-1-one (tradename "Irgacure 907" manufactured by BASF), 2-benzyl-2-(dimethylamino)-4'-morpholinobutyrophenone (tradename "Irgacure 369" manufactured by BASF), 2-dimethylamino-2-(4-methylbenzyl)-1-(4-morpholin-4-yl-phenyl)butan-1-one (tradename "Irgacure 379" manufactured by BASF).

The acylphosphine oxide polymerization initiator may, for example, be 2,4,6-trimethylbenzoyl-diphenylphosphine oxide (tradename "Irgacure TPO" manufactured by BASF), or bis(2,4,6-trimethylbenzoyl)phenylphosphine oxide (tradename "Irgacure 819" manufactured by BASF).

The oxime ester polymerization initiator may, for example, be 1,2-octanedione, 1-[4-(phenylthio)phenyl]-, 2-(o-benzoyloxime) (tradename "Irgacure OXE01" manufactured by BASF), ethanone, 1-[9-ethyl-6-(2-methylbenzoyl)-9H-carbazol-3-yl]-, 1-(o-acetyloxime) (tradename "Irgacure OXE02" manufactured by BASF), [8-[[(acetyloxy)imino][2-(2,2,3,3-tetrafluoropropoxy)phenyl]methyl]-11-(2-ethylhexyl)-11H-benzo[a]carbazol-5-yl]-,(2,4,6-trimethylphenyl) (tradename "Irgacure OXE03" manufactured by BASF).

The triazine polymerization initiator may, for example, be 2-(3,4-methylenedioxyphenyl)-4,6-bis(trichloromethyl)-1,3,5-triazine, 2-(4-methoxyphenyl)-4,6-bis(trichloromethyl)-1,3,5-triazine.

The thioxanthone polymerization initiator may, for example, be 2,4-diethylthioxanthone or 2-isopropylthioxanthone.

The onium salt polymerization initiator, the benzyl methyl ketal polymerization initiator, the α-hydroxyalkylphenone polymerization initiator, the oxime ester polymerization initiator, the α-aminoacetophenone polymerization initiator, the acylphosphine oxide polymerization initiator, the biimidazole polymerization initiator, the triazine polymerization initiator, and the thioxanthone polymerization initiator may be used alone or in combination of two or more depending upon the application.

The amount of the photopolymerization sensitizer containing the 9,10-bis(alkoxycarbonylalkyleneoxy)anthracene compound having ester groups represented by the formula (1) of the present invention used to the photopolymerization initiator is not particularly limited, and is usually within a range of at least 5 wt % and at most 100 wt %, preferably at least 10 wt % and at most 50 wt % to the photopolymerization initiator. If the amount of the photopolymerization sensitizer used is less than 5 wt %, photopolymerization of a photopolymerizable compound will take too long, and on the other hand, even if it exceeds 100 wt %, no further effect will be obtained.

(Photopolymerization Initiator Composition)

The photopolymerization sensitizer containing the 9,10-bis(alkoxycarbonylalkyleneoxy)anthracene compound having ester groups represented by the formula (1) of the present invention may be directly added to a photopolymerizable compound, or it may be preliminarily blended with a photopolymerization initiator to prepare a photopolymerization initiator composition, which is added to a photopolymerizable compound. That is, the photopolymerization initiator composition of the present invention is a composition comprising at least the photopolymerization sensitizer containing the 9,10-bis(alkoxycarbonylalkyleneoxy)anthracene compound having ester groups represented by the formula (1) and a photopolymerization initiator.

(Photopolymerizable Composition)

Further, by blending the photopolymerization initiator composition and a photopolymerizable compound, a photopolymerizable composition may be prepared. The photopolymerizable composition of the present invention is a composition comprising the photopolymerizable initiator composition comprising the photopolymerization sensitizer containing the 9,10-bis(alkoxycarbonylalkyleneoxy)anthracene compound having ester groups of the present invention and a photopolymerization initiator, and a photoradical polymerizable compound or a photocationic polymerizable compound. The photopolymerization sensitizer containing the 9,10-bis(alkoxycarbonylalkyleneoxy)anthracene compound having ester groups of the present invention, and the photopolymerization initiator, may be separately added to a photoradical polymerizable compound or a photocationic polymerizable compound and forms a photopolymerization initiator composition in the photoradical polymerizable compound or the photocationic polymerizable compound. Further, a hybrid composition comprising both a photoradical polymerizable compound and a photocationic polymerizable compound may be employed.

The photoradical polymerizable compound may, for example, be an organic compound having a double bond such as styrene, vinyl acetate, acrylic acid, methacrylic acid, acrylonitrile, methacrylonitrile, acrylamide, an acrylic acid ester or a methacrylic acid ester. Among such radical polymerizable compounds, in view of the film forming performance, etc., preferred is an acrylic acid ester or a methacrylic acid ester (hereinafter both will generally be referred to as a (meth)acrylic acid ester). The (meth)acrylic acid ester may, for example, be methyl acrylate, butyl acrylate, cyclohexyl acrylate, 2-ethylhexyl acrylate, 2-hydroxyethyl acrylate, isobornyl acrylate, methyl methacrylate, butyl methacrylate, cyclohexyl methacrylate, tetraethylene glycol diacrylate, trimethylolpropane triacrylate, pentaerythritol triacrylate, tricyclo[5,2,1,0$^{2,6}$]decanedimethanol diacrylate, isobornyl methacrylate, epoxy acrylate, urethane acrylate, polyester acrylate, polybutadiene acrylate, polyol acrylate, polyether acrylate, silicone resin acrylate or imide acrylate. Such a photoradical polymerizable compound may be used alone or as a mixture of two or more.

The photocationic polymerizable compound may, for example, be an epoxy compound, an oxetane compound or a vinyl ether. As the epoxy compound, commonly, an alicyclic epoxy compound, an epoxy-modified silicone or an aromatic glycidyl ether may, for example, be mentioned. The alicyclic epoxy compound may, for example, be 3',4'-epoxycyclohexylmethyl-3,4-epoxycyclohexanecarboxylate (manufactured by Daicel Corporation, tradename: CELLOXIDE 2021P, registered trademark), 3,3',4,4'-diepoxy) bicyclohexyl (manufactured by Daicel Corporation, tradename: CELLOXIDE 8010), or bis(3,4-epoxycyclohexyl) adipate. The epoxy-modified silicone may, for example, be UV-9300 manufactured by GE Toshiba Silicones. The aromatic glycidyl compound may, for example, be 2,2'-bis(4-glycidyloxyphenyl)propane. The oxetane compound may, for example, be 3-ethyl-3-hydroxymethyloxetane (oxetane alcohol) (manufactured by TOAGOSEI CO., LTD., tradename: OXT-101), 2-ethylhexyl oxetane (manufactured by TOAGOSEI CO., LTD., tradename: OXT-212), xylylene bisoxetane (manufactured by TOAGOSEI CO., LTD., tradename: OXT-121), or 3-ethyl-3{[(3-ethyloxetan-3-yl)methoxy]methyl}oxetane (manufactured by TOAGOSEI CO., LTD., tradename: OXT-221). The vinyl ether may, for example, be methyl vinyl ether, ethyl vinyl ether, isobutyl vinyl ether or 2-ethylhexyl vinyl ether. Such a photocationic polymerizable compound may be used alone or as a mixture of two or more.

As the photopolymerizable compound, the photoradical polymerizable compound may be used alone, or the photoradical polymerizable compound and the photocationic polymerizable compound may be used as mixed.

The photopolymerization sensitizer of the present invention may function as the sensitizer for both photoradical polymerization and photocationic polymerization, and by selecting a proper photopolymerization initiator, it is effective for polymerization of a photopolymerizable composition containing both the photoradical polymerizable compound and the photocationic polymerizable compound.

The mixing ratio of the photocationic polymerizable compound and the photoradical polymerizable compound is not particularly limited, and is properly selected depending upon the physical properties of a coating film or a formed product to be obtained by photopolymerizing and curing the composition. Usually, the compositional ratio is determined within a range of the weight ratio of the photocationic polymerizable compound to the photoradical polymerizable compound is from 1:99 to 99:1, preferably from 20:80 to 80:20.

One type each of the photocationic polymerizable compound and the photoradical polymerizable compound may be used, or two or more types of each of the polymerizable compounds may be used in combination. When two or more types of such photopolymerizable compounds are used in combination, the mixing ratio of the photocationic polymerizable compound to the photoradical polymerizable compound is considered as the ratio of the total amounts of the respective photopolymerizable compounds.

The photopolymerization initiator used for the photopolymerizable composition of the present invention may be the above-described photoradical initiator or photocationic initiator. Usually, when the photoradical polymerizable compound is used as the photopolymerizable compound, the photoradical polymerization initiator is used. Further, when the photoradical polymerizable compound and the photocationic polymerizable compound are used in combination as the photopolymerizable compound, as the photopolymerization initiator, the photoradical polymerization initiator or the photocationic polymerization initiator may be used alone, or both of them may be used as mixed.

Particularly, some of the photocationic polymerization initiators generate cationic initiation active species and radical initiation active species by light irradiation, and when such an initiator is used, it is possible to initiate photopolymerization of both the photocationic polymerizable compound and the photoradical polymerizable compound by such an initiator by itself.

Further, the photopolymerizable composition of the present invention may contain a binder polymer such as an acrylic resin, a styrene resin or an epoxy resin. It may further contain an alkali soluble resin.

It may further contain a pigment and/or a dye. In a case where it contains a pigment, it may contain a dispersing agent therefor.

As the pigment, either an inorganic pigment or an organic pigment may be used. The inorganic pigment may be carbon black (C. I. Pigment Black 7) such as furnace black, lamp black, acetylene black or channel black, iron oxide or titanium oxide. The organic pigment may be an azo pigment such as an insoluble azo pigment, a condensed azo pigment, azo lake or a chelate azo pigment, a polycyclic pigment such as a phthalocyanine pigment, a perylene or perinone pigment, an anthraquinone pigment, a quinacridone pigment, a dioxane pigment, a thioindigo pigment, an isoindrinone pigment or a quinophthalone pigment, a dye chelate (such as basic dye chelate or acidic dye chelate), a dyeing lake (basic dyeing lake or acidic dyeing lake), a nitro pigment, a nitroso pigment, aniline black or a daylight fluorescent pigment. Such pigments may be used alone or in combination of two or more.

The dye is not particularly limited, and an acidic dye, a direct dye, a reactive dye or a basic dye may be used. The dyes may be used alone or in combination of two or more. Further, the pigment and the dye may be used in combination.

The dispersing agent for dispersing the pigment is not particularly limited and may, for example, be a dye dispersion such as a polymer dispersion. Its specific examples include ones containing as the main component at least one of a polyoxyalkylene polyalkylene polyamine, vinyl polymer and copolymer, acrylic polymer and copolymer, polyester, polyamide, polyimide, polyurethane, an amino polymer, a silicon-containing polymer, a sulfur-containing polymer, a fluorinated polymer and an epoxy resin.

In the photopolymerizable composition of the present invention, the amount of the photopolymerizable initiator composition used is within a range of at least 0.005 wt % and at most 10 wt %, preferably at least 0.025 wt % and at most 5 wt %, to the photopolymerizable composition. If it is less than 0.005 wt %, photopolymerization of the photopolymerizable composition will take long, and on the other hand, if it exceeds 10 wt %, the hardness of a photo-cured product obtained by photopolymerization will be low, and physical properties of the cured product will deteriorate.

The photopolymerizable composition of the present invention may contain, within a range not to impair the effects of the present invention, in addition to the above, resin additives such as a diluent, an organic or inorganic filler, a levelling agent, a surfactant, an anti-foaming agent, a thickener, a flame retardant, a surface modifier, a penetration accelerator, a moisturizing agent, a fixing agent, a fungicide, a preservative, an antioxidant, an ultraviolet absorber, a chelating agent, a pH adjusting agent, a stabilizer, a lubricant or a plasticizer.

(Polymerization Method)

The photo-cured product is obtained by irradiating the photopolymerizable composition of the present invention with light to be polymerized. In a case where the photopolymerizable composition is irradiated with light and polymerized to be photo-cured, the photopolymerizable composition may be formed into a film and photo-cured, or may be formed in a block and photo-cured. The photopolymerizable composition as droplets of a UV ink may be applied to the substrate and photo-cured. In a case where it is formed into a film and photo-cured, the photopolymerizable composition which is in a liquid form is applied to a substrate such as a polyester film to a film thickness of from 5 to 300 micron by a bar coater or the like. Otherwise, it may be applied in a smaller or larger film thickness by spin coating method or screen printing method.

A coating film formed of the photopolymerizable composition thus prepared is irradiated with energy rays (ultraviolet rays) within a wavelength range of from 300 nm to 500 nm at an intensity of from about 1 to about 1,000 mW/cm$^2$ to obtain a photo-cured product. The light source used may, for example, be a high pressure mercury lamp, an ultrahigh pressure mercury lamp, a metal halide lamp, a xenon lamp, a gallium-doped lamp, black light, a 405 nm ultraviolet LED, a 395 nm ultraviolet LED, a 385 nm ultraviolet LED, a 365 nm ultraviolet LED, a semiconductor laser, a blue LED, a white LED, or D bulb or V bulb manufactured by FUSION. Natural light such as sunlight may be used. The photopolymerizable composition is characterized by having a sensitizing effect even to light in a long wavelength range of from 365 nm to 405 nm, such as a 405 nm ultraviolet LED, a 395 nm ultraviolet LED, a 385 nm ultraviolet LED, a 375 nm ultraviolet LED, or a 365 nm ultraviolet LED, and preferred as an irradiation source is an ultraviolet LED or a semiconductor laser with a center wavelength of 365 nm, 375 nm, 385 nm, 395 nm or 405 nm.

(Photo DSC Measurement)

In the present invention, as a means to quantitatively evaluate the photopolymerization rate of the photopolymerizable composition under irradiation with light, photo DSC measurement is employed. According to this means, while a sample is directly irradiated with light, the heating value accompanying curing can be continuously and easily measured. When a sample set to a photo DSC measurement apparatus is irradiated with light, photo-curing reaction starts, and heat generation is observed. The baseline of a DSC curve which is horizontal before photo-curing shifts toward the exothermic side, and after the reaction is completed, it returns to the original baseline position. The heating value can be obtained from the intensity of the peak of the DSC curve. That is, by irradiating the photopolymerizable composition with light and measuring and comparing the heating value per 1 mg, the progress of the polymerization can be evaluated.

(Observation of Polymerization Behavior by Photo Rheometer)

Whether the polymerization reaction proceeds or not may be confirmed also by whether the viscosity of the composition increases or not. This is a means to confirm progress of the polymerization reaction by measuring the change with time of the complex viscosity by a photo rheometer.

(Judgement of Migration Resistance of Composition)

As a method to judge whether the photopolymerization sensitizer contained in the photopolymerization composition of the present invention migrates to the film or the like or not, a photopolymerizable composition comprising the photopolymerization sensitizer is applied to a thin film, which is covered with a polyethylene film and stored at a constant temperature (26° C.) for a constant period, and then the polyethylene film is peeled, and whether the photopolymerization sensitizer migrates to the polyethylene film or not is evaluated, to judge the migration resistance. The peeled polyethylene film is washed with acetone to remove the composition on the surface and dried, an UV spectrum of the polyethylene film is measured, and an increase of the absorption intensity resulting from the photopolymerization sensitizer is examined to measure the migration resistance. For this measurement, an UV/visible spectrophotometer (manufactured by SHIMADZU CORPORATION, model: UV2600) is used. For quantitative comparison with 9,10-dibutoxyanthracene which is a compound in Comparative Examples, the obtained absorbance is calculated as an absorbance of 9,10-dibutoxyanthracene. For calculation, absorbances of the compound of the present invention and 9,10-dibutoxyanthracene at 260 nm are measured by the ultraviolet/visible spectrophotometer, and the respective molar absorption coefficients are obtained from the absorbances and the molar concentrations, and calculation is made using their ratio.

EXAMPLES

Now, the present invention will be described in further detail with reference to Examples. However, Examples are merely exemplified as examples. That is, the following Examples are not exhaustive nor intended to restrict the present invention as described. Accordingly, the present invention is by no means restricted to the following Examples within a range not to exceed the scope of the present invention. Further, unless otherwise specified, all the parts and percentages are based on the weight.

The compounds of the present invention were identified using the following apparatus.

Infrared (IR) spectrophotometer: manufactured by Thermo Fisher Scientific, model is 50

FT-IR nuclear magnetic resonance (NMR) apparatus: manufactured by JEOL Ltd., model ECS-400

Melting point: melting point measuring apparatus manufactured by Gallenkamp, model MFB-595 (in accordance with JIS K0064)

Preparation Ex. 1

Preparation of 9,10-dihydroxyanthracene

Into a 50 ml four-necked flask equipped with a stirrer and a thermometer, in a nitrogen atmosphere, 1.0 g (4.8 mmol) of 9,10-anthraquinone, 10 g of acetic acid as a solvent and 0.6 g (9.6 mmol) of zinc powder were added, followed by stirring at room temperature for 3.5 hours. Zinc powder was removed by filtration, and water was added to the filtrate, whereupon crystals precipitated. The crystals were collected by suction filtration and dried to obtain 0.7 g (crude yield: 70 mol %) of yellow green crystals.

(1) IR (cm$^{-1}$): 3291, 1676, 1618, 1388, 1326, 1137, 1050, 755, 692, 624, 545.

(2) $^1$H-NMR (400 MHz, DMSO-d$_6$): δ=7.382-7.450 (m, 4H), 8.318-8.335 (m, 4H), 9.404-9.424 (m, 2H).

Preparation Example 1

Preparation of 9,10-bis(methoxycarbonylmethyleneoxy)anthracene (1-1)

Into a 100 ml four-necked flask equipped with a stirrer and a thermometer, in a nitrogen atmosphere, 15 g of methyl isobutyl ketone as a solvent, 0.8 g (1.2 mmol) of a 50% aqueous solution of tetrabutylammonium bromide as a catalyst, and 9.5 g (62.1 mmol) of methyl bromoacetate were added. While the temperature of the reaction system was kept at from 20 to 25° C., 29.1 g (24 mmol as anthraquinone) of a 17 wt % aqueous solution of 9,10-dihydroxyanthracene disodium salt was dropwise added over a period of at least 1 hour. After completion of the dropwise addition, the mixture was stirred further for 1 hour. Then, by suction filtration, 4.7 g (crude yield: 55 mol %) of yellow crystals were obtained.

(1) Melting point: 151-152° C.

(2) IR (cm$^{-1}$): 1745, 1391, 1363, 1164, 1093, 774, 705.

(3) $^1$H-NMR (400 MHz, CDCl$_3$): δ=3.914 (s, 6H), 4.792 (s, 4H), 7.261-7.545 (m, 4H), 8.319-8.366 (m, 4H).

Preparation Example 2

Preparation of 9,10-bis(ethoxycarbonylmethyleneoxy)anthracene (1-2)

Into a 100 ml four-necked flask equipped with a stirrer and a thermometer, in a nitrogen atmosphere, 15 g of methyl isobutyl ketone as a solvent, 0.8 g (1.2 mmol) of a 50% aqueous solution of tetrabutylammonium bromide as a catalyst, and 10.4 g (62.5 mmol) of ethyl bromoacetate were added. While the temperature of the reaction system was kept at from 20 to 25° C., 29.1 g (24 mmol as anthraquinone) of a 17 wt % aqueous solution of 9,10-dihydroxyanthracene disodium salt was dropwise added over a period of at least 1 hour. After completion of the dropwise addition, the mixture was stirred further for 1 hour. Then, by suction filtration, 5.0 g (crude yield: 55 mol %) of pale yellow crystals were obtained.

(1) Melting point: 93-94° C.

(2) IR (cm$^{-1}$): 1754, 1742, 1382, 1367, 1241, 1212, 1168, 1087, 1034, 1004, 936, 809, 768, 720, 691, 669, 585.

(3) $^1$H-NMR (400 MHz, CDCl$_3$): δ=1.370 (t, J=14 Hz, 6H), 4.376 (k, J=21.6 Hz, 4H), 4.777 (s, 4H), 7.261-7.540 (m, 4H).

Preparation Example 3

Preparation of 9,10-bis(isopropoxycarbonylmethyleneoxy)anthracene (1-3)

Into a 100 ml four-necked flask equipped with a stirrer and a thermometer, in a nitrogen atmosphere, 15 g of methyl isobutyl ketone as a solvent, 0.8 g (1.2 mmol) of a 50% aqueous solution of tetrabutylammonium bromide as a catalyst, and 11.3 g (62.5 mmol) of isopropyl bromoacetate were added. While the temperature of the reaction system was kept at from 20 to 25° C., 29.1 g (24 mmol as anthraquinone) of a 17 wt % aqueous solution of 9,10-dihydroxyanthracene disodium salt was dropwise added over a period of at least 1 hour. After completion of the dropwise addition, the mixture was stirred further for 1 hour. Then, by suction filtration, 5.9 g (crude yield: 60 mol %) of pale yellow crystals were obtained.

(1) Melting point: 109-110° C.

(2) IR (cm$^{-1}$): 1744, 1360, 1210, 1163, 1086, 1018, 1004, 776, 768, 671.

(3) $^1$H-NMR (400 MHz, CDCl$_3$): δ=1.347 (d, J=6.4 Hz, 12H), 4.743 (s, 4H), 5.246-5.277 (m, 2H), 7.504-7.529 (m, 4H), 8.356-8.398 (m, 4H).

Preparation Example 4

Preparation of 9,10-bis(tert-butoxycarbonylmethyleneoxy)anthracene (1-4)

Into a 100 ml four-necked flask equipped with a stirrer and a thermometer, in a nitrogen atmosphere, 15 g of methyl isobutyl ketone as a solvent, 0.8 g (1.2 mmol) of a 50% aqueous solution of tetrabutylammonium bromide as a catalyst, and 12.2 g (62.5 mmol) of tert-butyl bromoacetate were added. While the temperature of the reaction system was kept at from 20 to 25° C., 29.1 g (24 mmol as anthraquinone) of a 17 wt % aqueous solution of 9,10-dihydroxyanthracene disodium salt was dropwise added over a period of at least 1 hour. After completion of the dropwise addition, the mixture was stirred further for 1 hour. Then, anthraquinone was removed by suction filtration, and the obtained filtrate was left to stand overnight to precipitate crystals. The crystals were collected by suction filtration to obtain 6.5 g (crude yield: 61 mol %) of pale yellow crystals.

(1) Melting point: 131-132° C.

(2) IR (cm$^{-1}$): 1742, 1391, 1358, 1232, 1151, 1089, 1021, 1004, 846, 776, 749, 670.

(3) $^1$H-NMR (400 MHz, CDCl$_3$): δ=1.575 (s, 18H), 4.659 (s, 4H), 7.260-7.530 (m, 4H), 8.359-8.400 (m, 4H).

Preparation Example 5

Preparation of 9,10-bis(n-butoxycarbonylmethyleneoxy)anthracene (1-5)

Into a 100 ml four-necked flask equipped with a stirrer and a thermometer, in a nitrogen atmosphere, 15 g of methyl isobutyl ketone as a solvent, 3.1 g (4.8 mmol) of a 50% aqueous solution of tetrabutylammonium bromide as a catalyst, and 9.4 g (62.5 mmol) of n-butyl chloroacetate were added. While the temperature of the reaction system was kept at from 20 to 25° C., 29.1 g (24 mmol as anthraquinone) of a 17 wt % aqueous solution of 9,10-dihydroxyanthracene disodium salt was dropwise added over a period of at least 1 hour. After completion of the dropwise addition, the mixture was stirred further for 1 hour. Then, anthraquinone was removed by suction filtration, and the obtained filtrate was washed twice with water. After washing with water, anthraquinone precipitated, which was removed by suction filtration. The filtrate was left to stand overnight to precipitate crystals, which were collected by suction filtration to obtain 5.5 g (crude yield: 52 mol %) of yellow crystals.

(1) Melting point: 71-72° C.

(2) IR (cm$^{-1}$): 1749, 1411, 1385, 1364, 1246, 1226, 1167, 1085, 1035, 1018, 957, 768, 721, 669, 587.

(3) $^1$H-NMR (400 MHz, CDCl$_3$): δ=0.967 (d, J=15.2 Hz, 6H), 1.387-1.481 (m, 4H), 1.678-1.750 (m, 4H), 4.317 (t, J=13.2 Hz, 4H), 4.779 (s, 4H), 7.508-7.826 (m, 4H), 8.319-8.377 (m, 4H).

Preparation Example 6

Preparation of 9,10-bis(methoxycarbonylmethylmethyleneoxy)anthracene (1-6)

Into a 100 ml four-necked flask equipped with a stirrer and a thermometer, in a nitrogen atmosphere, 15 g of methyl isobutyl ketone as a solvent, 0.8 g (1.2 mmol) of a 50% aqueous solution of tetrabutylammonium bromide as a catalyst, and 10.4 g (62.5 mmol) of methyl 2-bromopropionate were added. While the temperature of the reaction system was kept at from 20 to 25° C., 29.1 g (24 mmol as anthraquinone) of a 17 wt % aqueous solution of 9,10-dihydroxyanthracene disodium salt was dropwise added over a period of at least 1 hour. After completion of the dropwise addition, the mixture was stirred further for 1 hour. Then, anthraquinone was removed by suction filtration, and the obtained filtrate was washed twice with water by liquid separation. The solution was concentrated by an evaporator and cooled in a freezer to precipitate crystals. The crystals were collected by suction filtration to obtain 4.6 g (crude yield: 50 mol %) of yellow crystals.

(1) Melting point: 130-131° C.
(2) IR (cm$^{-1}$): 1737, 1366, 1207, 1134, 1078, 1061, 1020, 970, 748, 681.
(3) $^1$H-NMR (400 MHz, CDCl$_3$): δ=1.644 (d, J=6.4 Hz, 6H), 3.770 (s, 6H), 4.904 (k, J=20.4 Hz, 2H), 7.464-7.489 (m, 4H), 8.292-8.332 (m, 4H).

Preparation Example 7

Preparation of 9,10-bis(ethoxycarbonylpropyleneoxy)anthracene (1-7)

Into a 100 ml four-necked flask equipped with a stirrer and a thermometer, in a nitrogen atmosphere, 0.77 g (1.19 mmol) of a 50% aqueous solution of tetrabutylammonium bromide as a catalyst, 12.1 g (61.8 mmol) of ethyl 4-bromobutylate, 5.0 g (23.8 mmol) of 9,10-dihyroxyanthracene, 9.9 g (71.4 mmol) of potassium carbonate and 40 g of N,N-dimethylformamide as a solvent were added.

While the temperature of the reaction system was kept at from 20 to 30° C., the mixture was stirred for 1 hour. Then, anthraquinone was removed by suction filtration, and the obtained filtrate was dissolved in toluene and washed twice with water. The solution was concentrated by an evaporator. The concentrate was left to stand overnight, whereupon the entire solution was solidified, to which methanol was added, followed by heating at 50° C. for dissolution. Undissolved anthraquinone was removed by suction filtration, and the filtrate was cooled in a freezer to precipitate crystals. The crystals were collected by suction filtration to obtain 5.4 g (crude yield: 51 mol %) of yellow crystals.

(1) Melting point: 95-96° C.
(2) IR (cm$^{-1}$): 1721, 1351, 1312, 1239, 1183, 1164, 1081, 1024, 1015, 913, 767, 742, 669.
(3) $^1$H-NMR (400 MHz, CDCl$_3$): δ=1.307 (t, J=14.0 Hz, 6H), 2.340-2.408 (m, 4H), 2.776 (t, J=14.8 Hz, 4H), 4.171-4.235 (m, 8H), 7.456-7.494 (m, 4H), 8.230-8.256 (m, 4H).

Preparation Example 8

Preparation of 9,10-bis(ethoxycarbonylbutyleneoxy)anthracene (1-8)

Into a 100 ml four-necked flask equipped with a stirrer and a thermometer, in a nitrogen atmosphere, 0.77 g (1.19 mmol) of a 50% aqueous solution of tetrabutylammonium bromide as a catalyst, 12.9 g (61.8 mmol) of ethyl 5-bromovalerate, 5.0 g (23.8 mmol) of 9,10-dihydroxyanthracene, 9.9 g (71.4 mmol) of potassium carbonate and 40 g of N,N-dimethylformamide as a solvent were added. While the temperature of the reaction system was kept at from 20 to 30° C., the mixture was stirred for 1 hour. Then, anthraquinone was removed by suction filtration, and the obtained filtrate was dissolved in toluene and washed twice with water by liquid separation. The solution was concentrated by an evaporator. The concentrate was left to stand overnight, methanol was added, and undissolved anthraquinone was removed by suction filtration. The filtrate was cooled in a freezer to precipitate crystals. The crystals were collected by suction filtration to obtain 6.2 g (crude yield: 55 mol %) of orange crystals.

(1) Melting point: 57-58° C.
(2) IR (cm$^{-1}$): 1722, 1403, 1337, 1284, 1269, 1229, 1178, 1167, 1068, 1021, 934, 763, 675.
(3) $^1$H-NMR (400 MHz, CDCl$_3$): δ=1.286 (t, J=14.4 Hz, 6H), 2.018-2.103 (m, 8H), 2.496 (t, J=13.6 Hz, 4H), 4.151-4.205 (m, 8H), 7.463-7.487 (m, 4H), 8.243-8.268 (m, 4H).

Preparation Example 9

Preparation of 2-ethyl-9,10-bis(isopropoxycarbonylmethyleneoxy)anthracene (1-9)

Into a 200 ml four-necked flask equipped with a stirrer and a thermometer, in a nitrogen atmosphere, 5.0 g (21.2 mmol) of 2-ethylanthraquionone, 9.1 g (86.4 mmol) of thiourea dioxide, 8.4 g (211.6 mmol) of sodium hydroxide and 50 g of deionized water were added, followed by stirring while gradually heating to 120° C. Stirring was stopped when the solution become reddish black, and the solution was cooled at room temperature to prepare an aqueous solution of 2-ethyl-9,10-dihydroxyanthracene disodium salt. Then, into another 200 ml four-necked flask equipped with a stirrer and a thermometer, in a nitrogen atmosphere, 15 g of methyl isobutyl ketone as a solvent, 2.7 g (4.23 mmol) of a 50% aqueous solution of tetrabutylammonium bromide as a catalyst, 10.0 g (55.0 mmol) of isopropyl bromoacetate were added. While the temperature of the reaction system was kept at from 20 to 25° C., the above prepared aqueous solution of 2-ethyl-9,10-anthracenediol disodium salt was dropwise added over a period of at least 1 hour. After completion of the dropwise addition, the mixture was stirred further for 1 hour. Then, the aqueous layer was removed, and the organic layer was concentrated by an evaporator to obtain 4.5 g (crude yield: 48 mol %) of an orange oil.

(1) Melting point: liquid at room temperature
(2) IR (cm$^{-1}$): 1728, 1673, 1454, 1385, 1373, 1324, 1286, 1206, 1085, 962, 931, 901, 825, 772, 750, 712.
(3) $^1$H-NMR (400 MHz, CDCl$_3$): δ=1.237-1.371 (m, 15H), 2.816-2.899 (m, 2H), 4.731 (s, 4H), 5.014-5.123 (m, 1H), 5.225-5.301 (m, 1H), 7.391 (d, J=9.2 Hz, 1H), 7.461-7.512 (m, 2H), 7.766-7.790 (m, 1H), 8.119 (d, J=7.6 Hz, 1H), 8.284-8.368 (m, 2H).

Intermediate Preparation Ex

Preparation of
9,10-bis(hydroxycarbonylmethyleneoxy)anthracene
(Preparation of Intermediate of the Formula (5))

Into a 300 ml four-necked flask equipped with a stirrer and a thermometer, in a nitrogen atmosphere, 95 g of methyl isobutyl ketone (MIBK) as a solvent, 4.4 g (6.8 mmol) of a 50% aqueous solution of tetrabutylammonium bromide (TBAB) as a catalyst and 49.5 g (356 mmol) of bromoacetic acid were added. While the temperature of the reaction system was kept at from 20 to 30° C., an aqueous solution having 165.7 g (137 mmol) of 9,10-dihydroxyanthracene disodium salt (AHQ-Na) and sodium hydroxide, 11.4 g (285 mmol) of sodium hydroxide and 20 g of deionized water mixed was dropwise added over a period of 3 hours. After completion of the dropwise addition, the mixture was stirred further for 1.5 hours. Then, unreacted materials, etc. were removed by suction filtration, and 100 ml of toluene was added for extraction. The organic layer was removed, and 28.9 g (285 mmol) of 35% hydrochloric acid was added to the aqueous layer to precipitate crystals. The precipitated crystals were collected by filtration, washed with water and dried to obtain 33.3 g (yield: 75 mol %) of yellow crystals.

(1) Melting point: at least 250° C.
(2) IR ($cm^{-1}$): 1727, 1435, 1377, 1254, 1240, 1091, 934, 769, 592, 657.
(3) $^1$H-NMR (400 MHz, $CDCl_3$): δ=1.631 (br, 2H), 4.754 (br, 4H), 7.802-7.825 (m, 4H), 8.317-8.340 (m, 4H)

Preparation Example 10

Preparation of
9,10-bis(ethoxycarbonylmethyleneoxy)anthracene
(1-1) (Reaction with Alcohol)

Into a 1,000 ml four-necked flask equipped with a stirrer and a thermometer, in a nitrogen atmosphere, 78.7 g (241 mmol) of 9,10-bis(hydroxycarbonylmethyleneoxy)anthracene obtained in (Intermediate Preparation Ex.), 236.0 g (5,119 mmol) of ethanol and 3.9 g (39 mmol) of concentrated sulfuric acid were added. While the temperature of the reaction system was kept at from 75 to 80° C. and water as a by-product was withdrawn together with ethanol, the mixture was stirred for 10 hours. The mixture was cooled, and the precipitated crystals were collected by suction filtration, washed with methanol and dried to obtain 71.7 g (yield: 78 mol %) of yellow crystals.

(1) Melting point: 93-94° C.
(2) IR ($cm^{-1}$): 1754, 1742, 1382, 1367, 1241, 1212, 1168, 1087, 1034, 1004, 936, 809, 768, 720, 691, 669, 585.
(3) $^1$H-NMR (400 MHz, $CDCl_3$): δ=1.370 (t, J=14 Hz, 6H), 4.376 (k, J=21.6 Hz, 4H), 4.777 (s, 4H), 7.261-7.540 (m, 4H).

Preparation Example 11

Preparation of
9,10-bis(propoxycarbonylmethyleneoxy)anthracene
(Reaction with Alcohol)

Into a 50 ml four-necked flask equipped with a stirrer and a thermometer, in a nitrogen atmosphere, 0.4 g (1.2 mmol) of 9,10-bis(hydroxycarbonylmethyleneoxy)anthracene obtained in (Intermediate Preparation Ex.), 1.5 g (25 mmol) of 1-propanol and 0.01 g (0.1 mmol) of methanesulfonic acid were added. While the temperature of the reaction system was kept at from 50 to 60° C., the mixture was stirred for 1.5 hours. Then, insoluble matters were removed by filtration, and methanol and deionized water were added to the filtrate to precipitate crystals. The crystals were collected by suction filtration, washed with methanol and dried to obtain 0.12 g (crude yield: 25 mol) of yellow crystals.

(1) Melting point: 75-76° C.
(2) IR ($cm^{-1}$): 2950, 1747, 1400, 1380, 1359, 1206, 1162, 776.
(3) $^1$H-NMR (400 MHz, $CDCl_3$): δ=0.992 (t, J=7.3 Hz, 6H), 1.744 (tq, J=6.9 Hz, 7.3 Hz, 4H), 4.272 (t, J=6.9 Hz, 4H), 4.785 (s, 4H), 7.496-7.534 (m, 4H), 8.349-8.411 (m, 4H).

Preparation Example 12

Preparation of
9,10-bis(n-butoxycarbonylmethyleneoxy)anthracene
(1-5) (Reaction with Alcohol)

Into a 300 ml four-necked flask equipped with a stirrer and a thermometer, in a nitrogen atmosphere, 34.2 g (105 mmol) of 9,10-bis(hydroxycarbonylmethyleneoxy)anthracene obtained in (Intermediate Preparation Ex.), 172.7 g (2,330 mmol) of 1-butanol and 1.7 g (17 mmol) of concentrated sulfuric acid were added. While the temperature of the reaction system was kept at from 120 to 130° C. and water as a by-product was withdrawn, the mixture was stirred for 14 hours. The mixture was cooled, and the precipitated crystals were collected by suction filtration, washed with methanol and dried to obtain 26.5 g (yield: 58 mol %) of yellow crystals.

(1) Melting point: 71-72° C.
(2) IR ($cm^{-1}$): 1749, 1411, 1385, 1364, 1246, 1226, 1167, 1085, 1035, 1018, 957, 768, 721, 669, 587.
(3) $^1$H-NMR (400 MHz, $CDCl_3$): δ=0.967 (d, J=15.2 Hz, 6H), 1.387-1.481 (m, 4H), 1.678-1.750 (m, 4H), 4.317 (t, J=13.2 Hz, 4H), 4.779 (s, 4H), 7.508-7.826 (m, 4H), 8.319-8.377 (m, 4H).

Preparation Example 13

Preparation of 9,10-bis(2-hydroxyethoxycarbonylmethyleneoxy)anthracene (1-11) (Reaction with Alcohol)

Into a 50 ml four-necked flask equipped with a stirrer and a thermometer, in a nitrogen atmosphere, 0.65 g (2.0 mmol) of 9,10-bis(hydroxycarbonylmethyleneoxy)anthracene obtained in (Intermediate Preparation Ex.), 3.0 g (48 mmol) of ethylene glycol and 0.2 g (2.1 mmol) of methanesulfonic acid were added. While the temperature of the reaction system was kept at from 50 to 60° C., the mixture was stirred for 4 hours. After the mixture was cooled, methanol and deionized water were added to precipitate crystals. The crystals were collected by suction filtration, washed with methanol and dried to obtain 0.47 g (yield: 57 mol %) of yellow crystals.

(1) Melting point: 145-146° C.
(2) IR ($cm^{-1}$): 3505, 2950, 1733, 1674, 1578, 1077.
(3) $^1$H-NMR (400 MHz, $CDCl_3$): δ=3.804 (br., 4H), 4.340 (t, J=5.0 Hz, 4H), 4.905 (s, 4H), 7.552-7.584 (m, 4H), 8.447-8.478 (m, 4H).

Preparation Example 14

Preparation of
9,10-bis(n-butoxycarbonylmethyleneoxy)anthracene
(1-5) (Reaction with Halogenated Alkyl)

Into a 100 ml four-necked flask equipped with a stirrer and a thermometer, 2.0 g (6.2 mmol) of 9,10-bis(hydroxycarbonylmethyleneoxy)anthracene obtained in (Intermediate Preparation Ex.), 43.4 g of N,N'-dimethylformamide as a solvent and 0.87 g (6.4 mmol) of potassium carbonate were added, and the system was replaced with nitrogen. In a nitrogen atmosphere, 3.87 g (28.2 mmol) of n-butyl bromide was added, and the mixture was stirred with heating in a water bath at 60° C. After completion of the reaction, the mixture was cooled to room temperature, and the residue containing potassium carbonate was removed by suction filtration. The obtained filtrated was poured into water, extraction with 45.6 g of toluene was conducted, and the toluene layer was washed with water. The washed toluene layer was vacuum concentrated by an evaporator to obtain 2.28 g (crude yield: 83.6 mol %) of orange crystals.

(1) Melting point: 71-72° C.
(2) IR (cm$^{-1}$): 1749, 1411, 1385, 1364, 1246, 1226, 1167, 1085, 1035, 1018, 957, 768, 721, 669, 587.
(3) $^1$H-NMR (400 MHz, CDCl$_3$): δ=0.967 (d, J=15.2 Hz, 6H), 1.387-1.481 (m, 4H), 1.678-1.750 (m, 4H), 4.317 (t, J=13.2 Hz, 4H), 4.779 (s, 4H), 7.508-7.826 (m, 4H), 8.319-8.377 (m, 4H).

Preparation Example 15

Preparation of
9,10-bis(ethoxycarbonylmethyleneoxy)anthracene
(1-2)

Into a 300 ml four-necked flask equipped with a stirred and a thermometer, in a nitrogen atmosphere, 50 g of o-xylene as a solvent, 29 g (45 mmol) of a 50% aqueous solution of tetrabutylammonium bromide as a catalyst and 33.1 g (270 mmol) of ethyl chloroacetate were added. While the temperature of the reaction system was kept at from 50 to 55° C., 100 g (90 mmol as anthraquinone) of a 18.8 wt % aqueous solution of 9,10-dihydroxyanthracene disodium salt was dropwise added over a period of one hour. After completion of the dropwise addition, the mixture was stirred further for one hour. Then, insoluble matters were removed by suction filtration, and the filtrate was cooled to 10° C., whereupon crystals precipitated. The crystals were collected by suction filtration and dried to obtain 5.0 g (crude yield: 42 mol %) of pale yellow crystals.

(1) Melting point: 93-94° C.
(2) IR (cm$^{-1}$): 1754, 1742, 1382, 1367, 1241, 1212, 1168, 1087, 1034, 1004, 936, 809, 768, 720, 691, 669, 585.
(3) $^1$H-NMR (400 MHz, CDCl$_3$): δ=1.370 (t, J=14 Hz, 6H), 4.376 (k, J=21.6 Hz, 4H), 4.777 (s, 4H), 7.261-7.540 (m, 4H).

Preparation Example 16

Preparation of
9,10-bis(n-butoxycarbonylmethyleneoxy)anthracene
(1-5)

Into a 200 ml four-necked flask equipped with a stirred and a thermometer, in a nitrogen atmosphere, 20.0 g (144 mmol) of bromoacetic acid, 21.3 g (287 mmol) of n-butanol, 35.0 g of o-xylene as a solvent and 1.0 g (10 mmol) of sulfuric acid as a catalyst were added. While the temperature of the reaction system was kept at from 120 to 130° C. and azeotropic water was removed, the mixture was stirred for one hour. After cooling to room temperature, an aqueous sodium hydrogen carbonate solution was added for neutralization and the aqueous layer was removed. 1.8 g (2.8 mmol) of a 50% aqueous solution of tetrabutylammonium bromide as a catalyst was added, and while the temperature of the reaction system was kept at from 20 to 35° C., 61.5 g (55 mmol of anthraquinone) of a 18.7 wt % aqueous solution of 9,10-dihydroxyanthracene disodium salt was dropwise added over a period of one hour. After completion of the dropwise addition, the mixture was stirred further for one hour. Then, anthraquinone was removed by suction filtration, and the obtained filtrated was washed twice with water. Anthraquinone precipitated, which was removed by suction filtration, and the filtrate was washed with water and concentrated. Methanol was added to the concentrate for crystallization, and the precipitated crystals were collected by suction filtration and dried to obtain 16.1 g (crude yield: 66 mol %) of yellow crystals.

(1) Melting point: 71-72° C.
(2) IR (cm$^{-1}$): 1749, 1411, 1385, 1364, 1246, 1226, 1167, 1085, 1035, 1018, 957, 768, 721, 669, 587.
(3) $^1$H-NMR (400 MHz, CDCl$_3$): δ=0.967 (d, J=15.2 Hz, 6H), 1.387-1.481 (m, 4H), 1.678-1.750 (m, 4H), 4.317 (t, J=13.2 Hz, 4H), 4.779 (s, 4H), 7.508-7.826 (m, 4H), 8.319-8.377 (m, 4H).

Preparation Example 17

Preparation of
9,10-bis(isopropoxycarbonylmethyleneoxy)anthracene
(1-3)

Into a 300 ml four-necked flask equipped with a stirrer and a thermometer, in a nitrogen atmosphere, 32.5 g (234 mmol) of bomoacetic acid, 28.1 g (467 mmol) of i-propanol, 75.0 g of o-xylene as a solvent and 1.5 g (16 mmol) of sulfuric acid as a catalyst were added. While the temperature of the reaction system was kept at from 100 to 110° C. and the distillate (i-propanol containing by-product water) was removed, the mixture was stirred for one hour. Further, 28.0 g (466 mmol) of i-propanol was added, followed by stirring for 2 hours. The mixture was cooled to room temperature, an aqueous sodium hydrogen carbonate solution was added for neutralization, and the aqueous layer was removed. 2.8 g (4.3 mmol) of a 50% aqueous solution of tetrabutylammonium bromide as a catalyst was added to the organic layer, and while the temperature of the reaction system was kept at from 30 to 40° C., 100 g (90 mmol as anthraquinone) of a 18.7 wt % aqueous solution of 9,10-dihydroxyanthracene disodium salt was dropwise added over a period of one hour. Then, anthraquinone was removed by suction filtration, and the aqueous layer of the obtained filtrate was removed. Concentration was conducted, and methanol was added to the obtained concentrate for crystallization, and the precipitated crystals were collected by suction filtration and dried to obtain 17.6 g (crude yield: 45 mol %) of cream crystals.

(1) Melting point: 109-110° C.
(2) IR (cm$^{-1}$): 1744, 1360, 1210, 1163, 1086, 1018, 1004, 776, 768, 671.
(3) $^1$H-NMR (400 MHz, CDCl$_3$): δ=1.347 (d, J=6.4 Hz, 12H), 4.743 (s, 4H), 5.246-5.277 (m, 2H), 7.504-7.529 (m, 4H), 8.356-8.398 (m, 4H).

Preparation Example 18

Preparation of 9,10-bis(n-pentyloxycarbonylmethyleneoxy)anthracene (1-11)

Into a 300 ml four-necked flask equipped with a stirrer and a thermometer, in a nitrogen atmosphere, 32.5 g (234 mmol) of bromoacetic acid, 41.1 g (466 mmol) of n-pentanol, 75.7 g of o-xylene as a solvent and 1.5 g (16 mmol) of sulfuric acid as a catalyst were added. While the temperature of the reaction system was kept at from 140 to 150° C. and azeotropic water was removed, the mixture was stirred for 2 hours. After the mixture was cooled to room temperature, an aqueous sodium hydrogen carbonate solution was added for neutralization, and the aqueous layer was removed. 2.8 g (4.3 mmol) of a 50% aqueous solution of tetrabutylammonium bromide as a catalyst was added to the organic layer, and while the temperature of the reaction system was kept at from 20 to 30° C., 100 g (90 mmol as anthraquinone) of a 18.7 wt % aqueous solution of 9,10-dihydroxyanthracene disodium salt was dropwise added over a period of one hour. After completion of the dropwise addition, the mixture was stirred further for one hour, and the mixture was heated to 55 to 60° C., followed by stirring for one hour. After the mixture was cooled to room temperature, liquid separation and washing twice with water were conducted, anthraquinone was removed by suction filtration, and concentration was conducted. Ethanol was added to the concentrate for crystallization, and the precipitated crystals were collected by suction filtration and dried to obtain 26.6 g (crude yield: 57 mol %) of pale yellow crystals.

(1) Melting point:109-111° C.
(2) IR (cm$^{-1}$): 2693, 2922, 2855, 1750, 1470, 1436, 1381, 1368, 1356, 1274, 1200, 1164, 1052, 1006, 976, 951, 780, 711, 677, 608, 581, 400.
(3) $^1$H-NMR (400 MHz, CDCl$_3$): δ=0.921 (t, J=12.8 Hz, 6H), 1.363-1.396 (m, 8H), 1.696-1.747 (m, 4H), 4.306 (t, J=13.2 Hz, 4H), 4.780 (s, 4H), 7.505-7.536 (m, 4H), 8.356-8.387 (m, 4H).

Preparation Example 19

Preparation of 9,10-bis(cyclohexyloxycarbonylmethyleneoxy)anthracene (1-12)

Into a 300 ml four-necked flask equipped with a stirrer and a thermometer, in a nitrogen atmosphere, 32.4 g (234 mmol) of bromoacetic acid, 46.8 g (467 mmol) of cyclohexanol, 75.0 g of o-xylene as a solvent and 1.5 g (15 mmol) of sulfuric acid as a catalyst were added. While the temperature of the reaction system was kept at from 140 to 150° C. and azeotropic water was removed, the mixture was stirred for 2 hours. After the mixture was cooled to room temperature, an aqueous sodium hydrogen carbonate solution was added for neutralization, and the aqueous layer was removed. 2.8 g (4.4 mmol) of a 50% aqueous solution of tetrabutylammonium bromide as a catalyst was added to the organic layer, and while the temperature of the reaction system was kept at from 35 to 40° C., 100 g (90 mmol as anthraquinone) of a 18.7 wt % aqueous solution of 9,10-dihydroxyanthracene disodium salt was dropwise added over a period of one hour. After completion of the dropwise addition, the mixture was stirred further for one hour, and the mixture was heated to 55 to 60° C. and stirred for one hour. After cooling to room temperature, anthraquinone was removed by suction filtration, and liquid separation, washing with water twice, and concentration were conducted. Methanol was added to the concentrate for crystallization, and the precipitated crystals were collected by suction filtration and dried to obtain 25.5 g (crude yield: 54 mol %) of pale yellow crystals.

(1) Melting point: 122-124° C.
(2) IR (cm$^{-1}$): 2930, 2857, 1745, 1677, 1621, 1453, 1438, 1399, 1369, 1360, 1206, 1168, 1086, 1035, 1006, 954, 922, 891, 813, 715, 693, 672, 659, 608, 585, 455.
(3) $^1$H-NMR (400 MHz, CDCl$_3$): δ=1.239-1.596 (m, 12H), 1.754-1.786 (m, 4H), 1.939-1.961 (m, 4H), 4.760 (s, 4H), 4.985-5.050 (m, 2H), 7.501-7.526 (m, 4H), 8.372-8.398 (m, 4H).

Preparation Example 20

Preparation of 9,10-bis(isopropoxycarbonylmethyleneoxy)anthracene (1-3)

Into a 300 ml Erlenmeyer flask in which a stirrer was put, in a nitrogen atmosphere, 5.0 g (24.0 mmol) of 9,10-anthraquinone, 10.0 g of o-xylene, 10.4 g (59.7 mmol) of hydrosulfite, 4.8 g (120 mmol) of sodium hydroxide and 57.3 g of deionized water were put, followed by stirring at room temperature for one hour. The aqueous solution of 9,10-dihydroxyanthracene disodium salt thus prepared was transferred to a 100 ml dropping funnel.

Into a 200 ml four-necked flask equipped with a stirrer and a thermometer, in a nitrogen atmosphere, 10.0 g of o-xylene, 0.8 g (1.2 mmol) of a 50% aqueous solution of tetrabutylammonium bromide as a catalyst and 13.0 g (71.8 mmol) of isopropyl bromoacetate were added, and while the temperature of the reaction system was kept at from 20 to 30° C., the aqueous solution of 9,10-dihydroxyanthracene disodium salt in the dropping funnel was dropwise added over a period of one hour. Then, anthraquinone and the like were removed by suction filtration, and the aqueous layer of the obtained filtrate was removed. The organic layer was washed once with deionized water and concentrated, and methanol was added to the concentrate for crystallization. The precipitated crystals were collected by suction filtration and dried to obtain 5.0 g (crude yield: 40 mol %) of cream crystals.

(1) Melting point:109-110° C.
(2) IR (cm$^{-1}$): 1744, 1360, 1210, 1163, 1086, 1018, 1004, 776, 768, 671.
(3) $^1$H-NMR (400 MHz, CDCl$_3$): δ=1.347 (d, J=6.4 Hz, 12H), 4.743 (s, 4H), 5.246-5.277 (m, 2H), 7.504-7.529 (m, 4H), 8.356-8.398 (m, 4H).

(Photo DSC Measurement)

In this Example, photo DSC measurement was carried out as follows. That is, XDSC-7200 manufactured by Hitachi High-Technologies Corporation was used as a DSC measurement apparatus, and a photo DSC measurement unit was attached thereto so that DSC measurement could be conducted while applying light. As a light source for light irradiation, LA-410UV manufactured by HAYASHI-REPIC CO., LTD. was used, and a band-pass filter was set so that 405 nm light was taken out and applied to a sample. The light illuminance was 50 mW/cm$^2$. Light from the light source was led up to the upper part of the sample by glass fibers, and the shutter of the light source was trigger-controlled so that the DSC measurement could be started simultaneously with the start of light irradiation. For photo DSC measurement, about 1 mg of a sample was accurately weighed in a measurement aluminum pan, which was put in a DSC measurement part, and the photo DSC unit was attached. Then, the interior of the measurement part was kept in a nitrogen atmosphere, the measurement part was left at rest for 10 minutes, and measurement was started. Measurement was continued for 6 minutes while ordinary light was applied. After the first measurement, measurement was conducted again under the same conditions while the sample was as it was, and a value obtained by subtracting the second measurement result from the first measurement result was taken as the measurement result of the sample. The result was based on the total heating value per 1 mg of a sample in one minute after light irradiation, unless otherwise specified. The photoreaction may not be completed in one minute depending upon the measurement conditions, however, the total heating value in one minute was employed to compare the reaction behavior at the initial stage of light irradiation. When polymerization of the sample (photopolymerizable composition) occurs accompanying light irradiation, a heat of reaction accompanying the polymerization is generated, and the heat of reaction can be measured by photo DSC. Thus, the degree of progress of polymerization by light irradiation can be measured by photo DSC. In this Example, the total heating value in one minute after light irradiation is measured, and so long as the same polymerizable compound is used, it is considered that the larger the total heating value, the more efficiently the polymerization proceeds.

(Photo Rheometer)

The photo rheometer measurement was conducted in Examples as follows. Using a photo rheometer MCR102 manufactured by Anton Paar, transition of the complex viscosity of the photocurable composition was measured, and from the viscosity increasing rate, the curing rate was measured.

Measurement Conditions:
Measurement jig: parallel plate (diameter: 10 mm)
Thickness: 100 μm
Amplitude: constant at 5.0%
Frequency: constant at 10 Hz
Temperature: constant at 30° C.
Measurement atmosphere: nitrogen atmosphere
UV irradiator: LLBK-UV manufactured by AITEC SYSTEM Co., Ltd. (irradiation wavelength: 405 nm)
Irradiation intensity: 200 mW/cm$^2$
Irradiation start time: 30 seconds later
Curing time: the time period (second) from the start of light irradiation until the complex viscosity reached 40,000 Pa·s was taken as the curing time The photopolymerizability evaluation test for a photocationic polymerizable composition containing the 9,10-bis(alkoxycarbonylalkyleneoxy)anthracene compound having ester groups of the present invention as a photocationic polymerization sensitizer will be described below.

Photo-Curing Rate Evaluation Example 1

100 Parts by weight of 3',4'-epoxycyclohexylmethyl-3,4-epoxycyclohexanecarboxylate (manufactured by Daicel Corporation, tradename: CELLOXIDE 2021P, registered trademark) as a photocationic polymerizable compound, 2 parts by weight of 4-isobutylphenyl-4'-methylphenyliodonium hexafluorophosphate (manufactured by BASF, tradename: Irgacure 250, registered trademark) as a photopolymerization initiator, and 1 part by weight of the 9,10-bis(methoxycarbonylmethyleneoxy)anthracene obtained in Preparation Example 1 as a photocationic polymerization sensitizer, were mixed at room temperature to prepare a photocationic polymerizable composition. The photopolymerizable composition was subjected to photo DSC measurement, whereupon the total heating value in 5 minutes from the start of light irradiation was 256 mJ/mg.

Photo-Curing Rate Evaluation Example 2

The photo DSC measurement was conducted in the same manner as in Photo-curing Rate Evaluation Example 1 except that the 9,10-bis(methoxycarbonylmethyleneoxy)anthracene in Photo-curing Rate Evaluation Example 1 was changed to 9,10-bis(ethoxycarbonylmethyleneoxy)anthracene obtained in the same manner as in Preparation Example 2, whereupon the total heating value in 5 minutes from the start of light irradiation was 273 mJ/mg.

Photo-Curing Rate Evaluation Example 3

The photo DSC measurement was conducted in the same manner as in Photo-curing Rate Evaluation Example 1 except that the 9,10-bis(methoxycarbonylmethyleneoxy)anthracene in Photo-curing Rate Evaluation Example 1 was changed to 9,10-bis(isopropoxycarbonylmethyleneoxy)anthracene obtained in the same manner as in Preparation Example 3, whereupon the total heating value in 5 minutes from the start of light irradiation was 262 mJ/mg.

Photo-Curing Rate Evaluation Example 4

The photo DSC measurement was conducted in the same manner as in Photo-curing Rate Evaluation Example 1 except that the 9,10-bis(methoxycarbonylmethyleneoxy)anthracene in Photo-curing Rate Evaluation Example 1 was changed to 9,10-bis(tert-butoxycarbonylmethyleneoxy)anthracene obtained in the same manner as in Preparation Example 4, whereupon the total heating value in 5 minutes from the start of light irradiation was 284 mJ/mg.

Photo-Curing Rate Evaluation Example 5

The photo DSC measurement was conducted in the same manner as in Photo-curing Rate Evaluation Example 1 except that the 9,10-bis(methoxycarbonylmethyleneoxy)anthracene in Photo-curing Rate Evaluation Example 1 was changed to 9,10-bis(n-butoxycarbonylmethyleneoxy)anthracene obtained in the same manner as in Preparation Example 5, whereupon the total heating value in 5 minutes from the start of light irradiation was 248 mJ/mg.

Photo-Curing Rate Evaluation Example 6

The photo DSC measurement was conducted in the same manner as in Photo-curing Rate Evaluation Example 1 except that the 9,10-bis(methoxycarbonylmethyleneoxy)anthracene in Photo-curing Rate Evaluation Example 1 was changed to 9,10-bis(methoxycarbonylmethylmethyleneoxy)anthracene obtained in the same manner as in Preparation Example 6, whereupon the total heating value in 5 minutes from the start of light irradiation was 226 mJ/mg.

Photo-Curing Rate Evaluation Example 7

The photo DSC measurement was conducted in the same manner as in Photo-curing Rate Evaluation Example 1 except that the 9,10-bis(methoxycarbonylmethyleneoxy)anthracene in Photo-curing Rate Evaluation Example 1 was changed to 9,10-bis(ethoxycarbonylpropyleneoxy)anthracene obtained in the same manner as in Preparation Example 7, whereupon the total heating value in 5 minutes from the start of light irradiation was 308 mJ/mg.

Photo-Curing Rate Evaluation Example 8

The photo DSC measurement was conducted in the same manner as in Photo-curing Rate Evaluation Example 1 except that the 9,10-bis(methoxycarbonylmethyleneoxy)anthracene in Photo-curing Rate Evaluation Example 1 was changed to 9,10-bis(ethoxycarbonylbutyleneoxy)anthracene obtained in the same manner as in Preparation Example 8, whereupon the total heating value in 5 minutes from the start of light irradiation was 285 mJ/mg.

Photo-Curing Rate Evaluation Example 9

The photo DSC measurement was conducted in the same manner as in Photo-curing Rate Evaluation Example 1 except that the 9,10-bis(methoxycarbonylmethyleneoxy)anthracene in Photo-curing Rate Evaluation Example 1 was changed to 2-ethyl-9,10-bis(isopropoxycarbonylmethyleneoxy)anthracene obtained in the same manner as in Preparation Example 9, whereupon the total heating value in 5 minutes from the start of light irradiation was 260 mJ/mg.

Photo-Curing Rate Evaluation Example 17

The photo DSC measurement was conducted in the same manner as in Photo-curing Rate Evaluation Example 1 except that the 9,10-bis(methoxycarbonylmethyleneoxy)anthracene in Photo-curing Rate Evaluation Example 1 was changed to 9,10-bis(propoxycarbonylmethyleneoxy)anthracene obtained in the same manner as in Preparation Example 11, whereupon the total heating value in 5 minutes from the start of light irradiation was 259 mJ/mg.

Photo-Curing Rate Evaluation Example 18

The photo DSC measurement was conducted in the same manner as in Photo-curing Rate Evaluation Example 1 except that the 9,10-bis(methoxycarbonylmethyleneoxy)anthracene in Photo-curing Rate Evaluation Example 1 was changed to 9,10-bis(2-hydroxyethoxycarbonylmethyleneoxy)anthracene obtained in the same manner as in Preparation Example 13, whereupon the total heating value in 5 minutes from the start of light irradiation was 237 mJ/mg.

Photo-Curing Rate Evaluation Example 21

The photo DSC measurement was conducted in the same manner as in Photo-curing Rate Evaluation Example 1 except that the 9,10-bis(methoxycarbonylmethyleneoxy)anthracene in Photo-curing Rate Evaluation Example 1 was changed to 9,10-bis(n-pentyloxycarbonylmethyleneoxy)anthracene obtained in the same manner as in Preparation Example 18, whereupon the total heating value in 5 minutes from the start of light irradiation was 268 mJ/mg.

Photo-Curing Rate Evaluation Example 22

The photo DSC measurement was conducted in the same manner as in Photo-curing Rate Evaluation Example 1 except that the 9,10-bis(methoxycarbonylmethyleneoxy)anthracene in Photo-curing Rate Evaluation Example 1 was changed to 9,10-bis(cyclohexyloxycarbonylmethyleneoxy)anthracene obtained in the same manner as in Preparation Example 19, whereupon the total heating value in 5 minutes from the start of light irradiation was 256 mJ/mg.

Photo-Curing Rate Evaluation Example 23

The photo DSC measurement was conducted in the same manner as in Photo-curing Rate Evaluation Example 1 except that the photopolymerization initiator in Photo-curing Rate Evaluation Example 1 was changed to diphenyl-4-phenylthiophenylsulfonium hexafluorophosphate (manufactured by Daicel Corporation, tradename: CPI-100P), and the photocationic polymerization sensitizer was changed to 9,10-bis(ethoxycarbonylmethyleneoxy)anthracene obtained in the same manner as in Preparation Example 2, whereupon the total heating value in 5 minutes from the start of light irradiation was 200 mJ/mg.

Photo-Curing Rate Evaluation Example 24

The photo DSC measurement was conducted in the same manner as in Photo-curing Rate Evaluation Example 2 except that the photocationic polymerizable compound in Photo-curing Rate Evaluation Example 1 was changed to (3,3',4,4'-diepoxy)bicyclohexyl (manufactured by Daicel Corporation, tradename: CELLOXIDE 8010), and the photocationic polymerization sensitizer was changed to 9,10-bis(ethoxycarbonylmethyleneoxy)anthracene obtained in the same manner as in Preparation Example 2, whereupon the total heating value in 5 minutes from the start of light irradiation was 416 mJ/mg.

Photo-Curing Rate Evaluation Example 33

The photo DSC measurement was conducted in the same manner as in Photo-curing Rate Evaluation Example 2 except that the photocationic polymerizable compound in Photo-curing Rate Evaluation Example 1 was changed to (3,3',4,4'-diepoxy)bicyclohexyl (manufactured by Daicel Corporation, tradename: CELLOXIDE 8010), and the photocationic polymerization sensitizer was changed to 9,10-bis(cyclohexyloxycarbonylmethyleneoxy)anthracene obtained in the same manner as in Preparation Example 19, whereupon the total heating value in 5 minutes from the start of light irradiation was 411 mJ/mg.

Photo-Curing Rate Evaluation Comparative Example 1

100 Parts by weight of 3',4'-epoxycyclohexylmethyl-3,4-epoxycyclohexane carboxylate (manufactured by Daicel Corporation, tradename: CELLOXIDE 2021P, registered trademark) as a photocationic polymerizable compound and 2 parts by weight of (4-methylphenyl)[4-(2-methylpropyl)phenyl]iodonium hexafluorophosphate (manufactured by BASF, tradename: Irgacure 250, registered trademark) as a photopolymerization initiator were mixed at room temperature to prepare a photocationic polymerizable composition. The photopolymerizable composition was subjected to photo DSC measurement, whereupon the total heating value in one minute from the start of light irradiation was 3 mJ/mg.

Photo-Curing Rate Evaluation Comparative Example 2

The photo DSC measurement was conducted in the same manner as in Photo-curing Rate Evaluation Example 1 except that a known photopolymerization sensitizer 9,10- dibutoxyanthracene was used instead of the 9,10-bis (methoxycarbonylmethyleneoxy)anthracene in Photo-curing Rate Evaluation Example 1, whereupon the total heating value in 5 minutes from the start of light irradiation was 230 mJ/mg.

Photo-Curing Rate Evaluation Comparative Example 3

The photo DSC measurement was conducted in the same manner as in Photo-curing Rate Evaluation Example 1 except that a known photopolymerization sensitizer 9,10-bis(octanoyloxy)anthracene was used instead of the 9,10-bis(methoxycarbonylmethyleneoxy)anthracene in Photo-curing Rate Evaluation Example 1, whereupon the total heating value in 5 minutes from the start of light irradiation was 234 mJ/mg.

Photo-Curing Rate Evaluation Comparative Example 7

100 Parts by weight of 3',4'-epoxycyclohexylmethyl-3,4-epoxycyclohexane carboxylate (manufactured by Daicel Corporation, tradename: CELLOXIDE 2021P, registered trademark) as a photocationic polymerizable compound and 2 parts by weight of diphenyl-4-phenylthiophenylsulfonium hexafluorophosphate (manufactured by Daicel Corporation, tradename: CPI-100P) as a photopolymerization initiator were mixed at room temperature to prepare a photocationic polymerizable composition. The photopolymerizable composition was subjected to photo DSC measurement, whereupon the total heating value in 5 minutes from the start of light irradiation was 0 mJ/mg.

Photo-Curing Rate Evaluation Comparative Example 8

100 Parts by weight of (3,3',4,4'-diepoxy)bicyclohexyl (manufactured by Daicel Corporation, tradename: CELLOXIDE 8010) as a photocationic polymerizable compound and 2 parts by weight of (4-methylphenyl)[4-(2-methylpropyl)phenyl]iodonium hexafluorophosphate (manufactured by BASF, tradename: Irgacure 250, registered trademark) as a photopolymerization initiator were mixed at room temperature to prepare a photocationic polymerizable composition. The photopolymerizable composition was subjected to photo DSC measurement, whereupon the total heating value in 5 minutes from the start of light irradiation was 2 mJ/mg.

The results of Photo-curing Rate Evaluation Examples 1 to 9, 17, 18, 21 to 24 and 33 and Photo-curing Rate Evaluation Comparative Examples 1 to 3, 7 and 8 are shown in Table 1.

TABLE 1

| | Polymerizable compound (parts by weight) | Photopolymerization initiator (parts by weight) | Photopolymerization sensitizer (parts by weight) | Total heating value (mJ/mg) |
|---|---|---|---|---|
| Photo-curing Rate Evaluation Example 1 | CELLOXIDE 2021P (100 parts) | Irgacure 250 (2 parts) | 9,10-bis(methoxycarbonyl-methyleneoxy)anthracene (1 part) | 256 |
| Photo-curin Rate Evaluation Example 2 | | | 9,10-bis(ethoxycarbonyl-methyleneoxy)anthracene(1 part) | 273 |
| Photo-curing Rate Evaluation Example 3 | | | 9,10-bis(isopropoxycarbonyl-methyleneoxy)anthracene (1 part) | 262 |
| Photo-curing Rate Evaluation Example 4 | | | 9,10-bis(tert-butoxycarbonyl-methyleneoxy)anthracene (1 part) | 284 |
| Photo-curing Rate Evaluation Example 5 | | | 9,10-bis(n-butoxycarbonylmethyl-eneoxy)anthracene (1 part) | 248 |
| Photo-curing Rate Evaluation Example 6 | | | 9,10-bis(methoxycarbonylmethyl-methyleneoxy)anthracene (1 part) | 226 |
| Photo-curing Rate Evaluation Example 7 | | | 9,10-bis(ethoxycarbonylpropyl-eneoxy)anthracene (1 part) | 308 |
| Photo-curing Rate Evaluation Example 8 | | | 9,10-bis(ethoxycarbonylbutyl-eneoxy)anthracene (1 part) | 285 |
| Photo-curing Rate Evaluation Example 9 | | | 2-ethyl-9,10-bis(isopropoxycarbonyl-methyleneoxy)anthracene (1 part) | 260 |
| Photo-curing Rate Evaluation Example 17 | | | 9,10-bis(propoxycarbonyl-methoxy)anthracene (1 part) | 259 |
| Photo-curing Rate Evaluation Example 18 | | | 9,10-bis(2-hydroxyethoxycarbonyl methoxy)anthracene (1 part) | 237 |
| Photo-curing Rate Evaluation Example 21 | | | 9,10-bis(n-pentyloxycarbony-methyleneoxy)anthracene (1 part) | 268 |
| Photo-curing Rate Evaluation Example 22 | | | 9,10-bis(cyclohexyloxycarbonyl-methyleneoxy)anthracene (1 part) | 256 |
| Photo-curing Rate Evaluation Example 23 | | CPI-100P (2 parts) | 9,10-bis(ethoxycarbonylmethyl-eneoxy)anthracene (1 part) | 200 |

TABLE 1-continued

| | Polymerizable compound (parts by weight) | Photopolymerization initiator (parts by weight) | Photopolymerization sensitizer (parts by weight) | Total heating value (mJ/mg) |
|---|---|---|---|---|
| Photo-curing Rate Evaluation Example 24 | CELLOXIDE 8010 (100 parts) | Irgacure 250 (2 parts) | 9,10-bis(ethoxycarbonylmethyleneoxy)anthracene (1 part) | 416 |
| Photo-curing Rate Evaluation Example 33 | | | 9,10-bis(cyclohexyloxycarbonylmethyleneoxy)anthracene (1 part) | 411 |
| Photo-curing Rate Evaluation Comparative Example 1 | CELLOXIDE 2021P (100 parts) | Irgacure 250 (2 parts) | Nil | 3 |
| Photo-curing Rate Evaluation Comparative Example 2 | | | 9,10-dibutoxyanthracene (1 part) | 230 |
| Photo-curing Rate Evaluation Comparative Example 3 | | | 9,10-bis(octanoyloxy)anthracene (1 part) | 234 |
| Photo-curing Rate Evaluation Comparative Example 7 | | CPI-100P (2 parts) | Nil | 0 |
| Photo-curing Rate Evaluation Comparative Example 8 | CELLOXIDE 8010 (100 parts) | Irgacure 250 (2 parts) | Nil | 2 |

CELLOXIDE 2021P: 3',4'-epoxycyclohexylmethyl-3,4-epoxycyclohexanecarboxylate
CELLOXIDE 8010: (3,3',4,4'-diepoxy)bicyclohexyl
Irgacure 250: 4-isobutylphenyl-4'-methylphenyliodonium hexafluorophosphate
CPI-100P: diphenyl-4-phenylthiophenylsulfonium hexafluorophosphate The photopolymerizability evaluation test for a radical polymerizable composition containing the 9,10-bis(alkoxycarbonylalkyleneoxy)anthracene compound having ester groups of the present invention as a photoradical polymerization sensitizer will be described below.

Photo-Curing Rate Evaluation Example 10

100 Parts by weight of trimethylolpropane triacrylate as a photoradical polymerizable compound, 2 parts by weight of 1-hydroxycyclohexyl phenyl ketone as a photopolymerization initiator, and 1 part by weight of the 9,10-bis(methoxycarbonylmethyleneoxy)anthracene obtained in Preparation Example 1 as a photoradical polymerization sensitizer, were mixed at room temperature to prepare a photoradical polymerizable composition. The photopolymerizable composition was subjected to photo DSC measurement, whereupon the total heating value in 5 minutes from the start of light irradiation was 419 mJ/mg.

Photo-Curing Rate Evaluation Example 11

The photo DSC measurement was conducted in the same manner as in Photo-curing Rate Evaluation Example 10 except that the 9,10-bis(methoxycarbonylmethyleneoxy)anthracene in Photo-curing Rate Evaluation Example 10 was changed to 9,10-bis(ethoxycarbonylmethyleneoxy)anthracene obtained in the same manner as in Preparation Example 2, whereupon the total heating value in 5 minutes from the start of light irradiation was 465 mJ/mg.

Photo-Curing Rate Evaluation Example 12

The photo DSC measurement was conducted in the same manner as in Photo-curing Rate Evaluation Example 10 except that the 9,10-bis(methoxycarbonylmethyleneoxy)anthracene in Photo-curing Rate Evaluation Example 10 was changed to 9,10-bis(isopropoxycarbonylmethyleneoxy)anthracene obtained in the same manner as in Preparation Example 3, whereupon the total heating value in 5 minutes from the start of light irradiation was 409 mJ/mg.

Photo-Curing Rate Evaluation Example 13

The photo DSC measurement was conducted in the same manner as in Photo-curing Rate Evaluation Example 10 except that the 9,10-bis(methoxycarbonylmethyleneoxy)anthracene in Photo-curing Rate Evaluation Example 10 was changed to 9,10-bis(tert-butoxycarbonylmethyleneoxy)anthracene obtained in the same manner as in Preparation Example 4, whereupon the total heating value in 5 minutes from the start of light irradiation was 443 mJ/mg.

Photo-Curing Rate Evaluation Example 14

The photo DSC measurement was conducted in the same manner as in Photo-curing Rate Evaluation Example 10 except that the 9,10-bis(methoxycarbonylmethyleneoxy)anthracene in Photo-curing Rate Evaluation Example 10 was changed to 9,10-bis(n-butoxycarbonylmethyleneoxy)anthracene obtained in the same manner as in Preparation Example 5, whereupon the total heating value in 5 minutes from the start of light irradiation was 336 mJ/mg.

Photo-Curing Rate Evaluation Example 15

The photo DSC measurement was conducted in the same manner as in Photo-curing Rate Evaluation Example 10 except that the 9,10-bis(methoxycarbonylmethyleneoxy)anthracene in Photo-curing Rate Evaluation Example 10 was changed to 9,10-bis(methoxycarbonylmethylmethyleneoxy)anthracene obtained in the same manner as in Preparation Example 6, whereupon the total heating value in 5 minutes from the start of light irradiation was 552 mJ/mg.

Photo-Curing Rate Evaluation Example 16

The photo DSC measurement was conducted in the same manner as in Photo-curing Rate Evaluation Example 10 except that the 9,10-bis(methoxycarbonylmethyleneoxy)anthracene in Photo-curing Rate Evaluation Example 10 was changed to 2-ethyl-9,10-bis(isopropoxycarbonylmethyleneoxy)anthracene obtained in the same manner as in Preparation Example 9, whereupon the total heating value in 5 minutes from the start of light irradiation was 441 mJ/mg.

Photo-Curing Rate Evaluation Example 19

The photo DSC measurement was conducted in the same manner as in Photo-curing Rate Evaluation Example 10 except that the 9,10-bis(methoxycarbonylmethyleneoxy)anthracene in Photo-curing Rate Evaluation Example 10 was changed to 9,10-bis(propoxycarbonylmethyleneoxy)anthracene obtained in the same manner as in Preparation Example 11, whereupon the total heating value in 5 minutes from the start of light irradiation was 379 mJ/mg.

Photo-Curing Rate Evaluation Example 20

The photo DSC measurement was conducted in the same manner as in Photo-curing Rate Evaluation Example 10 except that the 9,10-bis(methoxycarbonylmethyleneoxy)anthracene in Photo-curing Rate Evaluation Example 10 was changed to 9,10-bis(2-hydroxyethoxycarbonylmethyleneoxy)anthracene obtained in the same manner as in Preparation Example 13, whereupon the total heating value in 5 minutes from the start of light irradiation was 420 mJ/mg.

Photo-Curing Rate Evaluation Example 25

The photo DSC measurement was conducted in the same manner as in Photo-curing Rate Evaluation Example 10 except that the 9,10-bis(methoxycarbonylmethyleneoxy)anthracene in Photo-curing Rate Evaluation Example 10 was changed to 9,10-bis(n-pentyloxycarbonylmethyleneoxy)anthracene obtained in the same manner as in Preparation Example 18, whereupon the total heating value in 5 minutes from the start of light irradiation was 376 mJ/mg.

Photo-Curing Rate Evaluation Example 26

The photo DSC measurement was conducted in the same manner as in Photo-curing Rate Evaluation Example 10 except that the 9,10-bis(methoxycarbonylmethyleneoxy)anthracene in Photo-curing Rate Evaluation Example 10 was changed to 9,10-bis(cyclohexyloxycarbonylmethyleneoxy)anthracene obtained in the same manner as in Preparation Example 19, whereupon the total heating value in 5 minutes from the start of light irradiation was 354 mJ/mg.

Photo-Curing Rate Evaluation Example 27

The photo DSC measurement was conducted in the same manner as in Photo-curing Rate Evaluation Example 10 except that the photopolymerization initiator in Photo-curing Rate Evaluation Example 10 was changed to 2,2-dimethoxy-1,2-diphenylethan-1-one (tradename "Irgacure 651" manufactured by BASF), and the photoradical polymerization sensitizer was changed to 0.2 part by weight of the 9,10-bis(ethoxycarbonylmethyleneoxy)anthracene obtained in the same manner as in Preparation Example 2, whereupon the total heating value in 5 minutes from the start of light irradiation was 487 mJ/mg.

Photo-curing Rate Evaluation Example 28

The photo DSC measurement was conducted in the same manner as in Photo-curing Rate Evaluation Example 10 except that the photopolymerization initiator in Photo-curing Rate Evaluation Example 10 was changed to 2-methyl-1-[4-(methylthio)phenyl]-2-morpholinopropan-1-one (tradename: Irgacure 907 manufactured by BASF), and the photoradical polymerization sensitizer was changed to 0.2 part by weight of the 9,10-bis(ethoxycarbonylmethyleneoxy)anthracene obtained in the same manner as in Preparation Example 2, whereupon the total heating value in 5 minutes from the start of light irradiation was 496 mJ/mg.

Photo-Curing Rate Evaluation Example 29

The photo DSC measurement was conducted in the same manner as in Photo-curing Rate Evaluation Example 10 except that the photopolymerization initiator in Photo-curing Rate Evaluation Example 10 was changed to 2,4,6-trimethylbenzoyl-diphenylphosphine oxide (tradename: Irgacure TPO manufactured by BASF), and the photoradical polymerization sensitizer was changed to 0.2 part by weight of the 9,10-bis(ethoxycarbonylmethyleneoxy)anthracene obtained in the same manner as in Preparation Example 2, whereupon the total heating value in 5 minutes from the start of light irradiation was 635 mJ/mg.

Photo-Curing Rate Evaluation Example 30

To 50 parts by weight of FA-310M (phenoxyethyl methacrylate, manufactured by Hitachi Chemical Co., Ltd.) and 50 parts by weight of FA-321M (EO-modified bisphenol A dimethacrylate, manufactured by Hitachi Chemical Co., Ltd.) as radical polymerizable compounds, 0.5 part by weight of [8-[[(acetyloxy)imino][2-(2,2,3,3-tetrafluoropropoxy)phenyl]methyl]-11-(2-ethylhexyl)-11H-benzo[a]carbazol-5-yl]-, (2,4,6-trimethylphenyl) (tradename: Irgacure OXE03 manufactured by BASF) as a photoradical polymerization initiator was added. Further, 0.2 part by weight of the 9,10-bis(ethoxycarbonylmethyleneoxy)anthracene obtained in Preparation Example 2 was added to prepare a photoradical polymerizable composition, which was dropped on a quartz glass of the rheometer and sandwiched between parallel plates having a thickness of 100 μm and a diameter of 10 mm, and the photo-curing composition unnecessary for viscosity measurement was wiped off. 30 seconds after the start of the viscosity measurement of the photo-curing composition, UV-LED light having a wavelength of 405 nm was applied. The time until the complex viscosity reached 40,000 Pas was 386 seconds.

Photo-Curing Rate Evaluation Example 31

To 50 parts by weight of FA-310M (phenoxyethyl methacrylate, manufactured by Hitachi Chemical Co., Ltd.) and 50 parts by weight of FA-321M (EO-modified bisphenol A dimethacrylate, manufactured by Hitachi Chemical Co., Ltd.) as radical polymerizable compounds, 2 parts by weight of 2-(o-chlorophenyl)-4,5-diphenylimidazole dimer as a photoradical polymerization initiator was added, and 0.17 part of Leuco Crystal Violet (manufactured by Wako Pure Chemical Industries, Ltd.) as a coloring agent was added.

Further, 0.6 part by weight of the 9,10-bis(ethoxycarbonylmethyleneoxy)anthracene obtained in Preparation Example 2 was added to prepare a photoradical polymerizable composition, which was dropped on a quartz glass of the rheometer and sandwiched between parallel plates having a thickness of 100 μm and a diameter of 10 mm, and the photo-curing composition unnecessary for viscosity measurement was wiped off. 30 seconds after the start of the viscosity measurement of the photo-curing composition, UV-LED light having a wavelength of 405 nm was applied. The time until the complex viscosity reached 40,000 Pa·s was 592 seconds.

Photo-Curing Rate Evaluation Example 32

To 100 parts by weight of Viscoat #230 (1,6-hexanediol diacrylate, manufactured by OSAKA ORGANIC CHEMICAL INDUSTRY LTD.) as a photoradical polymerizable compound, 5 parts by weight of 2-(4-methoxyphenyl)-4,6-bis(trichloromethyl)-1,3,5-triazine (manufactured by Tokyo Chemical Industry Co., Ltd.) as a photoradical polymerization initiator was added. Further, 1 part by weight of the 9,10-bis(ethoxycarbonylmethyleneoxy)anthracene obtained in Preparation Example 2 was added to prepare a photoradical polymerizable composition, which was dropped on a quartz glass of the rheometer and sandwiched between parallel plates having a thickness of 100 μm and a diameter of 10 mm, and the photo-curing composition unnecessary for viscosity measurement was wiped off. 30 seconds after the start of the viscosity measurement of the photo-curing composition, UV-LED light having a wavelength of 405 nm was applied. The time until the complex viscosity reached 40,000 Pas was 85 seconds.

Photo-Curing Rate Evaluation Comparative Example 4

100 Parts by weight of trimethylolpropane triacrylate as a photoradical polymerizable compound and 2 parts by weight of 1-hydroxycyclohexyl phenyl ketone as a photopolymerization initiator were mixed at room temperature to prepare a photoradical polymerizable composition. The photopolymerizable composition was subjected to photo DSC measurement, whereupon the total heating value in 5 minutes from the start of light irradiation was 166 mJ/mg.

Photo-Curing Rate Evaluation Comparative Example 5

The photo DSC measurement was conducted in the same manner as in Photo-curing Rate Evaluation Example 10 except that a known photopolymerization sensitizer 9,10-dibutoxyanthracene was used instead of the 9,10-bis(methoxycarbonyl(methyleneoxy)anthracene in Photo-curing Rate Evaluation Example 10, whereupon the total heating value in 5 minutes from the start of light irradiation was 212 mJ/mg.

Photo-Curing Rate Evaluation Comparative Example 6

The photo DSC measurement was conducted in the same manner as in Photo-curing Rate Evaluation Example 10 except that a known photopolymerization sensitizer 9,10-bis(octanoyloxy)anthracene was used instead of the 9,10-bis(methoxycarbonylmethyleneoxy)anthracene in Photo-curing Rate Evaluation Example 10, whereupon the total heating value in 5 minutes from the start of light irradiation was 298 mJ/mg.

Photo-Curing Rate Evaluation Comparative Example 9

100 Parts by weight of trimethylolpropane triacrylate as a radical polymerizable compound and 2 parts by weight of 2,2-dimethoxy-1,2-diphenylethan-1-one (tradename "Irgacure 651" manufactured by BASF) as a photopolymerization initiator were mixed at room temperature to prepare a photoradical polymerizable composition. The photopolymerizable composition was subjected to photo DSC measurement, whereupon the total heating value in 5 minutes from the start of light irradiation was 346 mJ/mg.

Photo-Curing Rate Evaluation Comparative Example 10

100 Parts by weight of trimethylolpropane triacrylate as a photoradical polymerizable compound and 2 parts by weight of 2-methyl-1-[4-(methylthio)phenyl]-2-morpholinopropan-1-one (tradename: Irgacure 907 manufactured by BASF) as a photopolymerization initiator were mixed at room temperature to prepare a photoradical polymerizable composition. The photopolymerizable composition was subjected to photo DSC measurement, whereupon the total heating value in 5 minutes from the start of light irradiation was 392 mJ/mg.

Photo-Curing Rate Evaluation Comparative Example 11

100 Parts by weight of trimethylolpropane triacrylate as a photoradical polymerizable compound and 2 parts by weight of 2,4,6-trimethylbenzoyl-diphenylphosphine oxide (tradename: Irgacure TPO manufactured by BASF) as a photopolymerization initiator were mixed at room temperature to prepare a photoradical polymerizable composition. The photopolymerizable composition was subjected to photo DSC measurement, whereupon the total heating value in one minute from the start of light irradiation was 566 mJ/mg.

Photo-Curing Rate Evaluation Comparative Example 12

The viscosity measurement was conducted in the same manner as in Photo-curing Rate Evaluation Example 30 except that 9,10-bis(ethoxycarbonylmethyleneoxy)anthracene was not added. The time until the complex viscosity reached 40,000 Pa·s was 1,822 seconds.

Photo-Curing Rate Evaluation Comparative Example 13

The viscosity measurement was conducted in the same manner as in Photo-curing Rate Evaluation Example 31 except that 9,10-bis(ethoxycarbonylmethyleneoxy)anthracene was not added. The time until the complex viscosity reached 40,000 Pa·s was 1,256 seconds.

Photo-Curing Rate Evaluation Comparative Example 14

The viscosity measurement was conducted in the same manner as in Photo-curing Rate Evaluation Example 32 except that 9,10-bis(ethoxycarbonylmethyleneoxy)anthracene was not added. The time until the complex viscosity reached 40,000 Pa·s was 335 seconds.

The results of Photo-curing Rate Evaluation Examples 10 to 16, 19, 20 and 25 to 29 and Photo-curing Rate Evaluation Comparative Examples 4 to 6 and 9 to 11 are shown in Table 2.

TABLE 2

| | Polymerizable compound (parts by weight) | Photopolymerization initiator (parts by weight) | Photopolymerization sensitizer (parts by weight) | Total heating value (mJ/mg) |
|---|---|---|---|---|
| Photo-curing Rate Evaluation Example 10 | Trimethylolpropane triacrylate (100 parts) | Irgacure 184 (2 parts) | 9,10-bis(methoxycarbonylmethyleneoxy)anthracene (1 part) | 419 |
| Photo-curing Rate Evaluation Example 11 | | | 9,10-bis(ethoxycarbonylmethyleneoxy)anthracene (1 part) | 465 |
| Photo-curing Rate Evaluation Example 12 | | | 9,10-bis(isopropoxycarbonylmethyleneoxy)anthracene (1 part) | 409 |
| Photo-curing Rate Evaluation Example 13 | | | 9,10-bis(tert-butoxycarbonylmethyleneoxy)anthracene (1 part) | 443 |
| Photo-curing Rate Evaluation Example 14 | | | 9,10-bis(n-butoxycarbonylmethyleneoxy)anthracene (1 part) | 336 |
| Photo-curing Rate Evaluation Example 15 | | | 9,10-bis(methoxycarbonylmethyl-methyleneoxy)anthracene (1 part) | 552 |
| Photo-curing Rate Evaluation Example 16 | | | 2-ethyl-9,10-bis(isopropoxycarbonylmethyleneoxy)anthracene (1 part) | 441 |
| Photo-curing Rate Evaluation Example 19 | | | 9,10-bis(propoxycarbonylmethoxy)anthracene (1 part) | 379 |
| Photo-curing Rate Evaluation Example 20 | | | 9,10-bis(2-hydroxyethoxycarbonylmethoxy)anthracene-(1 part) | 420 |
| Photo-curing Rate Evaluation Example 25 | | | 9,10-bis(n-pentyloxycarbonylmethyleneoxy)anthracene (1 part) | 376 |
| Photo-curing Rate Evaluation Example 26 | | | 9,10-bis(cyclohexyloxycarbonylmethyleneoxy)anthracene (1 part) | 354 |
| Photo-curin Rate Evaluation Example 27 | | Irgacure 651 (2 parts) | 9,10-bis(n-ethoxycarbonylmethyleneoxy)anthracene (1 part) | 487 |
| Photo-curing Rate Evaluation Example 28 | | Irgacure 907 (2 parts) | 9,10-bis(ethoxycarbonylmethyleneoxy)anthracene (1 part) | 496 |
| Photo-curing Rate Evaluation Example 29 | | Irgacure TPO (2 parts) | 9,10-bis(ethoxycarbonylmethyleneoxy)anthracene (1 part) | 635 |
| Photo-curing Rate Evaluation Comparative Example 4 | | Irgacure 184 (2 parts) | Nil | 166 |
| Photo-curing Rate Evaluation Comparative Example 5 | | | 9,10-dibutoxyanthracene (1 part) | 212 |
| Photo-curing Rate Evaluation Comparative Example 6 | | | 9,10-bis(octanoyloxy)anthracene (1 part) | 298 |
| Photo-curing Rate Evaluation Comparative Example 9 | | Irgacure 651 (2 parts) | Nil | 346 |
| Photo-curing Rate Evaluation Comparative Example 11 | | Irgacure 907 (2 parts) | Nil | 566 |

Irgacure 250: 4-isobutylphenyl-4'-methylphenyliodonium hexafluorophosphate
Irgacure 651: 2,2-dimethoxy-1,2-diphenylethan-1-one
Irgacure 907: 2-methyl-1-[4-(methylthio)phenyl]-2-morpholinopropan-1-one
Irgacure TPO: 2,4,6-trimethylbenzoyl-diphenylphosphine oxide The results of Photo-curing Rate Evaluation Examples 30 to 32 and Photo-curing Rate Evaluation Comparative Examples 12 to 14 are shown in Table 3.

TABLE 3

| | Polymerizable compound (parts by weight) | Photopolymerization initiator (parts by weight) | Photopolymerization sensitizer (parts by weight) | Time until complex viscosity reached 40,000 Pa·s (sec) |
|---|---|---|---|---|
| Photo-curing Rate Evaluation Example 30 | FA-310M (50 parts) FA-321M (50 parts) | Irgacure OXE03 (2 parts) | 9,10-bis(ethoxycarbonylmethyleneoxy)anthracene (1 part) | 386 |
| Photo-curing Rate Evaluation Example 31 | | HABI (2 parts) | 9,10-bis(ethoxycarbonylmethyleneoxy)anthracene (1 part) | 592 |
| Photo-curing Rate Evaluation Example 32 | | Triazine (2 parts) | 9,10-bis(ethoxycarbonylmethyleneoxy)anthracene (1 part) | 85 |
| Photo-curing Rate Evaluation Comparative Example 12 | | Irgacure OXE03 (2 parts) | Nil | 1822 |
| Photo-curing Rate Evaluation Comparative Example 13 | | HABI (2 parts) | Nil | 1256 |
| Photo-curing Rate Evaluation Comparative Example 14 | | Triazine (2 parts) | Nil | 335 |

Irgacure OXE03: [8-[[(acetyloxy)imino][2-(2,2,3,3-tetrafluoropropoxy)phenyl]methyl]-11-(2-ethylhexyl)-11H-benzo[a]carbazol-5-yl]-,(2,4,6- trimethylphenyl)
HABI: 2-(o-chlorophenyl)-4,5-diphenylimidazole dimer
Triazine: 2-(4-methoxyphenyl)-4,6-bis(trichloromethyl)-1,3,5-triazine
FA-310M: phenoxyethyl methacrylate
FA-321M: EO-modified bisphenol A dimethacrylate As evident from comparison between the results in Photo-curing Rate Evaluation Examples 1 to 9, 17, 18, 21 to 24 and 33 and in Photo-curing Rate Evaluation Comparative Examples 1, 7 and 8, by adding the 9,10-bis(alkoxycarbonylalkyleneoxy)anthracene compound having ester groups of the present invention as a photopolymerization sensitizer for photocationic polymerization, the total heating value increases, and the polymerization reaction is remarkably accelerated. Further, as evident from comparison between the results in Photo-curing Rate Evaluation Examples 10 to 16, 19, 20 and 25 to 32 and Photo-curing Rate Evaluation Comparative Examples 4 and 9 to 14, by adding the 9,10-bis(alkoxycarbonylalkyleneoxy)anthracene compound having ester groups of the present invention for photoradical polymerization also, the total heating value increases, and the polymerization reaction is remarkably accelerated. That is, it is found that the 9,10-bis(alkoxycarbonylalkyleneoxy) anthracene compound having ester groups of the present invention has a photopolymerization sensitizing effect for both photocationic polymerization and photoradical polymerization.

Further, as evident from comparison between the results in Photo-curing Rate Evaluation Examples 1 to 9, 17, 18, 21 to 24 and 33 and in Photo-curing Rate Evaluation Comparative Examples 2 and 3, the 9,10-bis(alkoxycarbonylalkyleneoxy)anthracene compound having ester groups of the present invention has a photopolymerization sensitizing effect comparable to or higher than known photopolymerization sensitizers 9,10-dibutoxyanthracene and 9,10-bis(octanoyloxy)anthracene, for photocationic polymerization. Further, as evident from comparison between the results in Photo-curing Rate Evaluation Examples 10 to 16, 19, 20 and 25 to 29 and in Photo-curing Rate Evaluation Comparative Examples 5 and 6, the 9,10-bis(alkoxycarbonylalkyleneoxy) anthracene corn pound having ester groups of the present invention has a photopolymerization sensitizing effect comparable to or higher than known photopolymerization sensitizers 9,10-dibutoxyanthracene and 9,10-bis(octanoyloxy) anthracene, for photoradical polymerization also. That is, it is found that the 9,10-bis(alkoxycarbonylalkyleneoxy)anthracene corn pound having ester groups of the present invention has a photopolymerization sensitizing effect comparable to or higher than a known photopolymerization sensitizer 9,10-dibutoxyanthracene for both photocationic polymerization and photoradical polymerization.

Still further, as evident from comparison between the results in Photo-curing Rate Evaluation Examples 30 to 32 and in Photo-curing Rate Evaluation Comparative Examples 12 to 14, by adding the 9,10-bis(alkoxycarbonylalkyleneoxy)anthracene compound having ester groups of the present invention, the time until the complex viscosity reached 40,000 Pa·s is remarkably shortened. Thus, it is found that by adding the 9,10-bis(alkoxycarbonylalkyleneoxy)anthracene compound having ester groups of the present invention, the polymerization rate is remarkably increased. That is, it is found that the 9,10-bis(alkoxycarbonylalkyleneoxy)anthracene compound having ester groups of the present invention has a photopolymerization sensitizing effect very effective also for an oxime ester polymerization initiator, a biimidazole polymerization initiator and a triazine polymerization initiator.

Example for Evaluation of Migration Resistance in Photocationic Polymerization

Migration Resistance Evaluation Example 1

100 parts of 3',4'-epoxycyclohexylmethyl-3,4-epoxycyclohexanecarboxylate (manufactured by Daicel Corporation, tradename: CELLOXIDE 2021P) as an epoxy photocationic polymerizable compound and 1 part of the 9,10-bis(methoxycarbonylmethyleneoxy)anthracene prepared in the same manner as in Preparation Example 1 as a photopolymerization sensitizer, were mixed, and the prepared composition was applied to a polyester film by a bar coater so that the film thickness would be 12 micron. The obtained coating film was covered with a low density polyethylene film (film thickness: 30 micron). Such samples were stored in a dark place for one day or for seven days, and the polyethylene film was peeled from each sample, washed with acetone and dried, the UV spectrum of the film was measured, and the absorbance at 260 nm was measured. The absorbance attributable to the 9,10-bis(methoxycarbonylmethyleneoxy)anthracene, as calculated as 9,10-dibutoxyanthracene, was 0.015 after storage for 1 day and 0.003 after storage for 7 days.

Migration Resistance Evaluation Example 2

The same evaluation as in Migration Resistance Evaluation Example 1 was conducted except that as the photopolymerization sensitizer, 9,10-bis(ethoxycarbonylmethyleneoxy)anthracene prepared in the same manner as in Preparation Example 2 was used instead of the 9,10-bis(methoxycarbonylmethyleneoxy)anthracene. The absorbance at 260 nm of the polyethylene film washed with acetone was measured and as a result, the absorbance attributable to the 9,10-bis(ethoxycarbonylmethyleneoxy)anthracene as calculated as 9,10-dibutoxyanthracene was 0.007 after storage for 1 day and 0.007 after storage for 7 days.

Migration Resistance Evaluation Example 3

The same evaluation as in Migration Resistance Evaluation Example 1 was conducted except that as the photopolymerization sensitizer, 9,10-bis(isopropoxycarbonylmethyleneoxy)anthracene prepared in the same manner as in Preparation Example 3 was used instead of the 9,10-bis(methoxycarbonylmethyleneoxy)anthracene. The absorbance at 260 nm of the polyethylene film washed with acetone was measured and as a result, the absorbance attributable to the 9,10-bis(isopropoxycarbonylmethyleneoxy)anthracene as calculated as 9,10-dibutoxyanthracene was 0.007 after storage for 1 day and 0.007 after storage for 7 days.

Migration Resistance Evaluation Example 4

The same evaluation as in Migration Resistance Evaluation Example 1 was conducted except that as the photopolymerization sensitizer, 9,10-bis(tert-butoxycarbonylmethyleneoxy)anthracene prepared in the same manner as in Preparation Example 4 was used instead of the 9,10-bis(methoxycarbonylmethyleneoxy)anthracene. The absorbance at 260 nm of the polyethylene film washed with acetone was measured and as a result, the absorbance attributable to the 9,10-bis(tert-butoxycarbonylmethyleneoxy)anthracene as calculated as 9,10-dibutoxyanthracene was 0.010 after storage for 1 day and 0.014 after storage for 7 days.

Migration Resistance Evaluation Example 5

The same evaluation as in Migration Resistance Evaluation Example 1 was conducted except that as the photopolymerization sensitizer, 9,10-bis(n-butoxycarbonylmethyleneoxy)anthracene prepared in the same manner as in Preparation Example 5 was used instead of the 9,10-bis(methoxycarbonylmethyleneoxy)anthracene. The absorbance at 260 nm of the polyethylene film washed with acetone was measured and as a result, the absorbance attributable to the 9,10-bis(n-butoxycarbonylmethyleneoxy)anthracene as calculated as 9,10-dibutoxyanthracene was 0.011 after storage for 1 day and 0.007 after storage for 7 days.

Migration Resistance Evaluation Example 6

The same evaluation as in Migration Resistance Evaluation Example 1 was conducted except that as the photopolymerization sensitizer, 9,10-bis(methoxycarbonylmethyleneoxy)anthracene prepared in the same manner as in Preparation Example 6 was used instead of the 9,10-bis(methoxycarbonylmethylmethyleneoxy)anthracene. The absorbance at 260 nm of the polyethylene film washed with acetone was measured and as a result, the absorbance attributable to the 9,10-bis(methoxycarbonylmethylmethyleneoxy)anthracene as calculated as 9,10-dibutoxyanthracene was 0.007 after storage for 1 day and 0.003 after storage for 7 days.

Migration Resistance Evaluation Example 7

The same evaluation as in Migration Resistance Evaluation Example 1 was conducted except that as the photopolymerization sensitizer, 9,10-bis(ethoxycarbonylpropyleneoxy)anthracene prepared in the same manner as in Preparation Example 7 was used instead of the 9,10-bis(methoxycarbonylmethyleneoxy)anthracene. The absorbance at 260 nm of the polyethylene film washed with acetone was measured and as a result, the absorbance attributable to the 9,10-bis(ethoxycarbonylpropyleneoxy)anthracene as calculated as 9,10-dibutoxyanthracene was 0.015 after storage for 1 day and 0.013 after storage for 7 days.

Migration Resistance Evaluation Example 8

The same evaluation as in Migration Resistance Evaluation Example 1 was conducted except that as the photopolymerization sensitizer, 9,10-bis(ethoxycarbonylbutyleneoxy)anthracene prepared in the same manner as in Preparation Example 8 was used instead of the 9,10-bis(methoxycarbonylmethyleneoxy)anthracene. The absorbance at 260 nm of the polyethylene film washed with acetone was measured and as a result, the absorbance attributable to the 9,10-bis(ethoxycarbonylbutyleneoxy)anthracene as calculated as 9,10-dibutoxyanthracene was 0.012 after storage for 1 day and 0.010 after storage for 7 days.

Migration Resistance Evaluation Example 9

The same evaluation as in Migration Resistance Evaluation Example 1 was conducted except that as the photopolymerization sensitizer, 2-ethyl-9,10-bis(isopropoxycarbonylmethyleneoxy)anthracene prepared in the same manner as in Preparation Example 9 was used instead of the 9,10-bis(methoxycarbonylmethyleneoxy)anthracene. The absorbance at 260 nm of the polyethylene film washed with acetone was measured and as a result, the absorbance attributable to the 2-ethyl-9,10-bis(isopropoxycarbonylmethyleneoxy)anthracene as calculated as 9,10-dibutoxyanthracene was 0.015 after storage for 1 day and 0.015 after storage for 7 days.

Migration Resistance Evaluation Example 19

The same evaluation as in Migration Resistance Evaluation Example 1 was conducted except that as the photopolymerization sensitizer, 9,10-bis(n-pentyloxycarbonylmethyleneoxy)anthracene prepared in the same manner as in Preparation Example 18 was used instead of the 9,10-bis(methoxycarbonylmethyleneoxy)anthracene. The absorbance at 260 nm of the polyethylene film washed with acetone was measured and as a result, the absorbance attributable to the 9,10-bis(n-pentyloxycarbonylmethyleneoxy)anthracene as calculated as 9,10-dibutoxyanthracene was 0.014 after storage for 1 day and 0.011 after storage for 7 days.

Migration Resistance Evaluation Example 20

The same evaluation as in Migration Resistance Evaluation Example 1 was conducted except that as the photopolymerization sensitizer, 9,10-bis(cyclohexyloxycarbonylmethyleneoxy)anthracene prepared in the same manner as in Preparation Example 19 was used instead of the 9,10-bis(methoxycarbonylmethyleneoxy)anthracene. The absorbance at 260 nm of the polyethylene film washed with acetone was measured and as a result, the absorbance attributable to the 9,10-bis(cyclohexyloxycarbonylmethyleneoxy)anthracene as calculated as 9,10-dibutoxyanthracene was 0.013 after storage for 1 day and 0.010 after storage for 7 days.

Migration Resistance Evaluation Comparative Example 1

The same evaluation as in Migration Resistance Evaluation Example 1 was conducted except that a known photopolymerization sensitizer 9,10-dibutoxyanthracene was used instead of the 9,10-bis(methoxycarbonylmethyleneoxy)anthracene as the photopolymerization sensitizer. The absorbance at 260 nm of the polyethylene film washed with acetone was measured and as a result, the absorbance of the 9,10-dibutoxyanthracene was 0.737 after storage for 1 day and 0.843 after storage for 7 days.

The results of Migration Resistance Evaluation Examples 1 to 9 and Migration Resistance Evaluation Comparative Example 1 are shown in Table 4.

TABLE 4

|  | Polymerizable compound (parts by weight) | Photopolymerization sensitizer (parts by weight) | Absorbance at 260 nm | |
|---|---|---|---|---|
|  |  |  | After one day | After 7 days |
| Migration Resistance Evaluation Example 1 | CELLOXIDE 2021P | 9,10-bis(methoxycarbonylmethyleneoxy)anthracene (1 part) | 0.015 | 0.003 |
| Migration Resistance Evaluation Example 2 |  | 9,10-bis(ethoxycarbonylmethyleneoxy)anthracene (1 part) | 0.007 | 0.007 |
| Migration Resistance Evaluation Example 3 |  | 9,10-bis(isopropoxycarbonylmethyleneoxy)anthracene (1 part) | 0.007 | 0.007 |
| Migration Resistance Evaluation Example 4 |  | 9,10-bis(tert-butoxycarbonylmethyleneoxy)anthracene (1 part) | 0.010 | 0.014 |
| Migration Resistance Evaluation Example 5 |  | 9,10-bis(n-butoxycarbonylmethyleneoxy)anthracene (1 part) | 0.011 | 0.007 |
| Migration Resistance Evaluation Example 6 |  | 9,10-bis(methoxycarbonylmethylmethyleneoxy)anthracene (1 part) | 0.007 | 0.003 |
| Migration Resistance Evaluation Example 7 |  | 9,10-bis(ethoxycarbonylpropyleneoxy)anthracene (1 part) | 0.015 | 0.013 |
| Migration Resistance Evaluation Example 8 |  | 9,10-bis(ethoxycarbonylbutyleneoxy)anthracene (1 part) | 0.012 | 0.010 |
| Migration Resistance Evaluation Example 9 |  | 2-ethyl-9,10-bis(isopropoxycarbonylmethyleneoxy)anthracene (1 part) | 0.015 | 0.015 |
| Migration Resistance Evaluation Example 19 |  | 9,10-bis(n-pentyloxycarbonylmethyleneoxy)anthracene (1 part) | 0.0147 | 0.011 |
| Migration Resistance Evaluation Example 20 |  | 9,10-bis(cyclohexyloxycarbonylmethyleneoxy)anthracene (1 part) | 0.013 | 0.010 |
| Migration Resistance Evaluation Comparative Example 1 |  | 9,10-dibutoxyanthracene (1 part) | 0.737 | 0.843 |

CELLOXIDE 2021P: 3',4'-epoxycyclohexylmethyl-3,4-epoxycyclohexanecarboxylate

Example for Evaluation of Migration Resistance of Composition in Photoradical Polymerization Migration Resistance Evaluation Example 10

100 parts of trimethylolpropane triacrylate as a photoradical polymerizable compound and 1 part of the 9,10-bis(methoxycarbonylmethyleneoxy)anthracene prepared in the same manner as in Preparation Example 1 as a photoradical polymerization sensitizer, were mixed, and the prepared composition was applied to a polyester film by a bar coater so that the film thickness would be 12 micron. The obtained coating film was covered with a low density polyethylene film (film thickness: 30 micron). Such samples were stored in a dark place for one day or for seven days, and the covering polyethylene film was peeled from each sample, washed with acetone and dried, the UV spectrum of the polyethylene film was measured, and the absorbance at 260 nm was measured. The absorbance attributable to the 9,10-bis(methoxycarbonylmethyleneoxy)anthracene was 0.015 after storage for 1 day and 0.016 after storage for 7 days.

Migration Resistance Evaluation Example 11

The same evaluation as in Migration Resistance Evaluation Example 10 was conducted except that 9,10-bis(ethoxycarbonylmethyleneoxy)anthracene prepared in the same manner as in Preparation Example 2 was used instead of the 9,10-bis(methoxycarbonylmethyleneoxy)anthracene. The absorbance at 260 nm of the polyethylene film washed with acetone was measured and as a result, the absorbance attributable to the 9,10-bis(ethoxycarbonylmethyleneoxy)anthracene was 0.014 after storage for 1 day and 0.015 after storage for 7 days.

Migration Resistance Evaluation Example 12

The same evaluation as in Migration Resistance Evaluation Example 10 was conducted except that 9,10-bis(isopropoxycarbonylmethyleneoxy)anthracene prepared in the same manner as in Preparation Example 3 was used instead of the 9,10-bis(methoxycarbonylmethyleneoxy)anthracene. The absorbance at 260 nm of the polyethylene film washed with acetone was measured and as a result, the absorbance attributable to the 9,10-bis(isopropoxycarbonylmethyleneoxy)anthracene was 0.024 after storage for 1 day and 0.022 after storage for 7 days.

Migration Resistance Evaluation Example 13

The same evaluation as in Migration Resistance Evaluation Example 10 was conducted except that 9,10-bis(tert-butoxycarbonylmethyleneoxy)anthracene prepared in the same manner as in Preparation Example 4 was used instead of the 9,10-bis(methoxycarbonylmethyleneoxy)anthracene. The absorbance at 260 nm of the polyethylene film washed with acetone was measured and as a result, the absorbance attributable to the 9,10-bis(tert-butoxycarbonylmethyleneoxy)anthracene was 0.037 after storage for 1 day and 0.033 after storage for 7 days.

Migration Resistance Evaluation Example 14

The same evaluation as in Migration Resistance Evaluation Example 10 was conducted except that 9,10-bis(n-butoxycarbonylmethyleneoxy)anthracene prepared in the same manner as in Preparation Example 5 was used instead of the 9,10-bis(methoxycarbonylmethyleneoxy)anthracene. The absorbance at 260 nm of the polyethylene film washed with acetone was measured and as a result, the absorbance attributable to the 9,10-bis(n-butoxycarbonylmethyleneoxy)anthracene was 0.022 after storage for 1 day and 0.015 after storage for 7 days.

Migration Resistance Evaluation Example 15

The same evaluation as in Migration Resistance Evaluation Example 10 was conducted except that 9,10-bis(methoxycarbonylmethylmethyleneoxy)anthracene prepared in the same manner as in Preparation Example 6 was used instead of the 9,10-bis(methoxycarbonylmethyleneoxy)anthracene. The absorbance at 260 nm of the polyethylene film washed with acetone was measured and as a result, the absorbance attributable to the 9,10-bis(methoxycarbonylmethylmethyleneoxy)anthracene was 0.007 after storage for 1 day and 0.004 after storage for 7 days.

Migration Resistance Evaluation Example 16

The same evaluation as in Migration Resistance Evaluation Example 10 was conducted except that 9,10-bis(ethoxycarbonylpropyleneoxy)anthracene prepared in the same manner as in Preparation Example 7 was used instead of the 9,10-bis(methoxycarbonylmethyleneoxy)anthracene. The absorbance at 260 nm of the polyethylene film washed with acetone was measured and as a result, the absorbance attributable to the 9,10-bis(ethoxycarbonylpropyleneoxy)anthracene was 0.032 after storage for 1 day and 0.030 after storage for 7 days.

Migration Resistance Evaluation Example 17

The same evaluation as in Migration Resistance Evaluation Example 10 was conducted except that 9,10-bis(ethoxycarbonylbutyleneoxy)anthracene prepared in the same manner as in Preparation Example 8 was used instead of the 9,10-bis(methoxycarbonylmethyleneoxy)anthracene. The absorbance at 260 nm of the polyethylene film washed with acetone was measured and as a result, the absorbance attributable to the 9,10-bis(ethoxycarbonylbutyleneoxy)anthracene was 0.022 after storage for 1 day and 0.021 after storage for 7 days.

Migration Resistance Evaluation Example 18

The same evaluation as in Migration Resistance Evaluation Example 10 was conducted except that 2-ethyl-9,10-bis(isopropoxycarbonylmethyleneoxy)anthracene prepared in the same manner as in Preparation Example 9 was used instead of the 9,10-bis(methoxycarbonylmethyleneoxy)anthracene. The absorbance at 260 nm of the polyethylene film washed with acetone was measured and as a result, the absorbance attributable to the 2-ethyl-9,10-bis(isopropoxycarbonylmethyleneoxy)anthracene was 0.031 after storage for 1 day and 0.032 after storage for 7 days.

Migration Resistance Evaluation Example 21

The same evaluation as in Migration Resistance Evaluation Example 10 was conducted except that 9,10-bis(n-pentyloxycarbonylmethyleneoxy)anthracene prepared in the same manner as in Preparation Example 18 was used instead of the 9,10-bis(methoxycarbonylmethyleneoxy)anthracene. The absorbance at 260 nm of the polyethylene film washed with acetone was measured and as a result, the absorbance attributable to the 9,10-bis(n-pentyloxycarbonylmethyleneoxy)anthracene was 0.051 after storage for 1 day and 0.032 after storage for 7 days.

Migration Resistance Evaluation Example 22

The same evaluation as in Migration Resistance Evaluation Example 10 was conducted except that 9,10-bis(cyclohexyloxycarbonylmethyleneoxy)anthracene prepared in the same manner as in Preparation Example 18 was used instead of the 9,10-bis(methoxycarbonylmethyleneoxy)anthracene. The absorbance at 260 nm of the polyethylene film washed with acetone was measured and as a result, the absorbance attributable to the 9,10-bis(cyclohexyloxycarbonylmethyleneoxy)anthracene was 0.051 after storage for 1 day and 0.035 after storage for 7 days.

Migration Resistance Evaluation Comparative Example 2

The same evaluation as in Migration Resistance Evaluation Example 10 was conducted except that a known photoradical sensitizer 9,10-dibutoxyanthracene was used instead of the 9,10-bis(methoxycarbonylmethyleneoxy)anthracene. The absorbance at 260 nm of the polyethylene film washed with acetone was measured and as a result, the absorbance of the 9,10-dibutoxyanthracene was 1.661 after storage for 1 day and 1.741 after storage for 7 days.

The results of Migration Resistance Evaluation Examples 10 to 18 and Migration Resistance Evaluation Comparative Example 2 are shown in Table 5.

migrates to a considerable extent to the film covering the photocationic polymerizable composition, whereas the degree of migration of the 9,10-bis(methoxycarbonylmethyleneoxy)anthracene compound of the present invention is very low in Examples, and the compound of the present invention is considered to be excellent in migration resistance.

Further, as evident from comparison between Migration Resistance Evaluation Examples 10 to 18, 21 and 22 and Migration Resistance Evaluation Comparative Example 2, in the photoradical polymerizable composition also, the known photoradical polymerization sensitizer 9,10-dibutoxyanthracene migrates to a considerable extent to the film covering the photoradical polymerizable composition, whereas the degree of migration of the 9,10-bis(methoxycarbonylmethyleneoxy)anthracene compound of the present invention is very low in Examples, and the compound of the present invention is considered to be excellent in migration resistance.

From the above results, it is found that the 9,10-bis(alkoxycarbonylalkyleneoxy)anthracene compound having ester groups of the present invention not only has a photopolymerization sensitizing effect comparable to the known photopolymerization sensitizer 9,10-dibutoxyanthracene compound for photocationic polymerization and photoradical polymerization but also has excellent migration resistance due to a structure having polar ester groups, and is very useful as a photopolymerization sensitizer.

INDUSTRIAL APPLICABILITY

The 9,10-bis(alkoxycarbonylalkyleneoxy)anthracene compound having ester groups of the present invention is an

TABLE 5

| | Polymerizable compound (parts by weight) | Photopolymerization sensitizer (parts by weight) | Absorbance at 260 nm | |
|---|---|---|---|---|
| | | | After one day | After one day |
| Migration Resistance Evaluation Example 10 | Trimethylolpropane triacylate (100 parts) | 9,10-bis(methoxycarbonylmethyleneoxy)anthracene (1 part) | 0.015 | 0.016 |
| Migration Resistance Evaluation Example 11 | | 9,10-bis(ethoxycarbonylmethyleneoxy)anthracene (1 part) | 0.014 | 0.015 |
| Migration Resistance Evaluation Example 12 | | 9,10-bis(isopropoxycarbonylmethyleneoxy)anthracene (1 part) | 0.024 | 0.022 |
| Migration Resistance Evaluation Example 13 | | 9,10-bis(tert-butoxycarbonylmethyleneoxy)anthracene (1 part) | 0.037 | 0.033 |
| Migration Resistance Evaluation Example 14 | | 9,10-bis(n-butoxycarbonylmethyleneoxy)anthracene (1 part) | 0.022 | 0.015 |
| Migration Resistance Evaluation Example 15 | | 9,10-bis(methoxycarbonylmethylmethyleneoxy)anthracene (1 part) | 0.007 | 0.004 |
| Migration Resistance Evaluation Example 16 | | 9,10-bis(ethoxycarbonylpropyleneoxy)anthracene (1 part) | 0.032 | 0.030 |
| Migration Resistance Evaluation Example 17 | | 9,10-bis(ethoxycarbonylbutyleneoxy)anthracene (1 part) | 0.022 | 0.021 |
| Migration Resistance Evaluation Example 18 | | 2-ethyl-9,10-bis(isopropoxycarbonylmethyleneoxy)anthracene (1 part) | 0.031 | 0.032 |
| Migration Resistance Evaluation Example 21 | | 9,10-bis(n-pentyloxycarbonylmethyleneoxy)anthracene (1 part) | 0.051 | 0.032 |
| Migration Resistance Evaluation Example 22 | | 9,10-bis(cyclohexyloxycarbonylmethyleneoxy)anthracene (1 part) | 0.051 | 0.035 |
| Migration Resistance Evaluation Comparative Example 2 | | 9,10-dibutoxyanthracene (1 part) | 1.661 | 1.741 |

As evident from comparison between Migration Resistance Evaluation Examples 1 to 9, 19 and 20 and Migration Resistance Evaluation Comparative Example 1, in the photocationic polymerizable composition, the known photocationic polymerization sensitizer 9,10-dibutoxyanthracene industrially very useful compound not only in having excellent effects as a photopolymerization sensitizer in photopolymerization reaction but also in that the photopolymerization sensitizer hardly undergoes migration and blooming due to a structure having ester groups as polar groups.

The invention claimed is:
1. A 9,10-bis(alkoxycarbonylalkyleneoxy)anthracene compound comprising ester groups, and having formula (1):

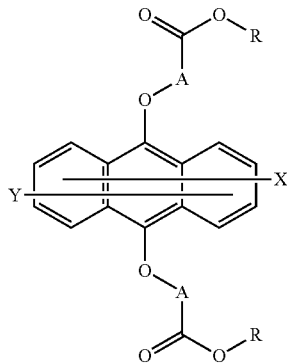
(1)

wherein
A is a $C_{1-20}$ alkylene group, optionally branched by an alkyl group,
R is a $C_{1-20}$ alkyl group, which is optionally branched by the alkyl group, optionally as a cycloalkyl group, or a cycloalkylalkyl group, and
X and Y are independently a hydrogen atom, a $C_{1-8}$ alkyl group, or a halogen atom.

2. A method for producing the compound of formula (1) of claim 1, the method comprising:
reacting a 9,10-dihydroxyanthracene compound of formula (2) and an ester compound of formula (3):

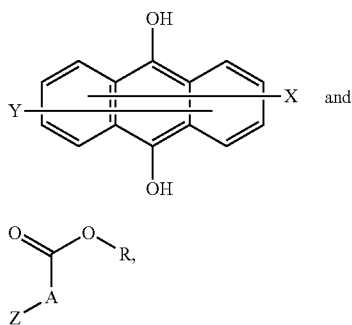
(2)
(3)

wherein each of X and Y is independently a hydrogen atom, a $C_{1-8}$ alkyl group, or a halogen atom, A is a $C_{1-20}$ alkylene group optionally branched by an alkyl group, R is a $C_{1-20}$ alkyl group, which is optionally branched by the alkyl group, optionally as a cycloalkyl group or a cycloalkylalkyl group, the $C_{1-20}$ alkyl group, alkyl group, cycloalkyl group, and cycloalkylalkyl group optionally being substituted by a hydroxy group, and one or more carbons of the $C_{1-20}$ alkyl group, alkyl group, cycloalkyl group, and cycloalkylalkyl group being optionally replaced by a non-peroxide oxygen atom, and Z is Cl, Br, or I

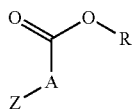

3. A method for producing the compound of formula (1) of claim 1, the method comprising:
reducing a 9,10-anthraquinone compound of formula (9):

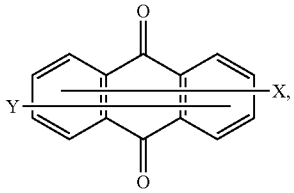
(9)

wherein X and Y are independently a hydrogen atom, a $C_{1-8}$ alkyl group, or a halogen atom, to obtain a 9,10-dihydroxyanthracene compound of formula (2):

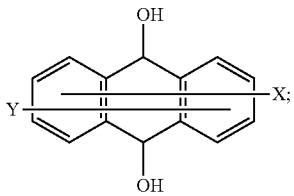
(2)

and
reacting the compound of formula (2): and an ester compound of formula (3):

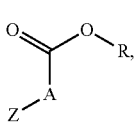
(3)

wherein A is a $C_{1-20}$ alkylene group, which is optionally branched by an alkyl group, R is a $C_{1-20}$ alkyl group, which is optionally branched by the alkyl group, optionally as a cycloalkyl group or a cycloalkylalkyl group, the $C_{1-20}$ alkyl group, alkyl group, cycloalkyl group, or cycloalkylalkyl group being optionally substituted by a hydroxy group, and one or more of carbon atoms of the $C_{1-20}$ alkyl group, alkyl group, cycloalkyl group, or cycloalkylalkyl group being optionally replaced by a non-peroxide oxygen atom, and Z is Cl, Br, or I.

4. A method for producing the compound of formula (1) of claim 1, the method comprising:
reacting a 9,10-dihydroxyanthracene compound of formula (2) and a carboxylic acid compound of formula (4):

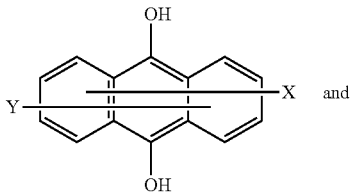
(2)

and

-continued

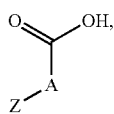
(4)

wherein X and Y are independently a hydrogen atom, a $C_{1-8}$ alkyl group, or a halogen atom, A is a $C_{1-20}$ alkylene group optionally branched by an alkyl group, and Z is Cl, Br, or I, to prepare a 9,10-bis(hydroxycarbonylalkyleneoxy)anthracene compound of formula (5)

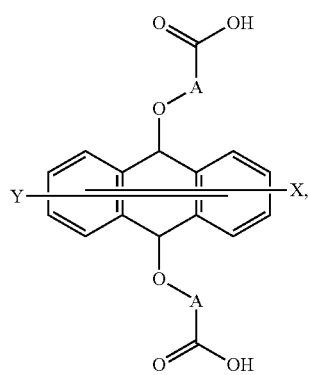
(5)

wherein A is a $C_{1-20}$ alkylene group optionally branched by an alkyl group, and each of X and Y is independently a hydrogen atom, a $C_{1-8}$ alkyl group or a halogen atom; and reacting the compound of formula (5) and an esterifying agent of formula (6), (7), or (8):

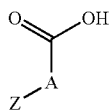

R-OH (6), R-D (7), or

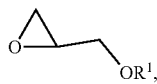
(8)

wherein R is a $C_{1-20}$ alkyl group, which is optionally branched by the alkyl group, optionally as a cycloalkyl group or a cycloalkylalkyl group, the $C_{1-20}$ alkyl group, alkyl group, cycloalkyl group, and cycloalkylalkyl group being optionally substituted by a hydroxy group, and one or more of carbon atoms of the $C_{1-20}$ alkyl group, alkyl group, cycloalkyl group, and cycloalkylalkyl group being optionally replaced by a non-peroxide oxygen atom D is Cl, Br, or I

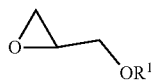

and $R^1$ is a hydrogen atom or a $C_{1-17}$ alkyl group, which is optionally branched by the alkyl group, optionally as a cycloalkyl group or a cycloalkylalkyl group, the $C_{1-20}$ alkyl group, alkyl group, cycloalkyl group, and cycloalkylalkyl group being optionally substituted by a hydroxy group, and one or more of carbon atoms of the $C_{1-20}$ alkyl group, alkyl group, cycloalkyl group, and cycloalkylalkyl group being optionally replaced by a non-peroxide oxygen atom, provided that when $R^1$ is a $C_{1-17}$ alkyl group, the number of carbon atoms in $R^1$ being smaller by 3 than the number of carbon atoms in R, excluding a case where the number of carbon atoms in R in the formula (1) is from 1 to 3.

5. A method for producing the compound of formula (1) of claim 1, the method comprising:

reducing a 9,10-anthraquinone compound of formula (9):

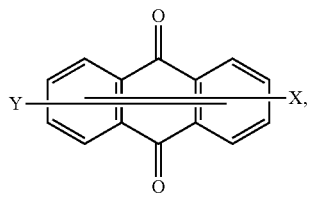
(9)

wherein X and Y are independently a hydrogen atom, a $C_{1-8}$ alkyl group, or a halogen atom, to obtain a 9,10-dihydroxyanthracene compound of formula (2):

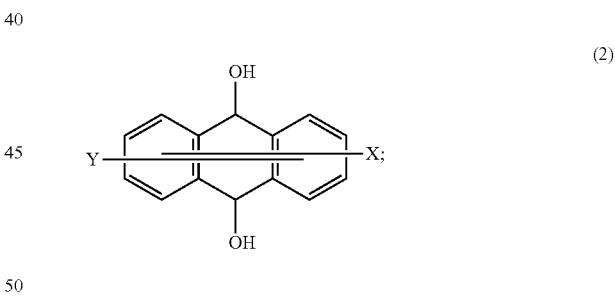
(2)

reacting the compound of formula (2) and a carboxylic acid compound of formula (4):

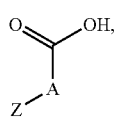
(4)

wherein A is a $C_{1-20}$ alkylene group optionally branched by an alkyl group, and Z is Cl, Br, or I, to prepare a 9,10-bis(hydroxycarbonylalkyleneoxy)anthracene compound of formula (5)

(5)

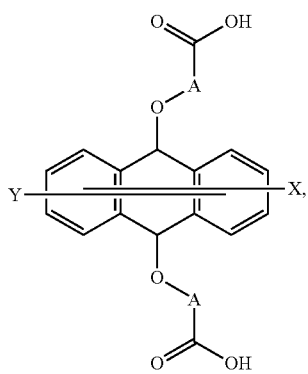

wherein A is a $C_{1-20}$ alkylene group optionally branched by an alkyl group, and X and Y are independently a hydrogen atom, a $C_{1-8}$ alkyl group or a halogen atom; and reacting the compound of formula (5) and an esterifying agent of (6), (7), or (8):

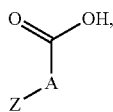

R—OH (6), R-D (7), or

(8)

wherein R is a $C_{1-20}$ alkyl group, which is optionally branched by the alkyl group, optionally as a cycloalkyl group or a cycloalkylalkyl group, the $C_{1-20}$ alkyl group, alkyl group, cycloalkyl group, and cycloalkylalkyl group being optionally substituted by a hydroxy group, and one or more carbon atoms of the $C_{1-20}$ alkyl group, alkyl group, cycloalkyl group, and cycloalkylalkyl group being optionally replaced by a non-peroxide oxygen atom D is Cl, Br, or I

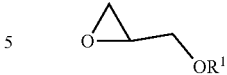

and $R^1$ is a hydrogen atom or a $C_{1-17}$ alkyl group, which is optionally branched by the alkyl group, optionally as a cycloalkyl group or a cycloalkylalkyl group, the $C_{1-20}$ alkyl group, alkyl group, cycloalkyl group, and cycloalkylalkyl group being optionally substituted by a hydroxy group, and one or more carbon atoms of the $C_{1-20}$ alkyl group, alkyl group, cycloalkyl group, and cycloalkylalkyl group being optionally replaced by a non-peroxide oxygen atom, provided that when $R^1$ is a $C_{1-17}$ alkyl group, the number of carbon atoms in $R^1$ is smaller by 3 than the number of carbon atoms in R, excluding a case where the number of carbon atoms in R in the formula (1) is from 1 to 3.

6. A photopolymerization sensitizer, comprising: the compound of formula (1) of claim 1.

7. The sensitizer of claim 6, wherein, in the 9,10-bis (alkoxycarbonylalkyleneoxy)anthracene compound of formula (1), R is a $C_{1-20}$ alkyl group, which is not substituted by a hydroxy group, and carbon atoms of the a $C_{1-20}$ alkyl group are not substituted by an oxygen atom.

8. The sensitizer of claim 6, wherein, in the 9,10-bis (alkoxycarbonylalkyleneoxy)anthracene compound of formula (1), A is a $C_1$ alkylene group.

9. A photopolymerization initiator composition, comprising:
the photopolymerization sensitizer of claim 6; and
a photopolymerization initiator.

10. A photopolymerizable composition, comprising:
the polymerization initiator composition of claim 9; and
a photocationic polymerizable compound.

11. A photopolymerizable composition, comprising:
the photopolymerization initiator composition of claim 9; and
a photoradical polymerizable compound.

12. A method of polymerizing the photopolymerizable composition of claim 10, the method comprising:
applying energy rays comprising light having a wavelength in a range of from 300 nm to 500 nm to the photopolymerizable composition.

13. The method of claim 12, wherein an irradiation source of the energy rays is an ultraviolet LED or a semiconductor laser with a center wavelength of 365 nm, 375 nm, 385 nm, 395 nm, or 405 nm.

* * * * *